(12) United States Patent
Sawyer et al.

(10) Patent No.: US 6,797,723 B1
(45) Date of Patent: Sep. 28, 2004

(54) HETEROCYCLE SUBSTITUTED DIPHENYL LEUKOTRIENE ANTAGONISTS

(75) Inventors: Jason Scott Sawyer, Indianapolis, IN (US); Douglas Wade Beight, Frankfort, IN (US); Edward C R Smith, Fishers, IN (US); William Thomas McMillen, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 182 days.

(21) Appl. No.: 10/111,544

(22) PCT Filed: Nov. 9, 2000

(86) PCT No.: PCT/US00/30942
§ 371 (c)(1),
(2), (4) Date: Apr. 24, 2002

(87) PCT Pub. No.: WO01/34580
PCT Pub. Date: May 17, 2001

Related U.S. Application Data

(60) Provisional application No. 60/164,703, filed on Nov. 11, 1999.

(51) Int. Cl.[7] .................. A61K 31/415; A61K 31/426; C07D 231/12; C07D 277/30
(52) U.S. Cl. ...................... 514/406; 514/365; 548/194; 548/125; 548/127; 548/134; 548/136; 548/236; 548/214; 548/376.1; 548/247; 548/562; 548/572; 548/377.1; 549/66; 549/501
(58) Field of Search .................. 548/194, 125, 548/127, 134, 136, 236, 377.1, 214, 376.1, 247, 562, 572; 514/365, 406; 549/66, 501

(56) References Cited

U.S. PATENT DOCUMENTS

| 5,462,954 A | 10/1995 | Baker et al. |
| 5,543,428 A | 8/1996 | Sawyer et al. |
| 5,910,505 A | 6/1999 | Fleisch et al. |
| 6,071,949 A | 6/2000 | Mulshine et al. |

FOREIGN PATENT DOCUMENTS

| EP | 544488 | 3/1998 | ........... C07C/59/68 |
| WO | WO 01/34137 | 5/2001 | .......... A61K/45/06 |
| WO | WO 01/34580 | 5/2001 | ......... C07D/263/32 |
| WO | WO 01/85166 | 11/2001 | |

OTHER PUBLICATIONS

"Synthetic and Structure /Activity Studies on Acid–Substituted 2–Arylphenols" by J. Scott Sawyer, et al., Journal of Medicial Chemistry, 1995, 38 pp. 4411–4432.

"Second Generation Leukotriene B4 Receptor Antagonists Related to SC–41930" by Penning, Thomas D. et al., J. Med. Chem., 1995, 38, pp. 858–868.

"Leukotriene B4 (LTB4) Receptor Antagonists" by Harper, Richard W. et. al., J. Med. Chem., 1994, 37, pp. 2411–2420.

*Primary Examiner*—Laura L. Stockton
(74) *Attorney, Agent, or Firm*—Roger S. Benjamin

(57) ABSTRACT

The invention relates to novel heterocycle substituted diphenyl leukotriene $B_4$ ($LTB_4$) antagonists, to compositions containing such compounds, and to methods of using such compounds for treatment of inflammatory diseases.

26 Claims, No Drawings

HETEROCYCLE SUBSTITUTED DIPHENYL LEUKOTRIENE ANTAGONISTS

CROSS REFERENCE TO RELATED APPLICATION

This case claims the priority benefit of U.S. Provisional Patent Application Serial No. 60/164,703, filed Nov. 11, 1999, the disclosure of which is incorporated herein by reference.

BACKGROUND OF THE INVENTION

The metabolic routes in which various compounds are biosynthesized from arachidbnic acid, are collectively called the "Arachidonic Acid Cascade."

Leukotriene $B_4$ ($LTB_4$) is one of many products resulting from the arachidonic acid cascade.

Moreover, $LTB_4$ in high concentration has been detected at the sites of various inflammatory conditions, for example, rheumatism, spinal arthritis (see Klickstein L. B., Shapleigh, C. and Goetzl, E. J. (1980) J. Clin. Invest., 66, 1166–1170), gout (Rae, S. A., Davidson, E. M. and Smith, M. J. H. (1982) Lancet II 1122–1123), psoriasis (see Grabbe, J., Czarnetzki, B. M., Rosenbach, T. and Mardin, M. (1984) J. Invest. Dermatol., 82, 477–479), ulcerative colitis (see Sharon, P. and Stenson, W. F. (1984) Gastroenterology 86, 453–460). and respiratory disease (see O'Driscoll, B. R., Cromwell, O. and Kay, A. B. (1984) Clin. Exp., Immunol., 55, 397–404). The facts described above show that $LTB_4$ is deeply related to various forms of inflammation. It has been suggested that compounds antagonizing $LTB_4$ activity may be valuable in the treatment of inflammatory diseases caused by tissue degrading enzymes and reactive chemicals liberated by tissue-infiltrating and aggregating polymorphonuclear leukocytes.

For example, PCT Japanese National Publication No. 6-502164 describes novel monocylic or bicyclic aryl compounds are selectively antagonistic to $LTB_4$ and are useful for treatment of rheumatoid arthritis, gout, psoriasis and inflammatory bowel disease. Japanese Unexamined Patent Publication (Kokai) No. 4-244023 describes that omega 6 series unsaturated fatty acids such as γ-linolenic acid are useful for treatment of arrhythmia, acute myocardial infarction etc, by inhibiting production of $LTB_4$. Japanese Unexamined Patent Publication No. 5-310668 describes that a novel leucine derivative has an inhibitory action to $LTA_4$ hydrolase and is useful for treatment and prophylaxis of allergic diseases such as bronchial asthma, various inflammatory diseases, and ischemia-reperfusion disorders. Japanese Unexamined Patent Publication (Kokai) No. 1-190656 discloses that novel leukotriene $B_3$ dimethyl amide has an antagonistic action to $LTB_4$ and is useful as anti-inflammatory drug, anti-rheumatic drug and gout-treatment drug.

The article, "Second Generation Leukotriene B4 Receptor Antagonists Related to SC-41930: Heterocyclic Replacement of the Methyl Ketone Pharmacophore", J. Med Chem, 1995, 38, p.858–868 by Penning, Thomas D. et. al.; describes heterocycle substituted $LTB_4$ antagonists.

Pyrazole $LTB_4$ antagonists are disclosed in the article, "Leukotriene B4 ($LUB_4$) Receptor Antagonists: A Series of (Hydroxyphenyl)pyrazoles" by Richard W. Harper, et. al., J. Med Chem, 1994, 37, pgs. 2411–2420.

Leukotriene $B_4$ antagonists, inclusive of diphenyl ethers such as 2-[2-propyl-3-[3-[2-ethyl-5-hydroxy-4-(4-fluorophenyl)phenoxylpropoxy]phenoxy]benzoic acid, are described in U.S. Pat. No. 5,462,954, the disclosure of which is incorporated herein by reference. The same type of leukotriene $B_4$ antagonists are described in the article, "Synthetic and Structure/Activity Studies on Acid-Substituted 2-Arylphenols: Discovery of 2-[2-Propyl-3-(3-[2-ethyl-4-(4-fluorophenyl)-5-hydroxyphenoxy]-propoxy] phenoxy]benzoic Acid, a High-Affinity Leukotriene $B_4$ Receptor Antagonist" by J. Scott Sawyer, et. al., Journal of Medicinal Chemistry, 1995, 38, pgs. 4411–4432.

These diphenyl ether leukotriene $B_4$ antagonists, in combination with a 2',2'-difluoronucleoside analog (e.g., GEM-CITABINE HCl, have also been found to have utility in the treatment of various cancers, as further described in Provisional Patent Application Serial No. 60/164786, filed 11 Nov. 1999, the disclosure of which is incorporated herein by reference.

Currently, anti-inflammatory drugs are classified as steroidal and non-steroidal. Although these drugs provide anti-inflammatory action they all have drawbacks which limit their use. A more recent approach to the moderation of inflammation focuses on blocking the action of arachidonic acid metabolites.

Leukotriene $B_4$ antagonists are useful for a wide variety of Inflammatory Diseases, but it is expected that various of these antagonists will show superior results with particular disease states. This is one reason it is desirable to develop new leukotriene $B_4$ antagonists such as the compounds of this invention.

SUMMARY OF THE INVENTION

The present invention is directed to novel heterocycle substituted diphenyl compounds of formula (I)

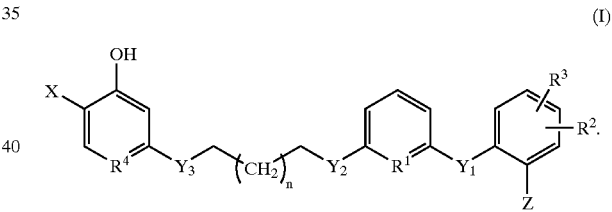

(I)

Another aspect of this invention are pharmaceutical compositions containing the compounds of formula (I).

Another aspect of this invention is a method of using the compounds of the invention in the prevention and treatment of $LTB_4$ induced illnesses.

Another aspect of this invention is a compound of formula (I) for use as a medicament in the treatment or prevention of Inflammatory Diseases.

Another aspect of this invention is a process for preparing a compound of Formula (I).

DETAILED DESCRIPTION

I. Definitions:

The term, "Acidic Group" means an organic group which when attached as the "Z" substituent of formula (I) or the "Z2" substituent of formula (II) acts as a proton donor capable of hydrogen bonding. An illustrative acidic group is carboxyl.

The term, "Active Ingredient" means the diphenyl leukotriene $B_4$ antagonist compounds generically described by formula I and formula II or the list of specific diphenyl compounds disclosed, infra., as well as the salts, solvates, and prodrugs of such compounds.

The term, "alkenyl" means a monovalent radical of the generic formula $C_nH_{2n}$ such as ethenyl, n-propenyl, isopropeneyl, n-butenyl, isobutenyl, 2-butenyl, and 3-butenyl.

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, sec-butyl, n-pentyl, and n-hexyl.

The term, "alkaryl" means an aryl radical substituted with an alkyl or substituted aryl group, for example:

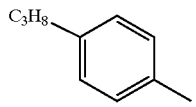

In the term, "$C_6$–$C_{20}$ alkaryl" the numerical subscripts refer to the total number of carbon atoms in the radical.

The term, "$C_6$–$C_{20}$ aralkyl" means an alkyl radical substituted with an aryl or substituted aryl group, for example:

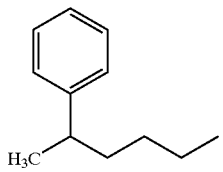

In the term, "$C_6$–$C_{20}$ aralkyl" the numerical subscripts refer to the total number of carbon atoms in the radical.

The term, "carbocyclic group" refers to a five, six, seven, or eight membered saturated, unsaturated or aromatic ring containing only carbon and hydrogen (e.g., benzene, cyclohexene, cyclohexane, cyclopentane).

The term, "cycloalkyl" means a carbocyclic non-aromatic monovalent radical such as cyclopropyl, cyclobutyl, cyclopentyl, cyclohexyl, cycloheptyl, and cyclooctyl.

The term, "halo" means fluoro, chloro, bromo, or iodo.

The term, "heterocyclic radical(s)" refers to a radical having a saturated, unsaturated or aromatic five membered substituted or unsubstituted ring containing from 1 to 4 hetero atoms.

The term, "Inflammatory Diseases" refers to diseases such as inflammatory bowel disease, sepsis, septic shock, adult respiratory distress syndrome, pancreatitis, trauma-induced shock, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes, polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogarmaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to act as an antagonist for leukotriene $B_4$ and its deleterious products.

The term, "$LTB_4$ antagonist" means a pharmaceutical agent capable of preventing or reducing to a therapeutically significant degree the adverse activity of $LTB_4$ in mammals and having a average CD11b/CD18 $IC_{50}$(nM) assay result of 10000 or less and preferably of 100 or less.

The term, "mammal" includes human.

The term, "N-sulfonamidyl" means the radical:

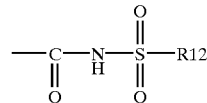

where R12 is $C_1$–$C_{10}$ alkyl, aryl, $C_1$–$C_6$ alkyl substituted aryl, $C_6$–$C_{20}$ alkaryl, or $C_6$–$C_{20}$ aralkyl.

The term, "substituted alkyl" means an alkyl group further substituted with one or more radical(s) selected from halo, $C_1$–$C_6$ alkyl, aryl, benzyl, $C_2$–$C_6$ alkenyl, $C_2$–$C_6$ alkynyl, $C_3$–$C_8$ cycloalkyl, $C_1$–$C_8$ alkoxy, $C_1$–$C_6$ haloalkyl (e.g., —$CF_3$).

The term, "substituted aryl" means an aryl group further substituted with one or more radical(s) selected from halo, $C_1$–$C_6$ alkyl, aryl, benzyl, $C_2$–$C_6$ alkenyl, $C_2$–$C_6$ alkynyl, $C_3$-$C_8$ cycloalkyl, $C_1$–$C_8$ alkoxy, $C_1$–$C_6$ haloalkyl (e.g., —$CF_3$).

The term, "tetrazolyl" refers to an acidic group represented by either of the formulae:

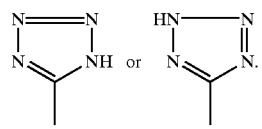

II. Compounds of the Invention:

The present invention is directed to novel heterocyclic substituted diphenyl compounds of formula (I)

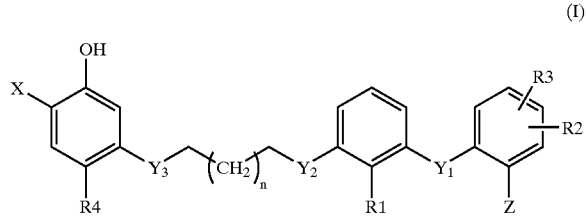

wherein:

X is selected from the group consisting of,
(i) a five membered substituted or unsubstituted heterocyclic radical containing from 1 to 4 hetero atoms independently selected from sulfur, nitrogen or oxygen; or
(ii) a fused bicyclic radical wherein a carbocyclic group is fused to two adjacent carbon atoms of the five membered heterocyclic radical, (i);

$Y_1$ is a bond or divalent linking group containing 1 to 9 atoms;

$Y_2$ and $Y_3$ are divalent linking groups independently selected from —$CH_2$—, —O—, and —S—;

Z is an Acidic Group;

R1 is $C_1$–$C_{10}$ alkyl, aryl, $C_3$–$C_{10}$ cycloalkyl, $C_2$–$C_{10}$ alkenyl, $C_2$–$C_{10}$ alkynyl, $C_6$–$C_{20}$ aralkyl, $C_6$–$C_{20}$ alkaryl, $C_1$–$C_{10}$ haloalkyl, $C_6$–$C_{20}$ aryloxy, or $C_1$–$C_{10}$ alkoxy;

R2 is hydrogen, halogen, $C_1$–$C_{10}$ haloalkyl, $C_1$–$C_{10}$ alkoxy, $C_1$–$C_{10}$ alkyl, $C_3$–$C_8$ cycloalkyl, Acidic Group, or —$(CH_2)_{1-7}$(Acidic Group);

R3 is hydrogen, halogen, $C_1$–$C_{10}$ alkyl, aryl, $C_1$–$C_{10}$ haloalkyl, $C_1$–$C_{10}$ alkoxy, $C_1$–$C_{10}$ aryloxy, $C_3$–$C_8$ cycloalkyl;

R4 is $C_1$–$C_4$ alkyl, $C_3$–$C_4$ cycloalkyl, —$(CH_2)_{1}$-7 (cycloalkyl), $C_2$–$C_4$ alkenyl, $C_2$–$C_4$ alkynyl, benzyl, or aryl; and n is 0, 1, 2, 3, 4, 5, or 6;

or a pharmaceutically acceptable salt, solvate, or prodrug derivative thereof.

III. Preferred Compounds of the Invention:

III A. Preferred X substituents:

A "substituted heterocyclic radical" is preferably Substitued with from 1 to 3 groups independently selected from hydrogen, halo, $C_1$–$C_{10}$ alkyl, $C_1$–$C_{10}$ haloalkyl, $C_1$–$C_{10}$ alkoxy, aryl, or $C_6$–$C_{20}$ aryloxy.

Preferred Group 1 of X substituent (symbol, "PG1-X")

Preferred compounds of the invention are those wherein X is a heterocyclic radical selected from the group consisting of substituents represented by the following structural formulae:

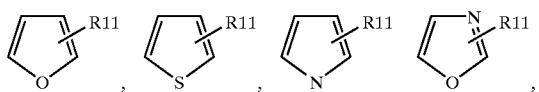

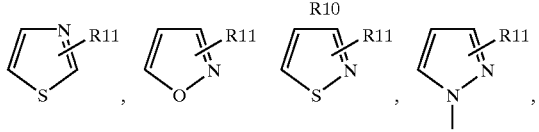

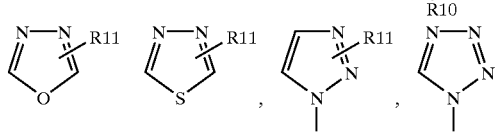

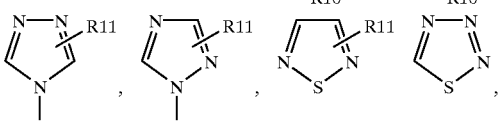

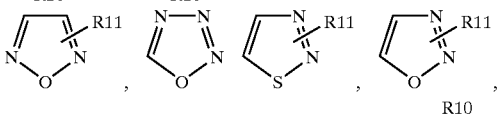

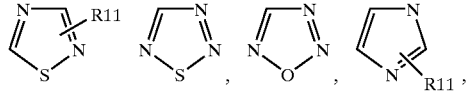

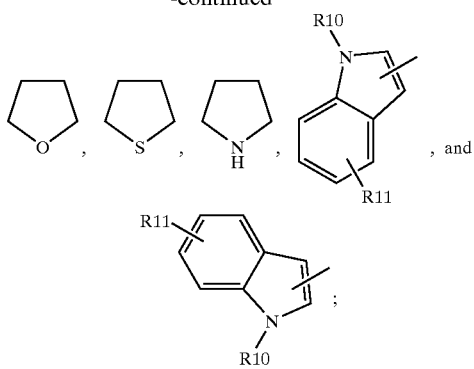

where R10 is a radical selected from hydrogen or $C_1$–$C_4$ alkyl; and R11 is a radical selected from hydrogen, halo, $C_1$–$C_{10}$ alkyl, $C_1$–$C_{10}$ haloalkyl, $C_1$–$C_{10}$ alkoxy, aryl, or $C_6$–$C_{20}$ aryloxy. Preferred R10 groups are hydrogen, methyl, or phenyl. Moreover, any of the above heterocyclic radicals illustrated by structural formulae may attach to the diphenyl leukotriene antagonist of formulae (I) by any monovalent bond originating on a suitable carbon or nitrogen atom in its ring structure.

For example, the pyrrole radical may attach to the diphenyl molecule by a single bond originating at any carbon atom or any nitrogen atom which has less than three bonds in the hererocyclic ring;

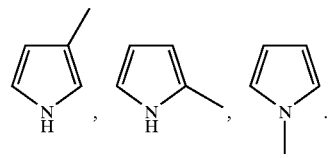

A preferred form of the substituent X is a fused bicyclic radical wherein a carbocyclic group is fused to two adjacent carbon atoms of the five membered heterocyclic radical, for example:

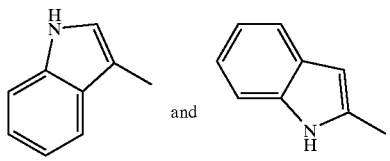

III B. Preferred Group 2 of X substituent (symbol, "PG2-X"):

Most preferred as the X substituents are the heterocyclic radicals;

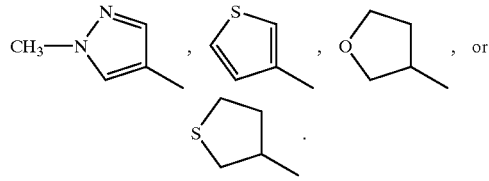

III C. Excluded X substituents:

The heterocyclic radical X of Formula (I) does not include 3-bromo-1,2,4 thiadiazole since the $LTB_4$ antagonist activity of compounds containing this radical is considered too low to be an aspect of this invention.

III D. Preferred $Y_1$ substituents:

$Y_1$ is a bond or divalent linking group containing 1 to 9 atoms independently selected from carbon, hydrogen, sulfur, nitrogen, and oxygen;

Preferred Croup 1 of $Y_1$ substituent (symbol, "PG1-$Y_1$")

Preferred compounds of the invention are those wherein $Y_1$ is a divalent linking group selected from the group consisting of substituents represented by the following formulae:

$$-O-, \quad -S-, \quad -CH_2-, \quad -SO_2-,$$

$$-\overset{O}{\underset{}{S}}-, \quad -\overset{O}{\underset{O}{S}}-\overset{}{\underset{R13}{N}}-, \quad -\overset{}{\underset{R13}{N}}-, \quad -\overset{O}{\underset{}{C}}-,$$

$$-CH_2-CH_2-, \quad -O-CH_2-, \quad -S-CH_2-,$$

$$-\overset{}{\underset{R13}{N}}-CH_2-, \quad -\overset{O}{\underset{O}{S}}-CH_2-, \text{ and } -\overset{O}{\underset{}{C}}-CH_2-,$$

where R13 is hydrogen, methyl, or ethyl;

The above divalent groups may be used in their forward or reversed positions. For example, the group;

$$-\overset{O}{\underset{}{C}}-CH_2-,$$

may be positioned as either,

[structure with R1, R2, R3, Z]

or

[structure with R1, R2, R3, Z]

in the displayed fragment of formula (I).

III E. Preferred Group 2 of $Y_1$ substituent (symbol, "IPG2-$Y_1$").

The most preferred divalent $Y_1$ substituent is the group;

$$-O-.$$

III F. Preferred Group 1 of $Y_2$ substituent (symbol, "IPG1-$Y_2$") and Preferred Group 1 of $Y_3$ substituent (symbol, "PG1-Y3")

The $Y_2$ and $Y_3$ substituents are preferably selected from —S— and —O—.

III G. Preferred Group 2 of $Y_2$ substituent (symbol, "PG2-$Y_2$") and Preferred Group 2 of $Y_3$ substituent (symbol, "PG2-$Y_3$"):

Most preferably both $Y_2$ and $Y_3$ are the group;

$$-O-.$$

III H. Preferred Group 1 of Z substituent (symbol, "PG1-Z"):

Z is the Acidic Group as previously defined. Preferred is an acidic group selected from the following:

$$-\overset{O}{\underset{O}{C}}-\overset{H}{\underset{}{N}}-\overset{O}{\underset{O}{S}}-R12,$$

tetrazolyl,

—SO$_3$H, $$-\overset{O}{\underset{OH}{P}}-OH, \quad -O-\overset{O}{\underset{OH}{P}}-OH, \quad -\overset{O}{\underset{}{C}}-OH \text{ or}$$

[thiadiazole structure with HO and N, N, S]

where R12 is $C_1$–$C_{10}$ alkyl, aryl, $C_6$–$C_{20}$ alkaryl, or $C_6$–$C_{20}$ aralkyl. Preferred R12 groups are represented by the formulae:

[tolyl with CH$_3$] and [phenyl].

III I. Preferred Group 2 of Z substituent (symbol, "PG2-Z"):
Highly preferred are the acidic groups; -5-tetrazolyl, N-acyl sulfonamide, —SO$_3$H, and carboxyl.

III J. Preferred Group 3 of Z substituent (symbol, "PG3-Z"):
Carboxyl is the most preferred Z substituent.

III K. Preferred Group 1 of n subscript variable (symbol, "PG1-n")
The most preferred integer values for the divalent linking group, —(CH$_2$)$_n$—, are n=1, n=2, and n=3.

III L. Preferred Group 2 of n subscript variable (symbol, "PG2-n")
The most preferred integer value of n for the divalent linking group, —(CH$_2$)$_n$— is n =1.

III M. Preferred Group 1 of R1 substituent (symbol, "PG1-R1"):
A preferred Rl group is methyl, ethyl, n-propyl, isopropyl, n-butyl, sec-butyl, and 2-propenyl; with n-propyl being most preferred.

III N. Preferred Group 1 of R2 substituent (symbol, "PG1-R2") and Preferred Group 1 of R3 substituent (symbol, "PG1-R3"):
Preferred R2 and R3 groups are those wherein R2 and R3 are independently selected from hydrogen or methyl, ethyl, methoxy, ethoxy, halo, or —CF$_3$; with R2 and R3 both being hydrogen as most preferred.

III O. Preferred Group 1 of R4 substituent (symbol, "PG1-R4":)

Preferred R4 substituents are ethyl, propyl, and isopropyl.

III P. Combinations of substituents of the compound of Formula (I):

The substituents of formula (I) are defined as "Z", "X", "n", "R1", "R2", "R3", "R4", "Y1", "Y2", and "Y3". Moreover, as described in the preceding section, within each of the defined substituents of Formula (I) are "preferred" and "most preferred" subgroups which define the variety of substituents to be used in the definition of $LTB_4$ antagonists of the invention. These preferred subgroups are defined by designations such as "PG1-R4" as recited above. It is often advantageous to use combinations of preferred groups or combinations of preferred groups together with the general definition of variables given in Formula (I). Suitable combinations of substituents are shown in the following three Tables (viz., R-Table, Y-Table & XZn-Table).

The following R-Table is used to select combinations of general and preferred groupings of the variables R1, R2, R3 and R4 for substitution in formula (I), as follows:

| R variables Combination Code | R1 group choice | R2 group choice | R3 group choice | R4 group choice |
| --- | --- | --- | --- | --- |
| R01 | R1 | R2 | R3 | R4 |
| R02 | R1 | R2 | R3 | PG1-R4 |
| R03 | R1 | R2 | PG1-R3 | R4 |
| R04 | R1 | R2 | PG1-R3 | PG1-R4 |
| R05 | R1 | PG1-R2 | R3 | R4 |
| R06 | R1 | PG1-R2 | R3 | PG1-R4 |
| R07 | R1 | PG1-R2 | PG1-R3 | R4 |
| R08 | R1 | PG1-R2 | PG1-R3 | PG1-R4 |
| R09 | PG1-R1 | R2 | R3 | R4 |
| R10 | PG1-01 | R2 | R3 | PG1-R4 |
| R11 | PG1-R1 | R2 | PG1-R3 | R4 |
| R12 | PG1-R1 | R2 | PG1-R3 | PG1-R4 |
| R13 | PG1-R1 | PG1-R2 | R3 | R4 |
| R14 | PG1-R1 | PG1-R2 | R3 | PG1-R4 |
| R15 | PG1-R1 | PG1-R2 | PG1-R3 | R4 |
| R16 | PG1-R1 | PG1-R2 | PG1-R3 | PG1-R4 |

Thus, for example, the substituent combination, "R14" describes a substituent combinatorial choice for Formula (I) wherein R1 is selected from the preferred set of variables, "PG1R1", that is, methyl, ethyl, n-propyl, isopropyl, n-butyl, sec-butyl, and 2-propenyl; the R2 substituent is selected from the preferred set of variables, "PG1-R2", that is, hydrogen or methyl, ethyl, methoxy, ethoxy, halo, or —$CF_3$; the variable R3 has the scope defined in the generic formula (I), and the substituents suitable for R4 are selected from the preferred group, "PG1-R4" having the preferred set of variables, ethyl, propyl, and isopropyl.

The following Y-Table is used to select broad and preferred groupings of the variables $Y_1$, $Y_2$, and $Y_3$ for substitution in formula (I), as follows:

| Y variables combination code | Y1 group choice | Y2 group choice | Y3 group choice |
| --- | --- | --- | --- |
| Y01 | Y1 | Y2 | Y3 |
| Y02 | Y1 | Y2 | PG1-Y3 |
| Y03 | Y1 | Y2 | PG2-Y3 |
| Y04 | Y1 | PG1-Y2 | Y3 |
| Y05 | Y1 | PG2-Y2 | Y3 |
| Y06 | Y1 | PG1-Y2 | PG1-Y3 |
| Y07 | Y1 | PG1-Y2 | PG2-Y3 |
| Y08 | Y1 | PG2-Y2 | PG1-Y3 |
| Y09 | Y1 | PG2-Y2 | PG2-Y3 |
| Y10 | PG1-Y1 | Y2 | Y3 |
| Y11 | PG1-Y1 | Y2 | PG1-Y3 |
| Y12 | PG1-Y1 | Y2 | PG2-Y3 |
| Y13 | PG1-Y1 | PG1-Y2 | Y3 |
| Y14 | PG1-Y1 | PG1-Y2 | PG1-Y3 |
| Y15 | PG1-Y1 | PG1-Y2 | PG2-Y3 |
| Y16 | PG1-Y1 | PG2-Y2 | Y3 |
| Y17 | PG1-Y1 | PG2-Y2 | PG1-Y3 |
| Y18 | PG1-Y1 | PG2-Y2 | PG2-Y3 |
| Y19 | PG2-Y1 | Y2 | Y3 |
| Y20 | PG2-Y1 | Y2 | PG1-Y3 |
| Y21 | PG2-Y1 | Y2 | PG2-Y3 |
| Y22 | PG2-Y1 | PG1-Y2 | Y3 |
| Y23 | PG2-Y1 | PG1-Y2 | PG1-Y3 |
| Y24 | PG2-Y1 | PG1-Y2 | PG2-Y3 |
| Y25 | PG2-Y1 | PG2-Y2 | Y3 |
| Y26 | PG2-Y1 | PG2-Y2 | PG1-Y3 |
| Y27 | PG2-Y1 | PG2-Y2 | PG2-Y3 |

The following XZn-Table is used to select broad and preferred groupings of the variables X, Z, and n for substitution in formula (I), as follows:

| XZn variables combination code | X group choice | Z Group Choice | n integer group choice |
| --- | --- | --- | --- |
| XZn01 | X | Z | n |
| XZn02 | X | Z | PG1-n |
| XZn03 | X | Z | PG2-n |
| XZn04 | X | PG1-Z | n |
| XZn05 | X | PG2-Z | n |
| XZn06 | X | PG3-Z | n |
| XZn07 | X | PG1-Z | PG1-n |
| XZn08 | X | PG2-Z | PG1-n |
| XZn09 | X | PG3-Z | PG1-n |
| XZn10 | X | PG1-Z | PG2-n |
| XZn11 | X | PG2-Z | PG2-n |
| XZn12 | X | PG3-Z | PG2-n |
| XZn13 | PG1-X | Z | n |
| XZn14 | PG1-X | Z | PG1-n |
| XZn15 | PG1-X | Z | PG2-n |
| XZn16 | PG1-X | PG1-Z | n |
| XZn17 | PG1-X | PG2-Z | n |
| XZn18 | PG1-X | PG3-Z | n |
| XZn19 | PG2-X | PG1-Z | PG1-n |
| XZn20 | PG2-X | PG2-Z | PG1-n |
| XZn21 | PG2-X | PG3-Z | PG1-n |
| XZn22 | PG2-X | PG1-Z | PG2-n |
| XZn23 | PG2-X | PG2-Z | PG2-n |
| XZn24 | PG2-X | PG3-Z | PG2-n |

How to Use the Tables:

Any of the individual 16 combinations of the R substituents depicted in the R-Table may be used in combination with any of the 27 individual combinations of Y substituents depicted in the Y-Table, which may be used with any of the 24 combinations of Xzn substituents depicted in the XZn-Table. For example, the substituent combination choice "R07, Y21, XZn03" defines substituent set selections for a subset of formula (I) useful in the practice of the invention.

III Q. Preferred compounds of the invention are described by formula (II):

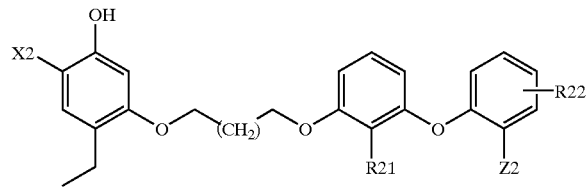

wherein;

X2 is a heterocyclic radical selected from,

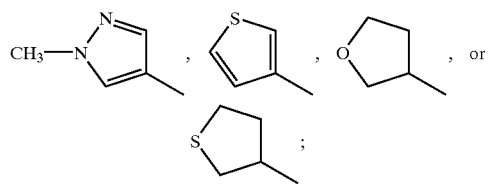

R21 is ethyl, 2-propen-1-yl, 3-propen-1-yl, n-propyl, iso-propyl, n-butyl, sec-butyl, or tert-butyl; and R22 is hydrogen, n-butyl, sec-butyl, flouro, chloro, —$CF_3$, or tert-butyl.

Z2 is carboxyl, tetrazolyl, N-sulfonamidyl. Preferred Compounds of the Invention:

III R. Specific compounds preferred as $LTB_4$ antagonists are represented by the following structural formulae:

(C1):

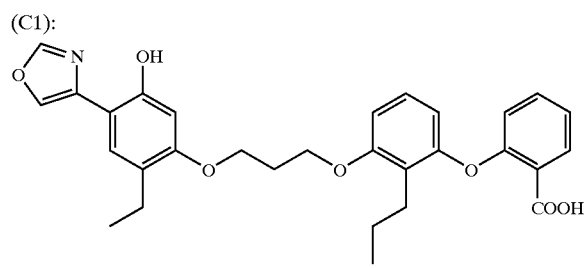

(C2):

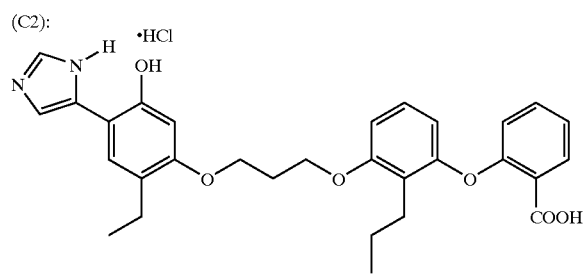

(C3):

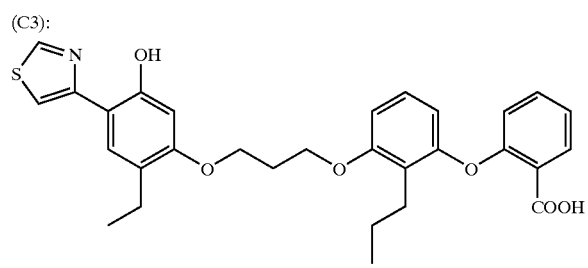

(C4):

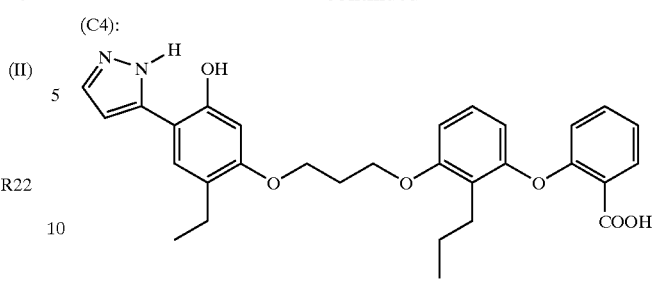

(C5):

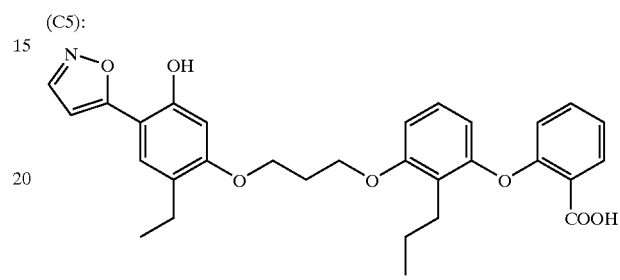

(C6):

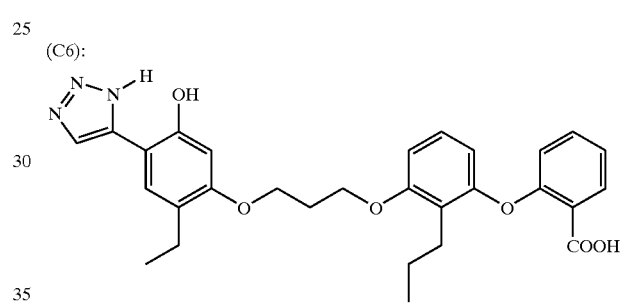

(C7):

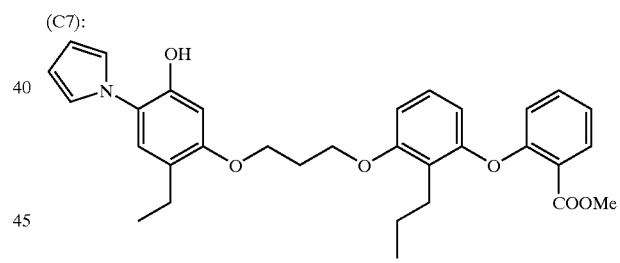

(C8):

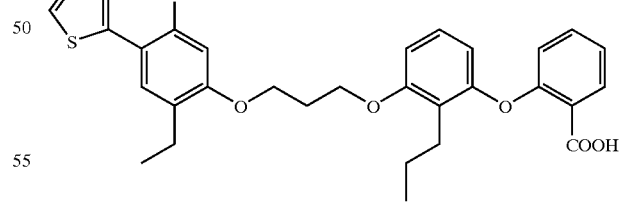

(C9):

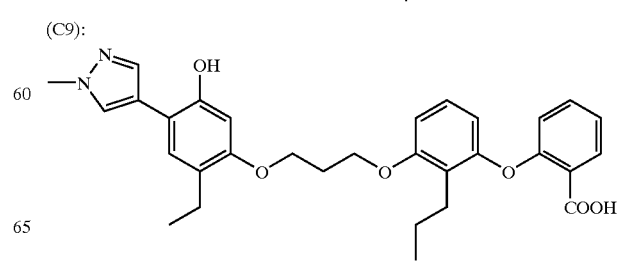

(C10):
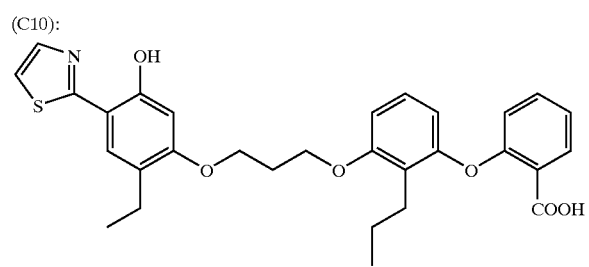
(C16):
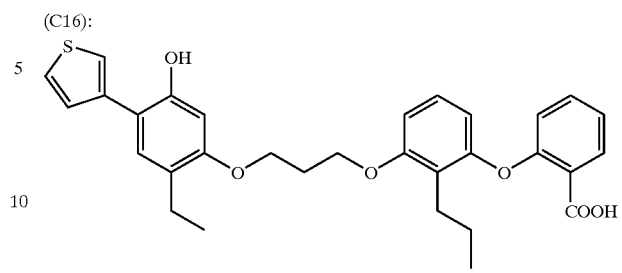
(C11):
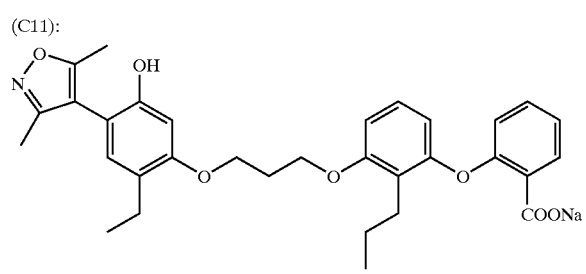
(C17):
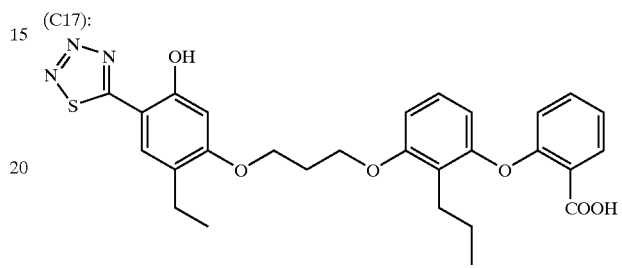
(C12):
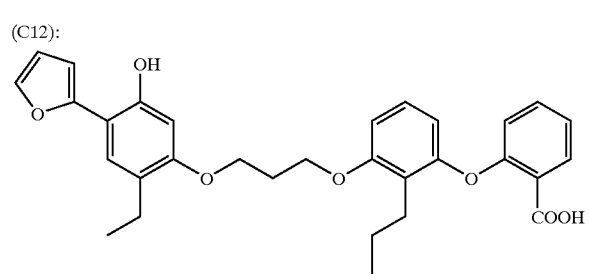
(C18):
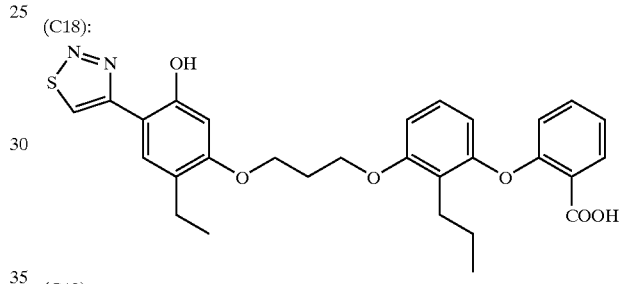
(C13):
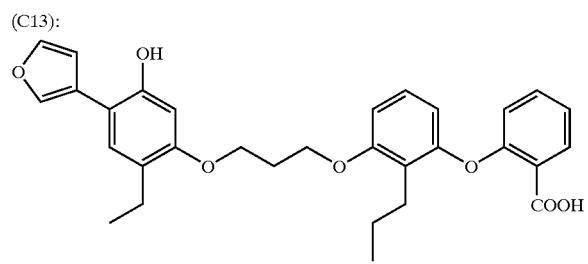
(C19):
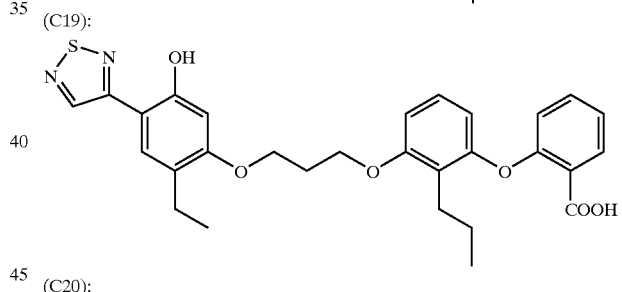
(C14):
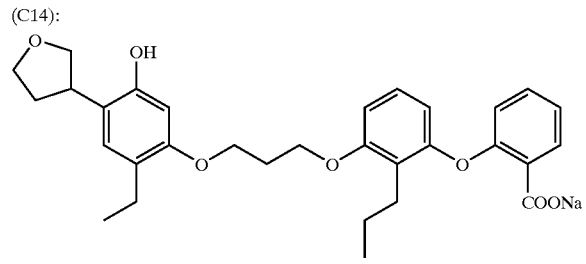
(C20):
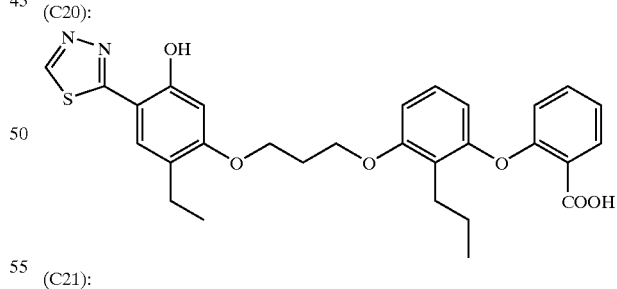
(C15):
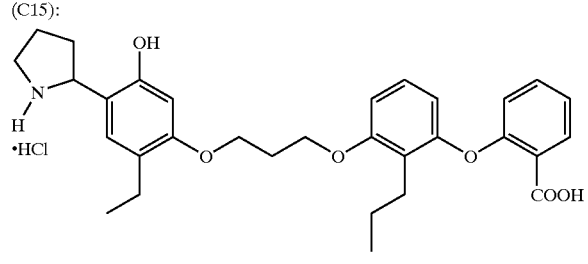
(C21):
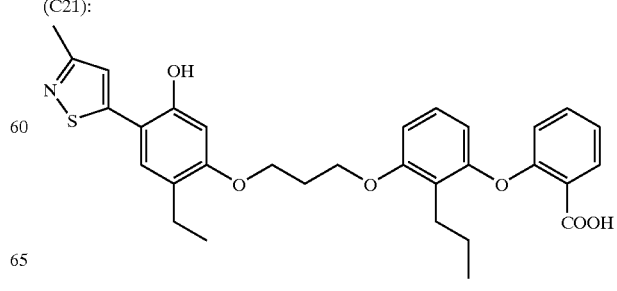

(C22):
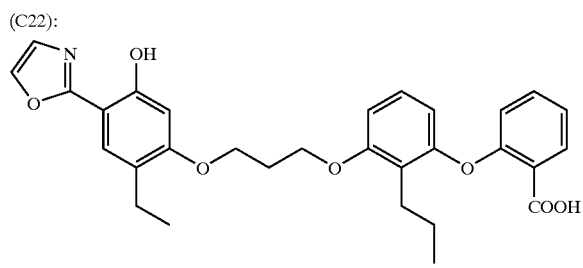

(C23):
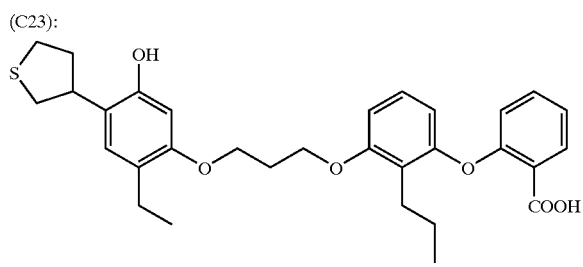

and all acid, salt, solvate and prodrug derivatives thereof.

III S. Highly Preferred Compounds of the Invention are as follows:

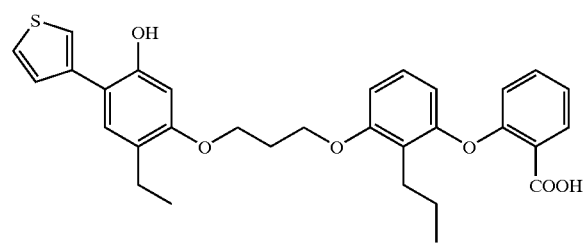

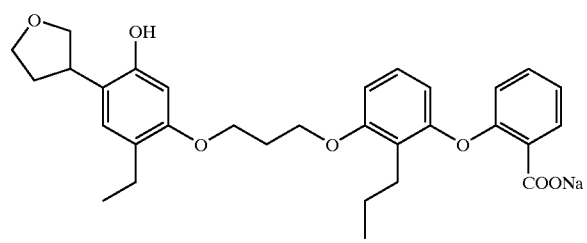

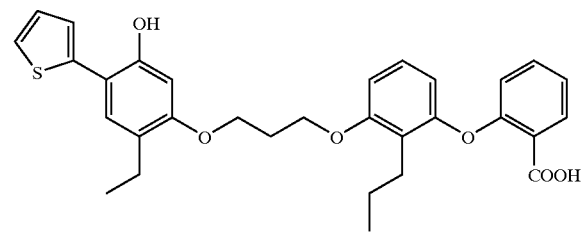

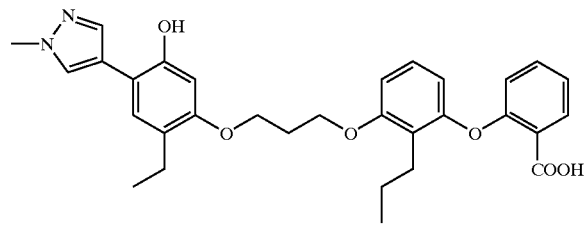

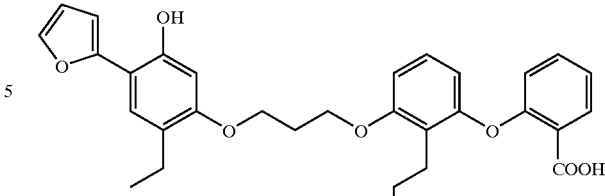

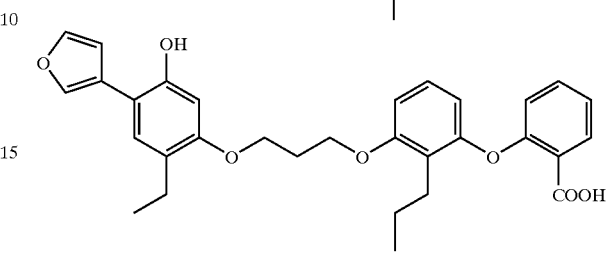

and all acid, salt, solvate and prodrug derivatives thereof.

The salts of the above diphenyl $LTB_4$ antagonists of the invention, represented by formulae (I) and (II) and the specific compounds set out by structural formulae in sections IIIR and IIIS herein, are an additional aspect of the invention. The compounds of the invention possess an Acidic Group(s) and at these sites various salts may be formed which are more water soluble and/or physiologically suitable than the parent compound in its acid form. Representative pharmaceutically acceptable salts, include but are not limited to, the alkali and alkaline earth salts such as lithium, sodium, potassium, calcium, magnesium, aluminum and the like. Sodium salts are particularly preferred. Salts are conveniently prepared from the free acid by treating the acid form in solution with a base or by exposing the acid to an ion exchange resin. For example, the (Acidic Group) of the Z of Formula (I) may be selected as —$CO_2H$ and salts may be formed by reaction with appropriate bases (e.g., NaOH, KOH) to yield the corresponding sodium or potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the $LTB_4$ antagonist compounds of this invention (see, for example, S. M. Berge, et al., "Pharmaceutical Salts," *J. Phar. Sci.*, 66: 1–19 (1977)).

Certain compounds of the invention may possess one or more chiral centers and may thus exist in optically active forms. All such stereoisomers as well as the mixtures thereof are intended to be included in the invention. If a particular stereoisomer is desired, it can be prepared by methods well known in the art, for example, by using stereospecific reactions with starting materials which contain the asymmetric centers and are already resolved or, alternatively, by methods which lead to mixtures of the stereoisomers and subsequent resolution by known methods. For example, a racemic mixture may be reacted with a single enantiomer of some other compound. This changes the racemic form into a mixture of diastereomers. Then, because the diastereomers have different melting points, different boiling points, and different solubilities, they can be separated by conventional means, such as crystallization.

Prodrugs are derivatives of the compounds of Formula (I) and (II), supra., which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

Esters of carboxylic acids are preferred prodrugs of the compounds of the invention (viz., the compounds of Formula I, Formula II and the specific compounds set out in Section IIIR and IIIS, herein).

Methyl ester prodrugs may be prepared by reaction of the acid form of a compound of formula (I) in a medium such as methanol with an acid or base esterification catalyst (e.g., NaOH, $H_2SO_4$). Ethyl ester prodrugs are prepared in similar fashion using ethanol in place of methanol.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula (I) (in a medium such as dimethylformamide) 4-(2-chloroethyl) morpholine hydrochloride (available from Aldrich Chemical Co., Milwaukee, Wis. USA, Item No. C4,220-3).

Preferred compounds of the invention are compounds of Formula (I), or Formula (II) or the specific compounds of sections IIIR and IIIS shown above by structural formula; wherein the acid, salt and prodrug derivatives thereof are respectively selected from: carboxylic acid, sodium salt, and ester prodrug.

IV. Method of Making the Compounds of the Invention

General reaction schemes (not represented to be specific Examples) applicable for synthesis of the $LTB_4$ antagonist compounds represented by formula (I) are set out below. Numerous literature references and Chemical Abstract registry numbers (e.g., RN 152609-60-4) are supplied as additional aids for preparing reagents used in practicing the synthesis schemes of the invention.

REACTION SCHEMES FOR MAKING THE COMPOUNDS OF THE INVENTION

The following scheme illustrates a process for making Example (1), a 4-substituted oxazole $LTB_4$ receptor antagonist:

Scheme 1

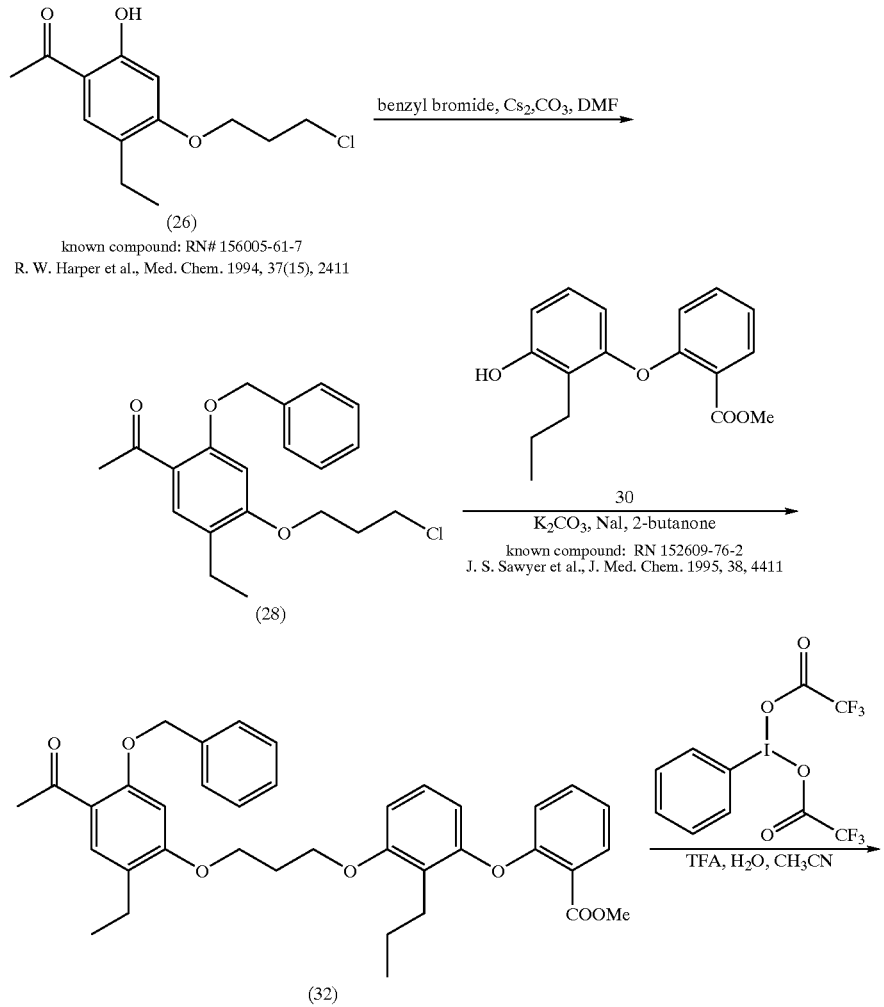

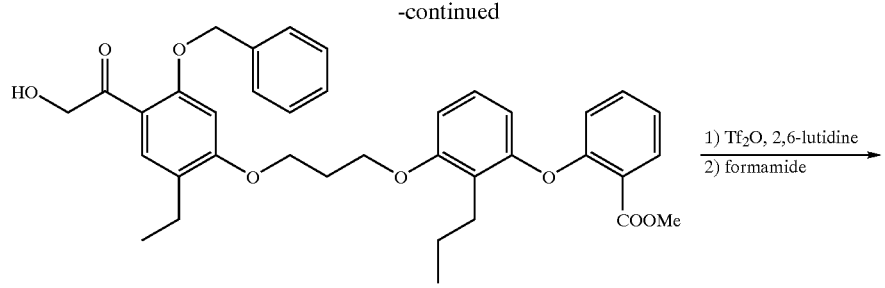

(34)

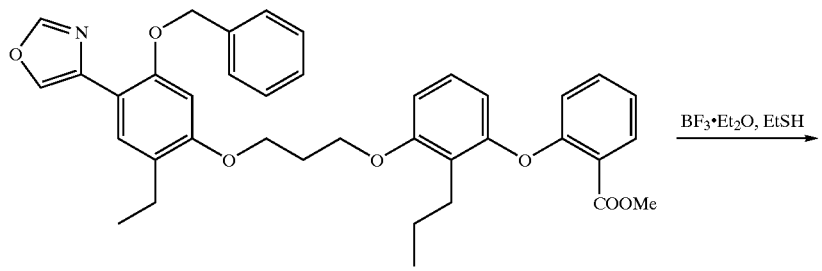

(36)

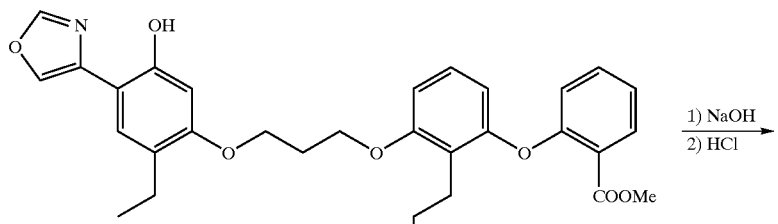

(38)

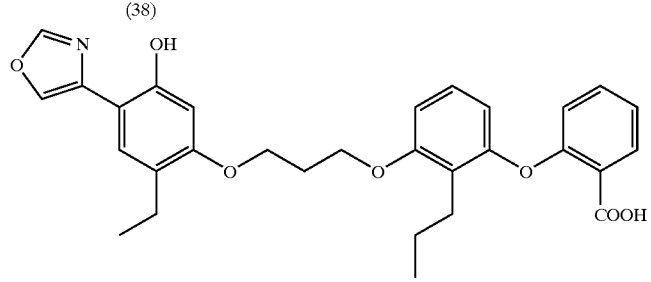

(1)

Known chloride (26) may be alkylated with benzyl bromide to provide chloride (28). Reaction with known ester (30), catalyzed by a suitable base, provides acetophenone (32). Oxidation with bis(trifluoroacetoxy)iodobenzene gives alphahydroxy ketone (34), that may be cyclized with triflic anhydride and formamide to give the 4-substituted oxazole (36). Debenzylation with boron trifluoride etherate and ethanethiol gives oxazole (38), that is hydrolyzed and protonated to provide Example (1).

Scheme 2

The following scheme illustrates a process for making Example (2), a 5(4)-substituted imidazole $LTB_4$ receptor antagonist:

Scheme 2

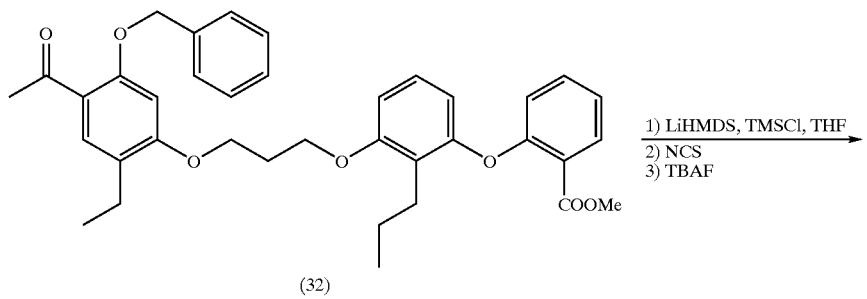

(32)

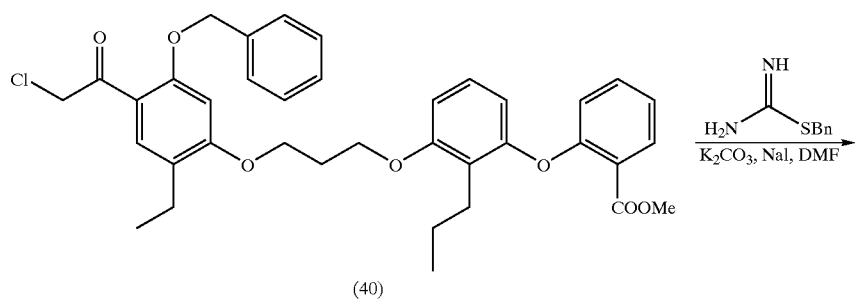

(40)

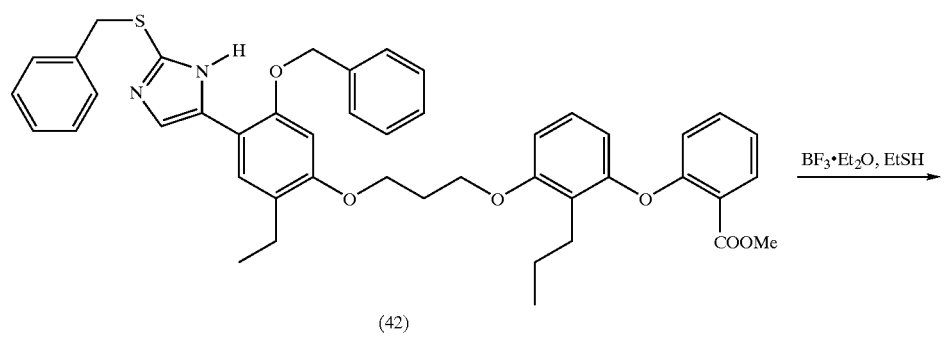

(42)

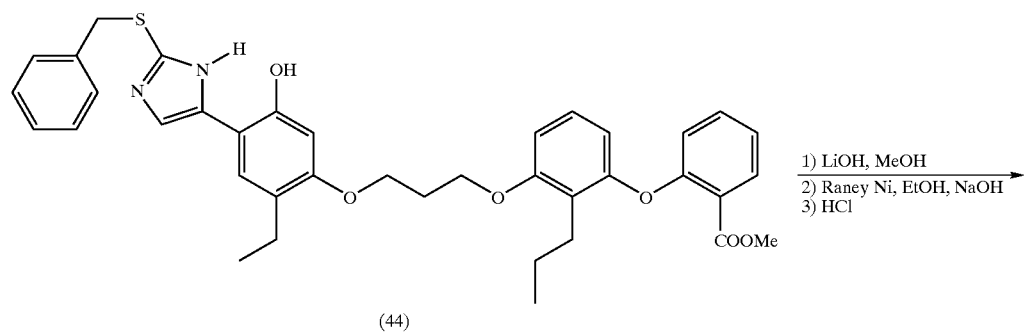

(44)

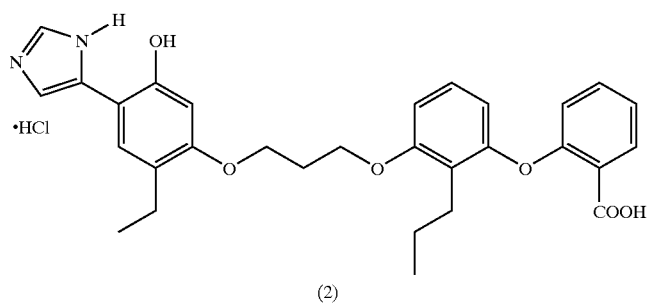

(2)

The trimethylsilyl enol ether of acetophenone (32) is formed and treated with N-chlorosuccinimide followed by tetra-n-butylammonium fluoride to provide the chloroketone (40). Treatment of (40) with 2-benzyl-2-thiopseudourea and base provides imidazole (42), that is treated with boron trifluoride etherate and ethanethiol to give imidazole (44). Hydrolysis and protonation provide Example (2) as the hydrochloride salt.

Scheme 3
The following scheme illustrates a process for making Example (3), a 4-substituted thiazole LTB$_4$ receptor antagonist:
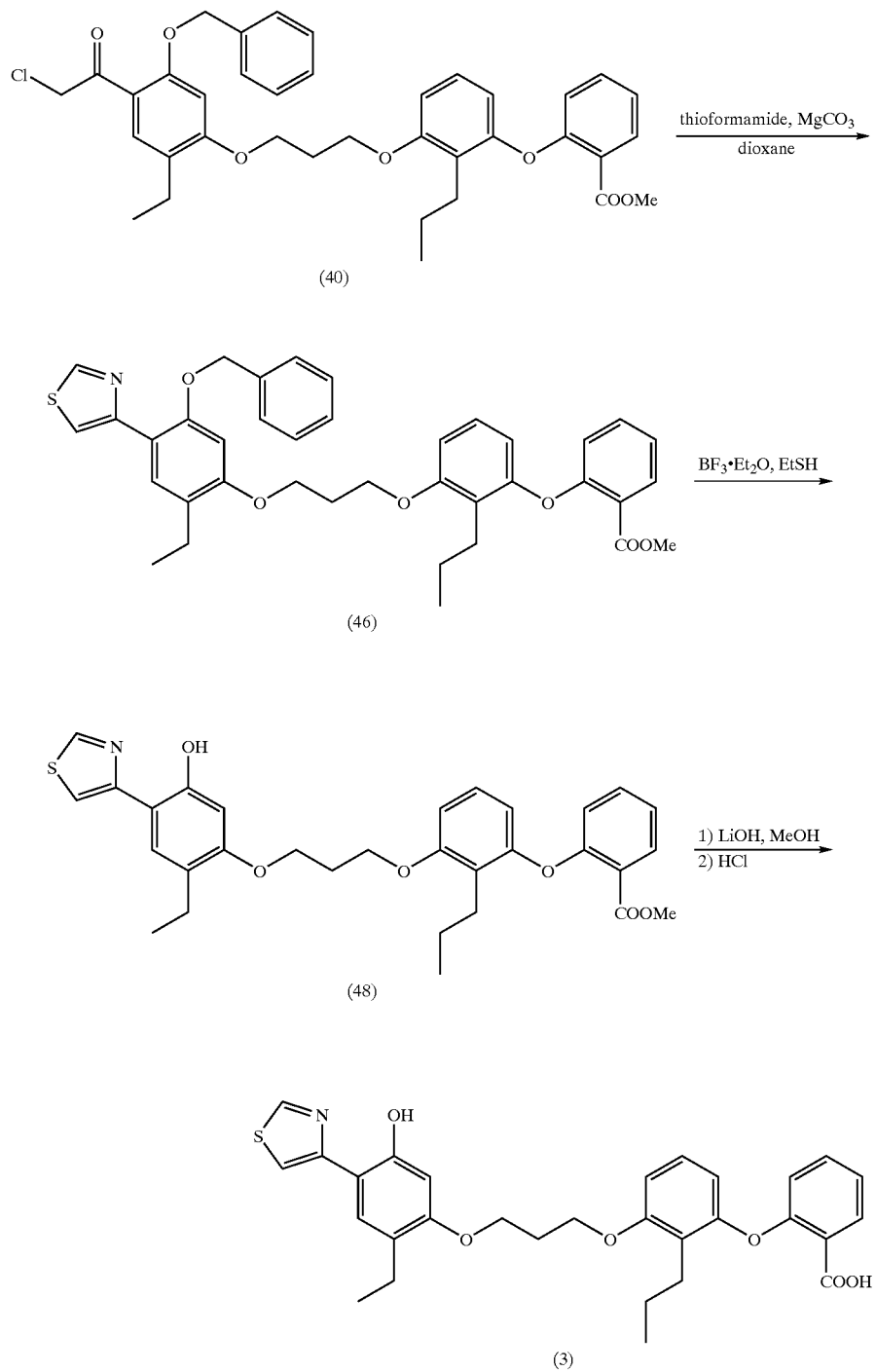
Chloroketone (40) is treated with thioformamide and magnesium carbonate to give thiazole (46), that is debenzylated with boron trifluoride etherate and ethanethiol giving thiazole (48). Hydrolysis and protonation provides Example (3).

Scheme 4

The following scheme illustrates a process for making Example (4), a 5(3)-substituted pyrazole LTB$_4$ receptor antagonist:

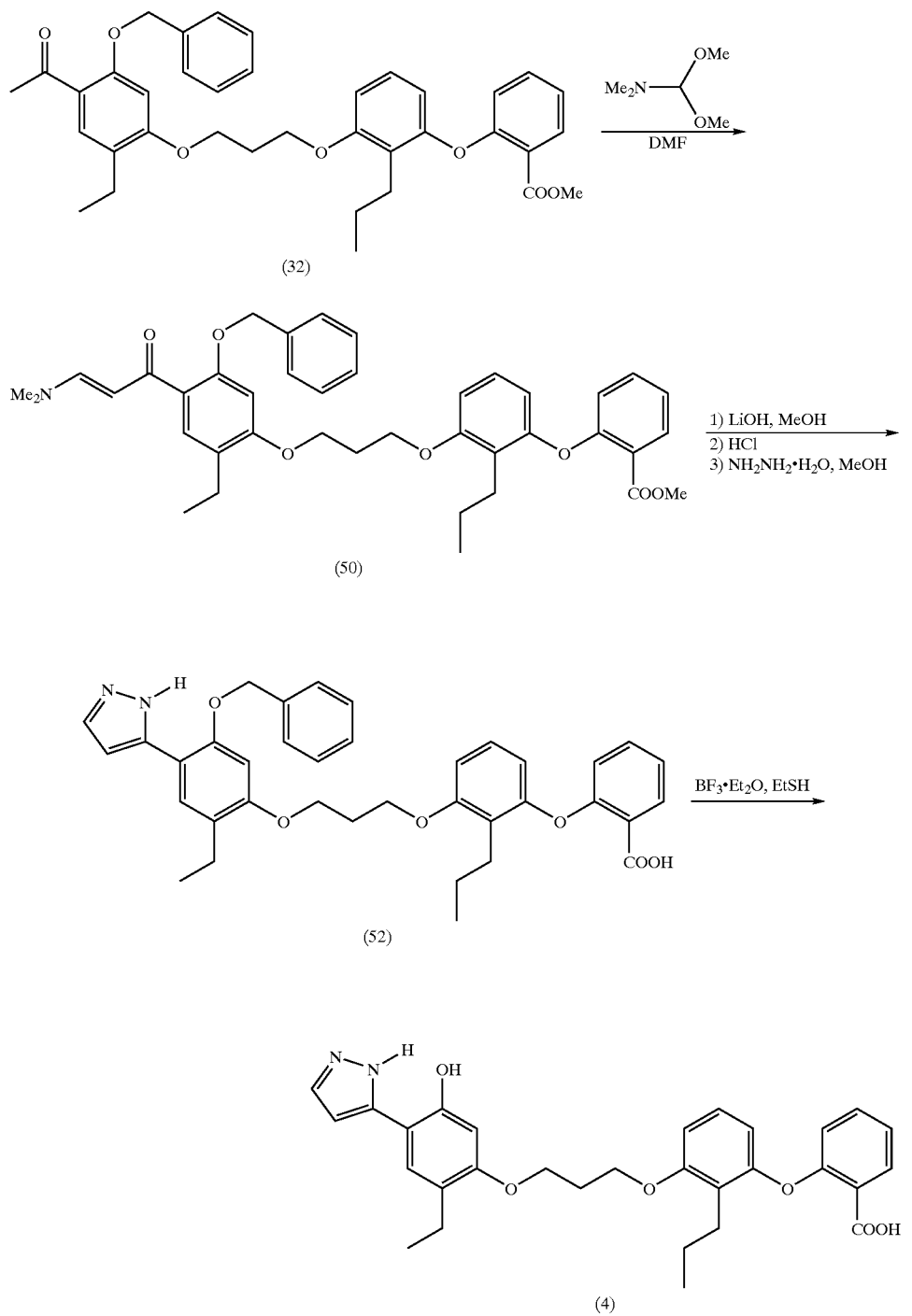

Treatment of acetophenone (32) with N,N-dimethylformamide dimethyl acetal gives enone (50), that may be hydrolyzed, protonated, and then heated with hydrazine hydrate to provide pyrazole (52). Debenzylation of the resulting pyrazole with boron trifluoride etherate and ethanethiol gives Example (4).

Scheme 5
The following scheme illustrates a process for making Example (5), a 5-substituted isoxazole LTB$_4$ receptor antagonist:
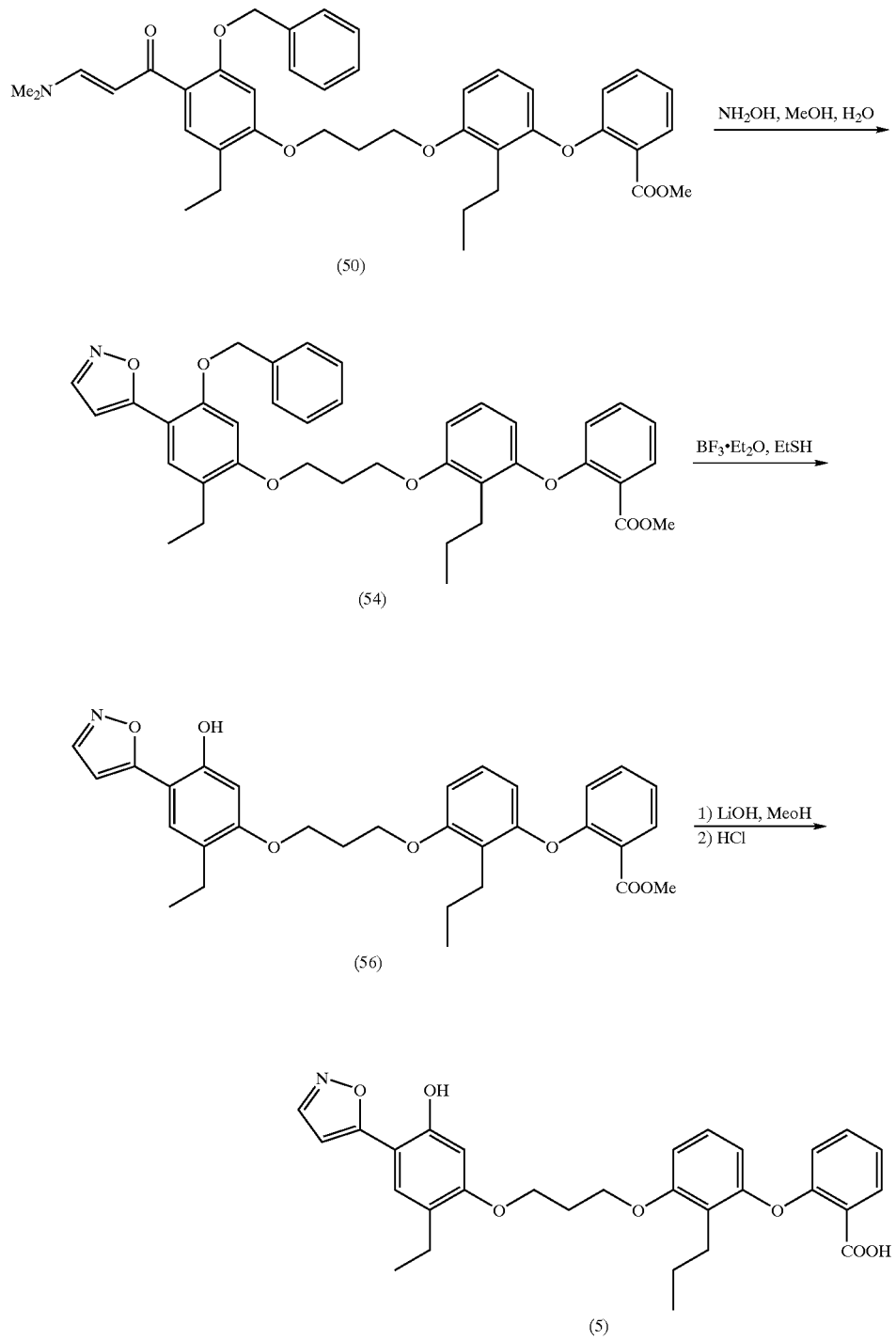
Treatment of enone (50) with hydroxylamine provides isoxazole (54), that is debenzylated with boron trifluoride etherate and ethanethiol to give isoxazole (56). Hydrolysis and protonation provides Example (5).

Scheme 6
The following scheme illustrates a process for making Example (6), a 5(4)-substituted 1,2,3-triazole LTB$_4$ receptor antagonist:
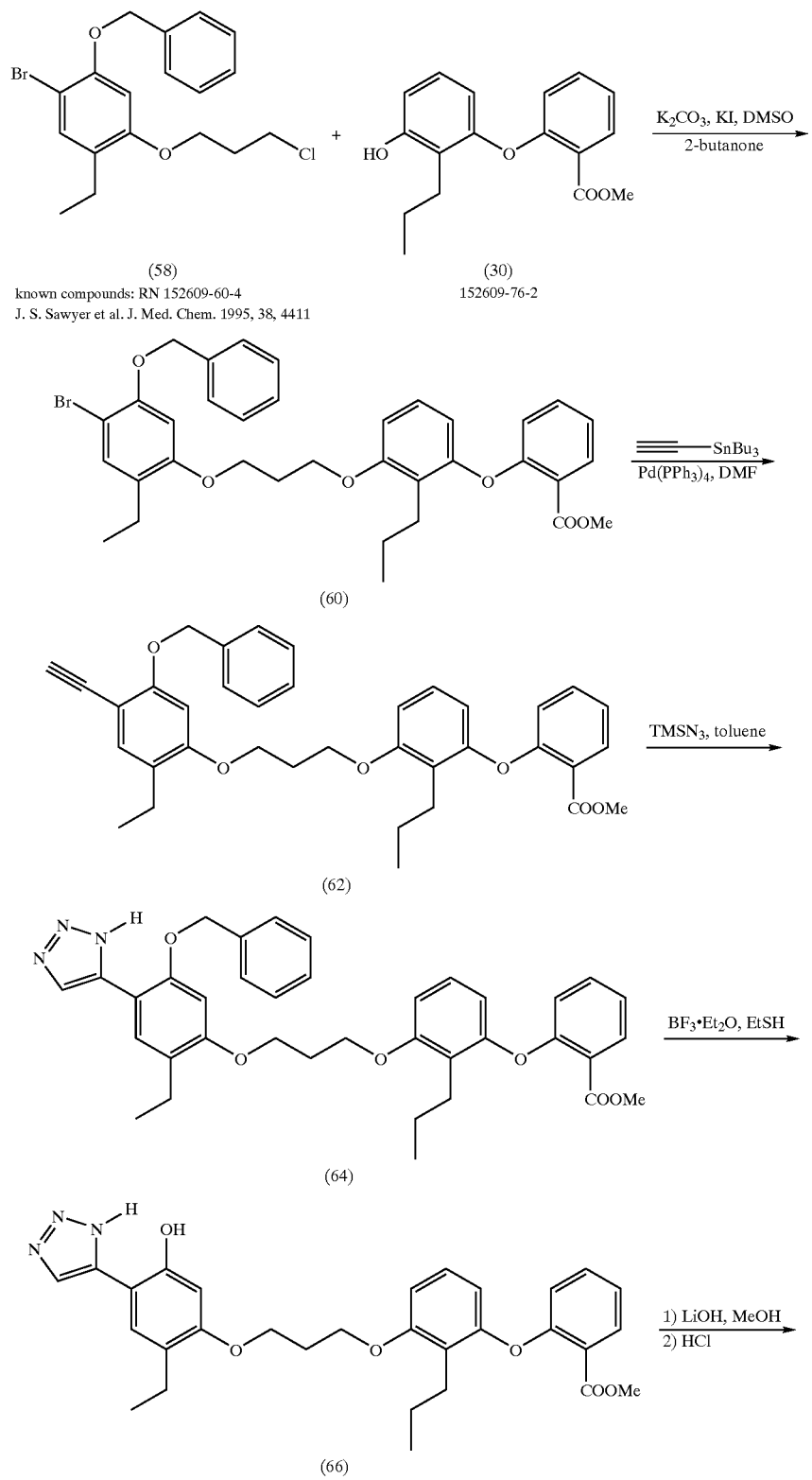

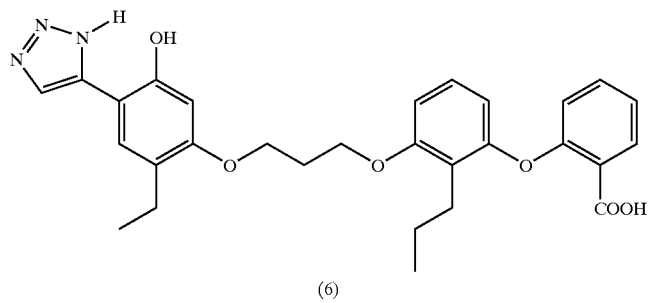

(6)

Known phenol (30) is alkylated with known chloride (58) to give aryl bromide (60). Treatment of (60) with tri-n-butylethynyltin and a palladium catalyst gives alkyne (62). Heating (62) with trimethylsilyl azide provides triazole (64), that is debenzylated with boron trifluoride etherate and ethanethiol to give triazole (66). Hydrolysis and protonation provides Example (6).

Scheme 7

The following scheme illustrates a process for making Example (7), a 1-substituted pyrrole $LTB_4$ receptor antagonist:

Scheme 7

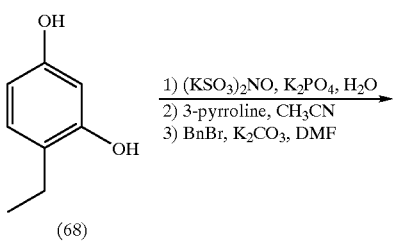

(68)

1) $(KSO_3)_2NO$, $K_2PO_4$, $H_2O$
2) 3-pyrroline, $CH_3CN$
3) BnBr, $K_2CO_3$, DMF

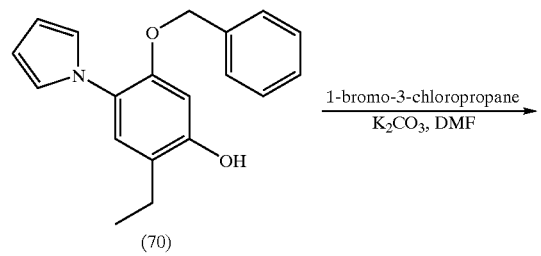

(70)

1-bromo-3-chloropropane
$K_2CO_3$, DMF

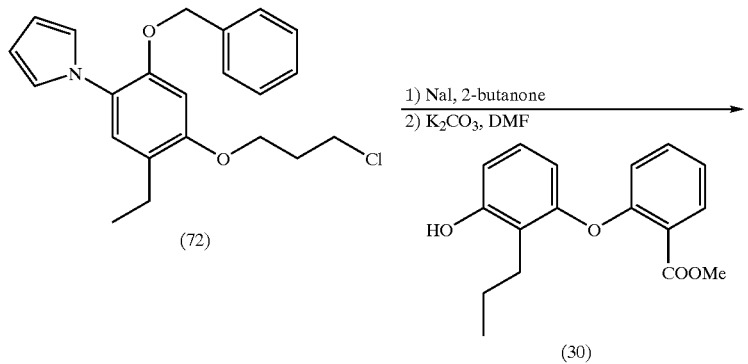

(72)

1) NaI, 2-butanone
2) $K_2CO_3$, DMF (30)

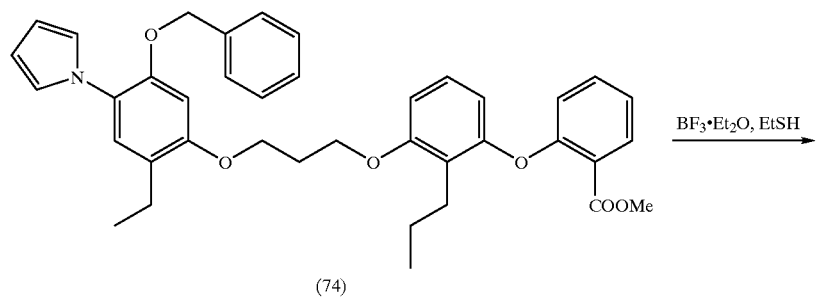

(74)

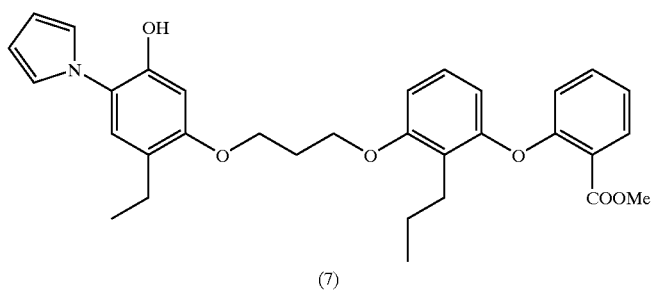

(7)

References for formation of 1-aryl substituted pyrroles: M. Mure and J. P. Kilnman, J. Am. Chem. Soc. 1995, 117(34), 8698; Y. Lee et al. J. Am. Chem. Soc. 1996, 118(30), 7241

4-Ethylbenzene-1,3-diol (68) is treated with potassium nitrosodisulfonate followed by 3-pyrroline and benzylbromide and a base to provide pyrrole (70). Alkylation with 1-bromo-3-chloropropane gives chloride (72), that is used to alkylate phenol (30) to give pyrrole (74). Debenzylation with boron trifluoride etherate and ethanethiol provides Example (7).

Scheme 8

The following scheme illustrates a process for making Example (8), a 5-substituted 1,2,4-thiadiazole $LTB_4$ receptor antagonist:

Scheme 8

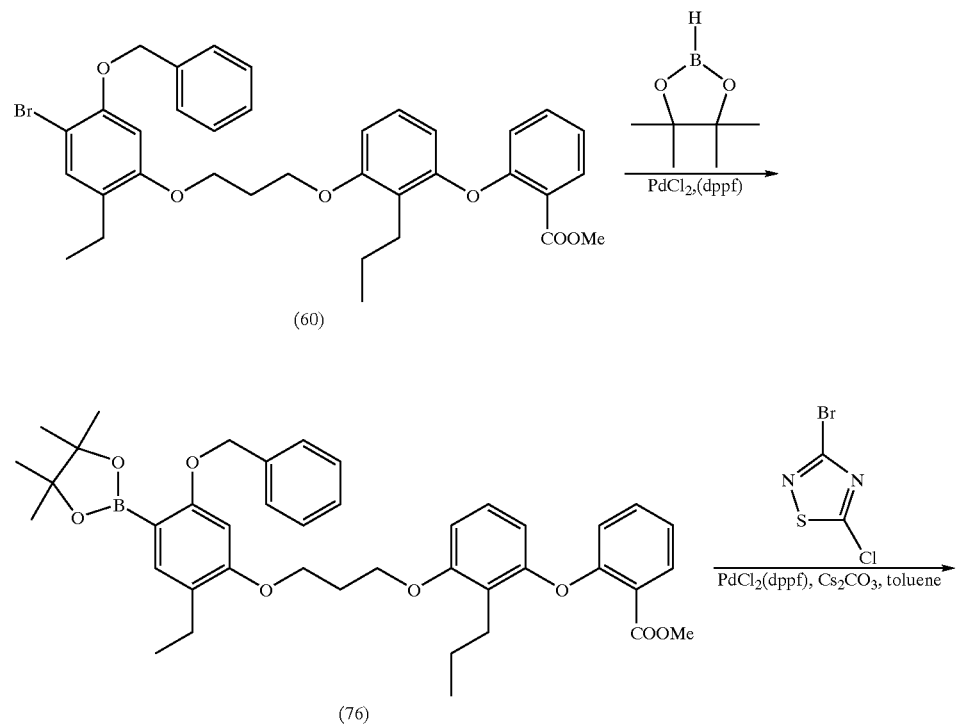

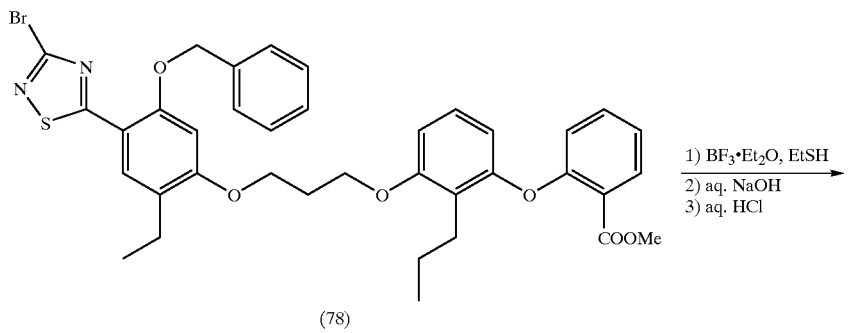

(78)

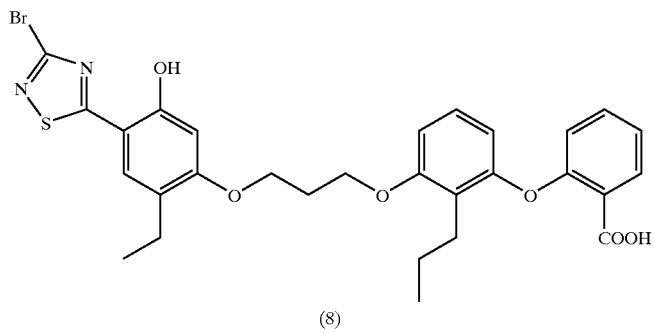

(8)

The palladium-catalyzed addition of 4,4,5,5-tetramethyl-[1,3,2]dioxaborolane to bromide (60) gives boronic ester (76). The palladium-catalyzed addition of 3-bromo-5-chloro-1,2,4-thiadiazole to (76) gives ester (78). Debenzylation with boron trifluoride etherate and ethanethiol, followed by hydrolysis and protonation, gives Example (8).

Scheme 9

The following scheme illustrates a process for making Example (9), a 2-substituted thiophene $LTB_4$ receptor antagonist:

Scheme 9

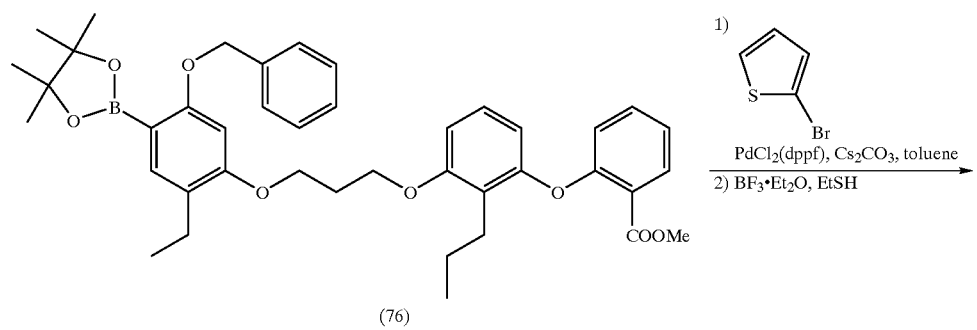

(76)

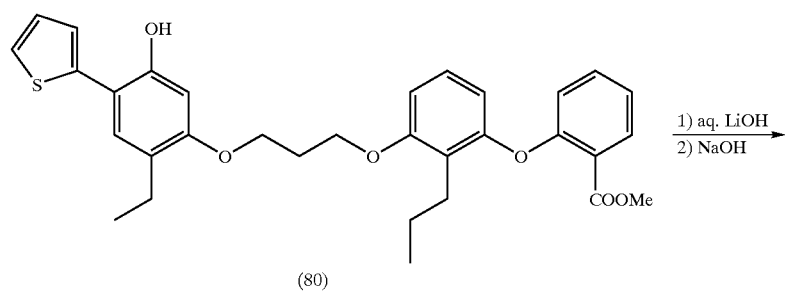

(80)

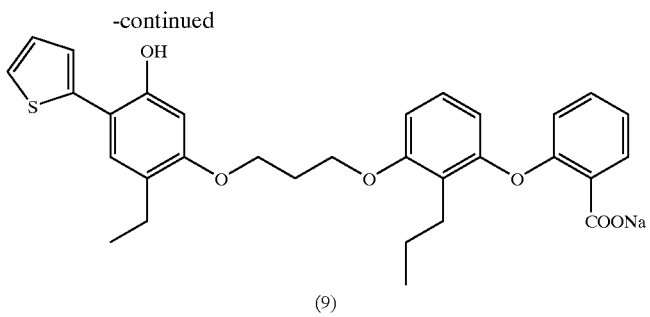

(9)

The palladium-catalyzed addition of boronic ester (76) to 2-bromothiophene, followed by debenzylation with boron trifluoride etherate and ethanethiol, provides thiophene (80). Hydrolysis and salt formation provides Example (9).

Scheme 10

The following scheme illustrates a process for making Example (10), a 4-substituted pyrazole LTB$_4$ receptor antagonist:

Scheme 10

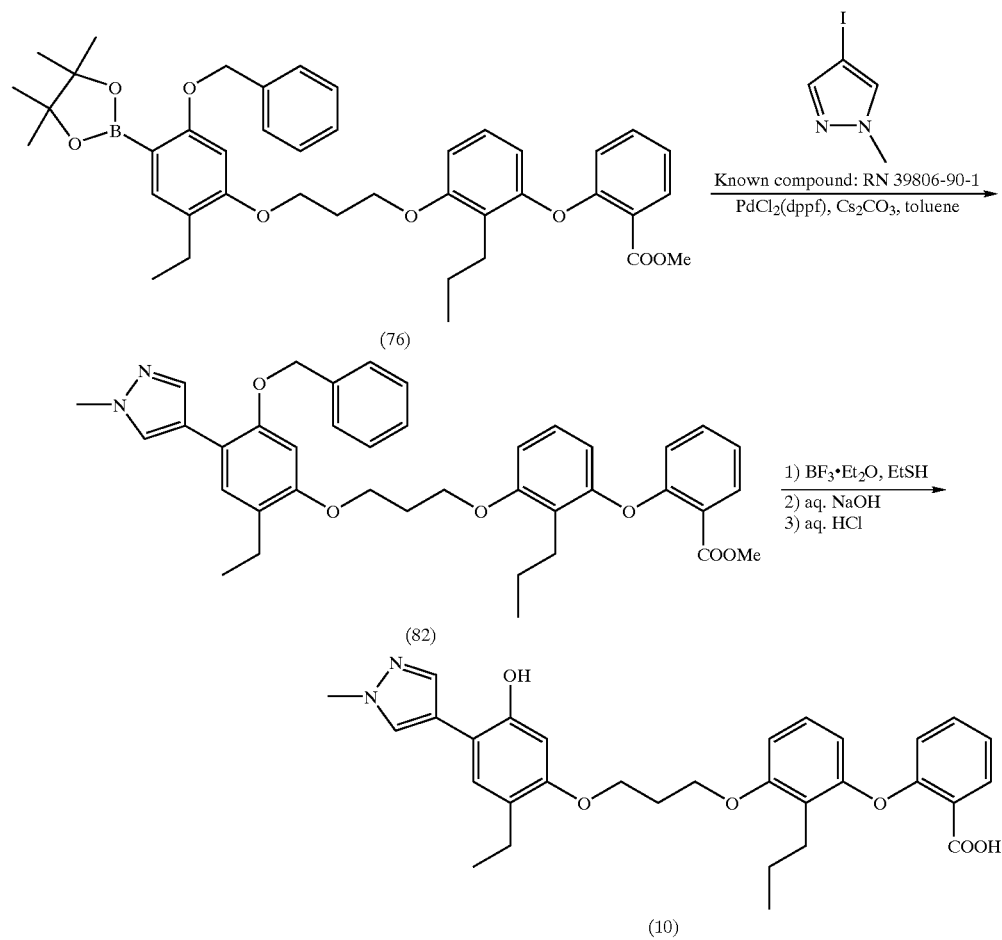

The palladium-catalyzed addition of boronic ester (76) to 1-methyl-4-iodopyrazole provides pyrazole (82). Debenzylation with boron trifluoride etherate and ethanethiol, followed by hydrolysis and protonation, provides Example (10).

Scheme 11
The following scheme illustrates a process for making Example (11), a 2-substituted thiazole LTB$_4$ receptor antagonist:
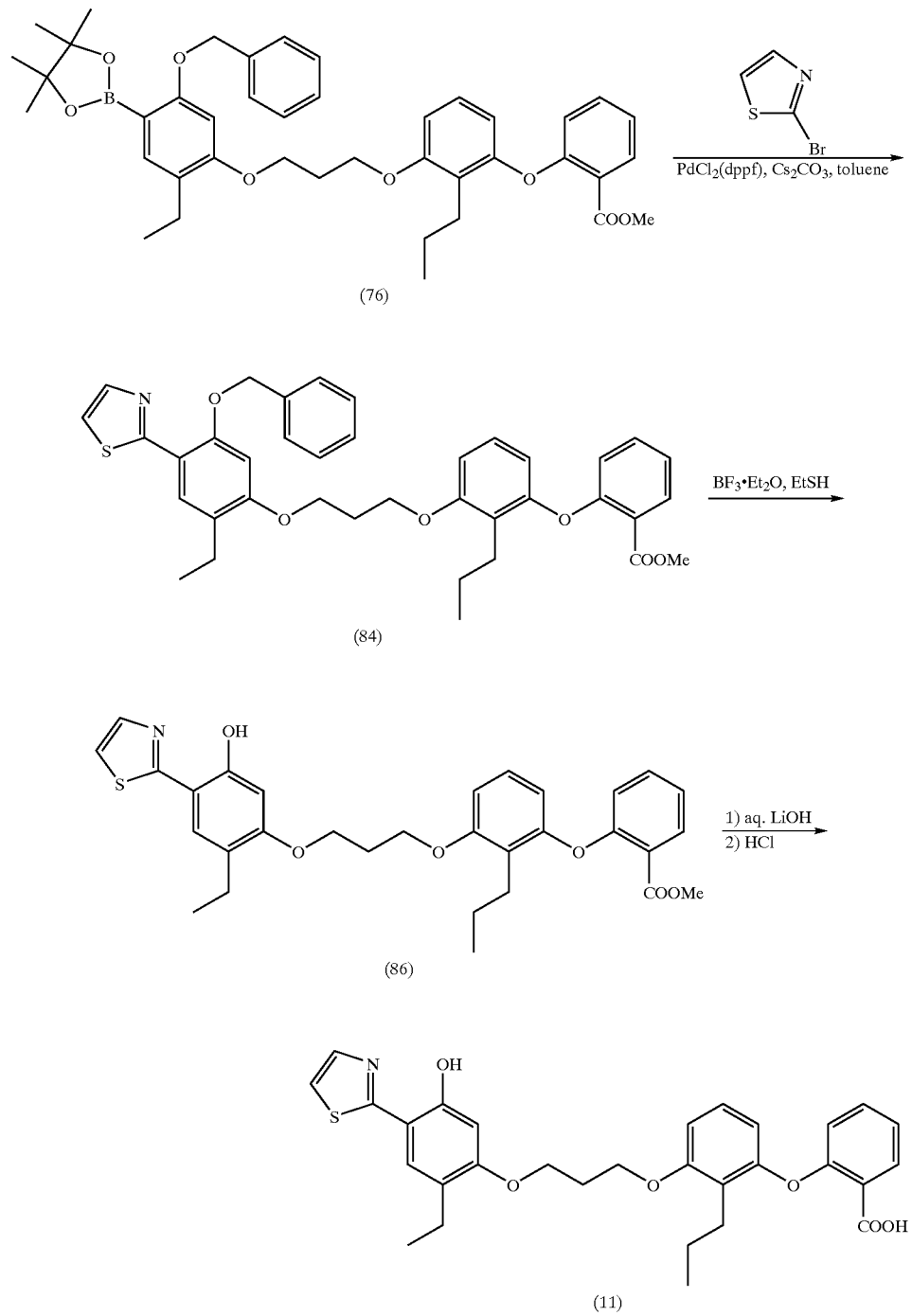
The palladium-catalyzed addition of boronic ester (76) to 2-bromothizaole provides thiazole (84). Debenzylation with boron trifluoride etherate and ethanethiol gives thiazole (86). Hydrolysis and protonation provides Example (11).

Scheme 12

The following scheme illustrates a process for making Example (12), a 4-substituted isoxazole LTB$_4$ receptor antagonist:

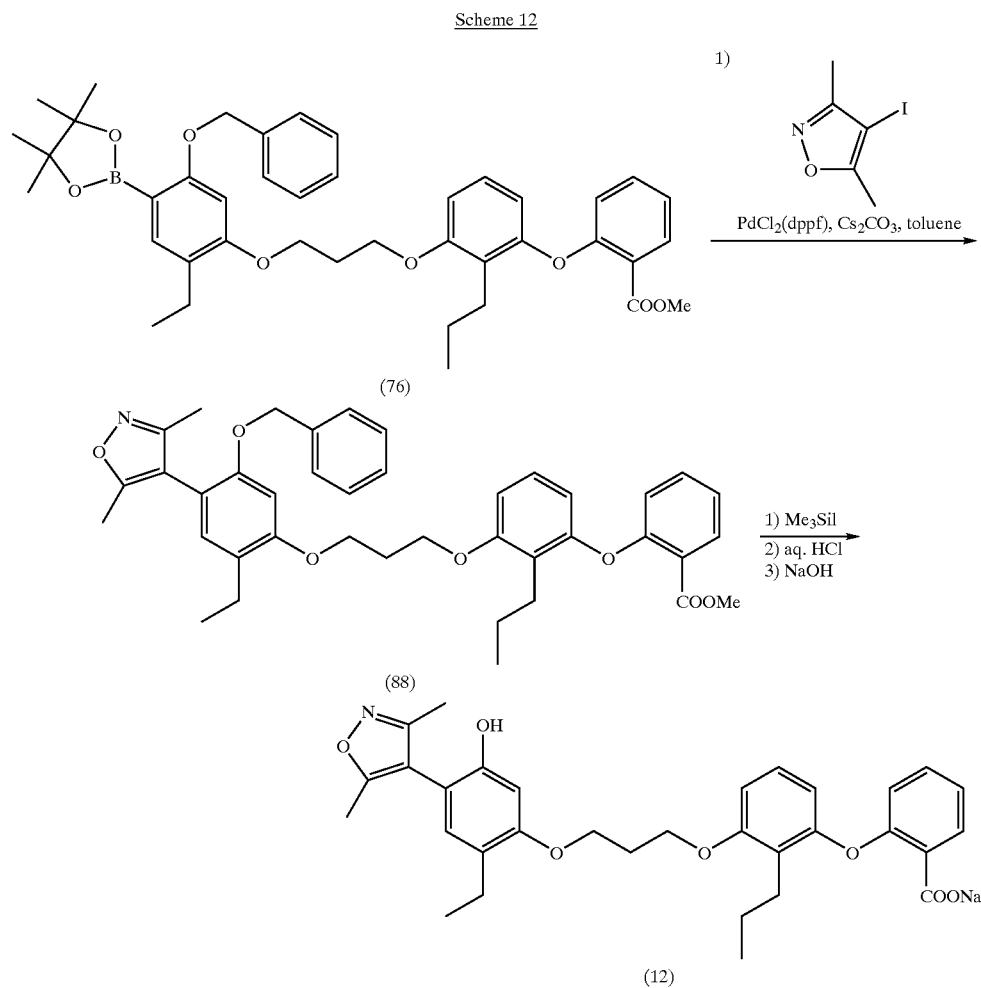

The palladium-catalyzed addition of boronic ester (76) to 3,5-dimethyl-4-iodoisoxazole provides oxazole (88). Debenzylation with trimethylsilyl iodide, followed by hydrolysis and salt formation, provides Example (12).

Scheme 13

The following scheme illustrates a process for making Example (13), a 2-substituted furan LTB$_4$ receptor antagonist:

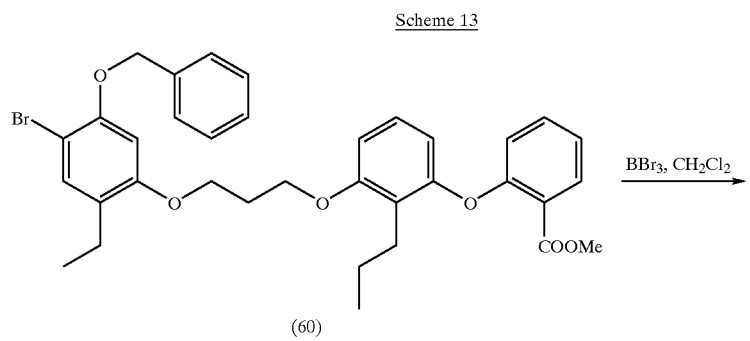

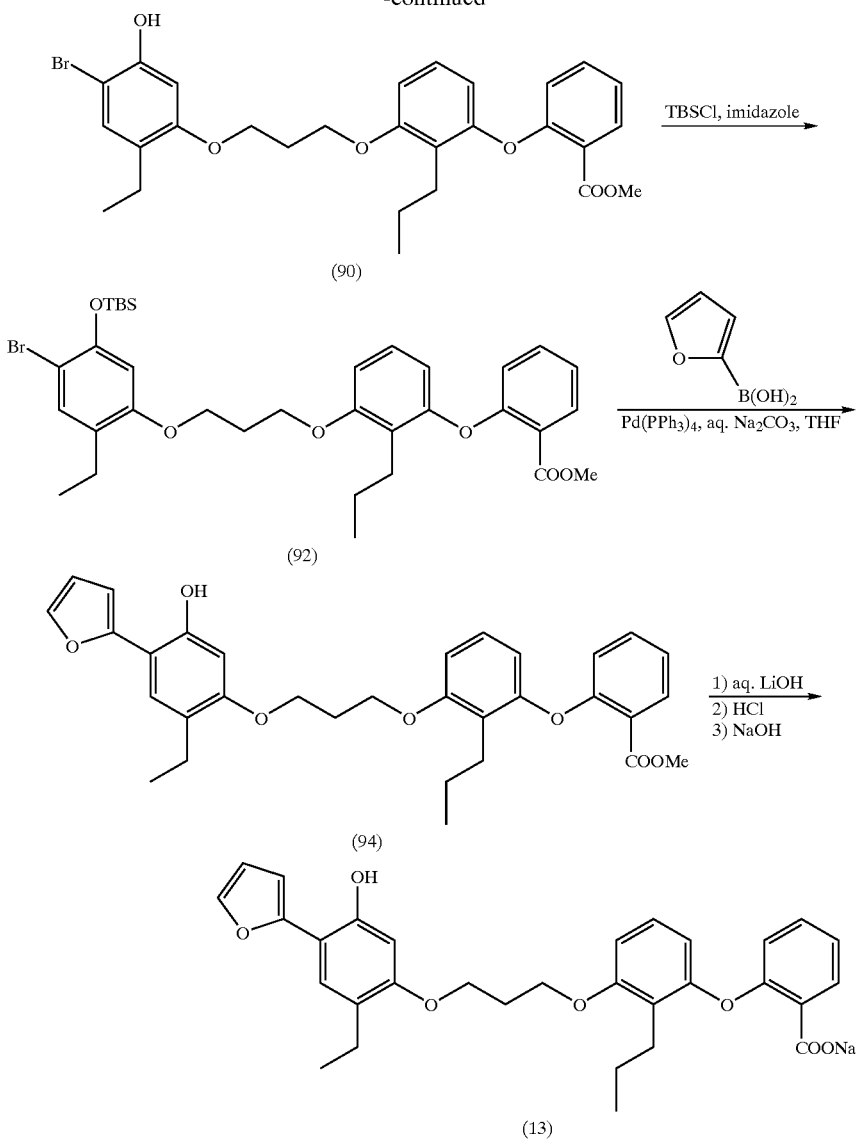

Debenzylation of bromide (60) with boron tribromide provides phenol (90), that is treated with tert-butyldimethylsilyl chloride and imidazole to give silyl ether (92). The palladium-catalyzed addition of (92) to furan-2-boronic acid provides furan (94). Hydrolysis and salt formation gives Example (13).

Scheme 14

The following scheme illustrates a process for making Example (14), a 3-substituted furan $LTB_4$ receptor antagonist:

Scheme 14

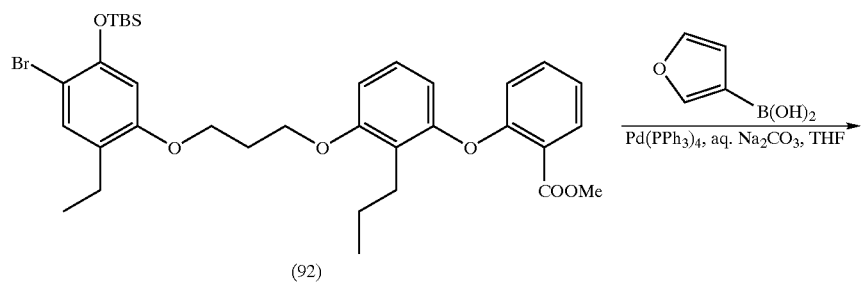

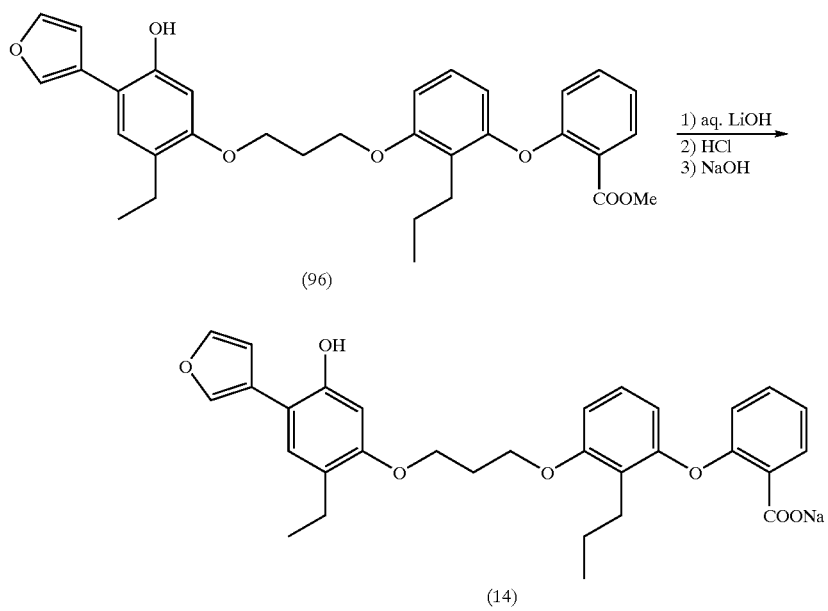
The palladium-catalyzed addition of (92) to furan-3-boronic acid provides furan (96). Hydrolysis and salt formation gives Example (14).
Scheme 15
The following scheme illustrates a process for making Example (15), a 3-substituted tetrahydrofuran $LTB_4$ receptor antagonist:
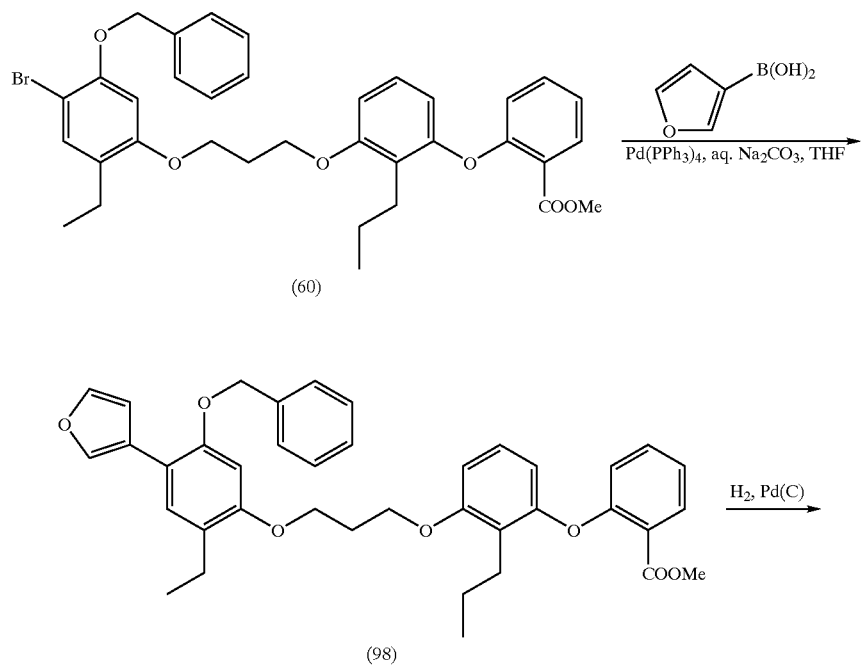

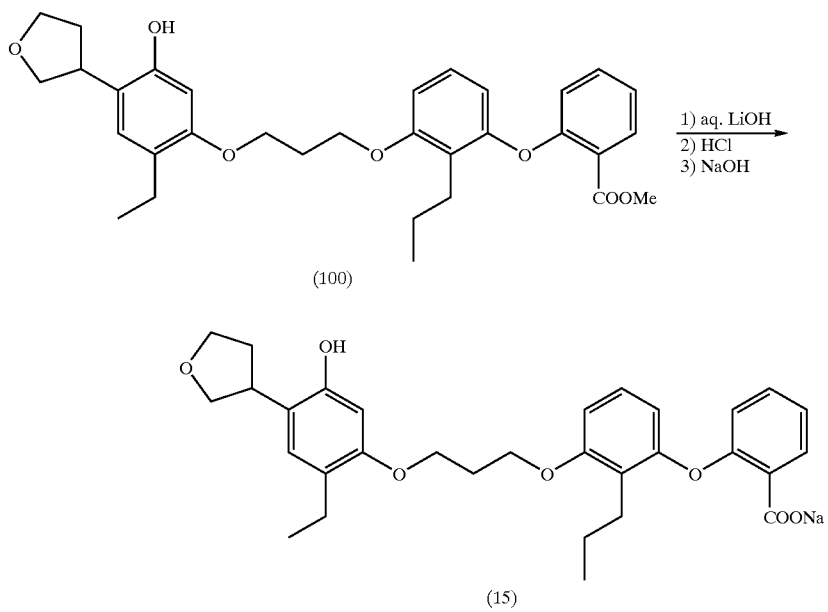
The palladium-catalyzed addition of bromide (60) to furan-3-boronic acid provides furan (98). Hydrogenation over a palladium catalyst gives tetrahydrofuran (100). Hydrolysis and salt formation gives Example (15).
Scheme 16
The following scheme illustrates a process for making Example (16), a 2-substituted pyrrolidine $LTB_4$ receptor antagonist:
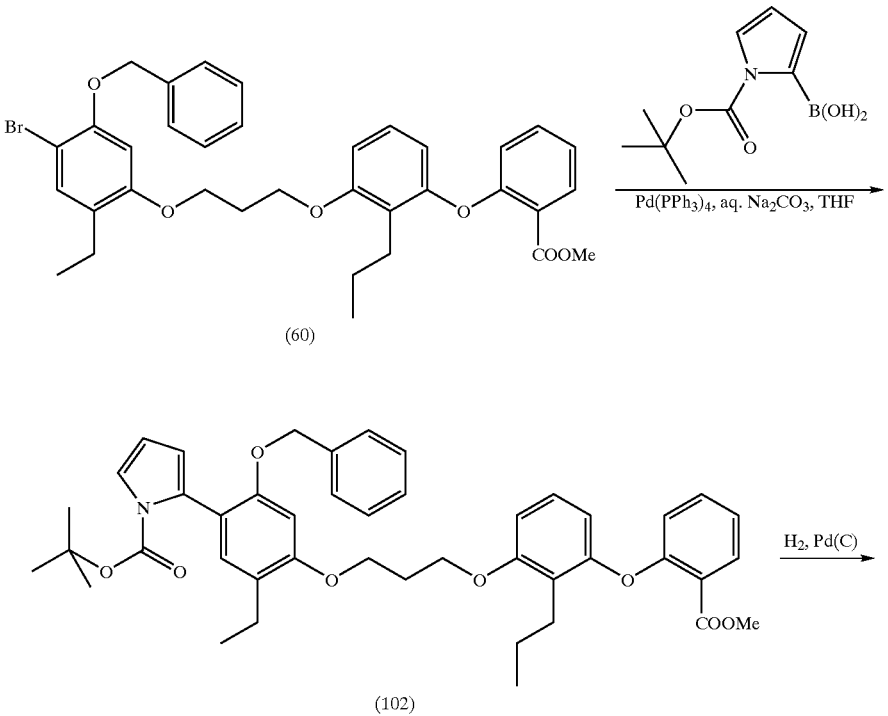

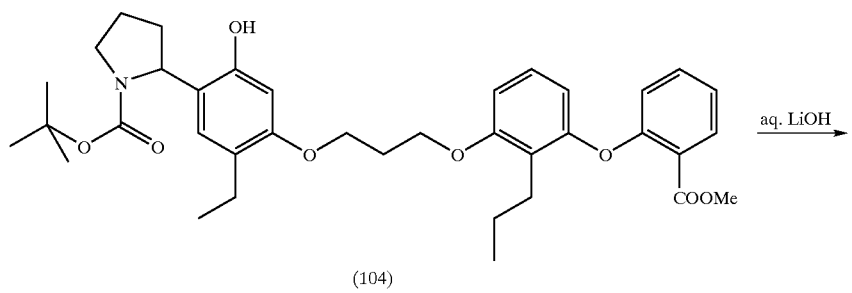

(104)

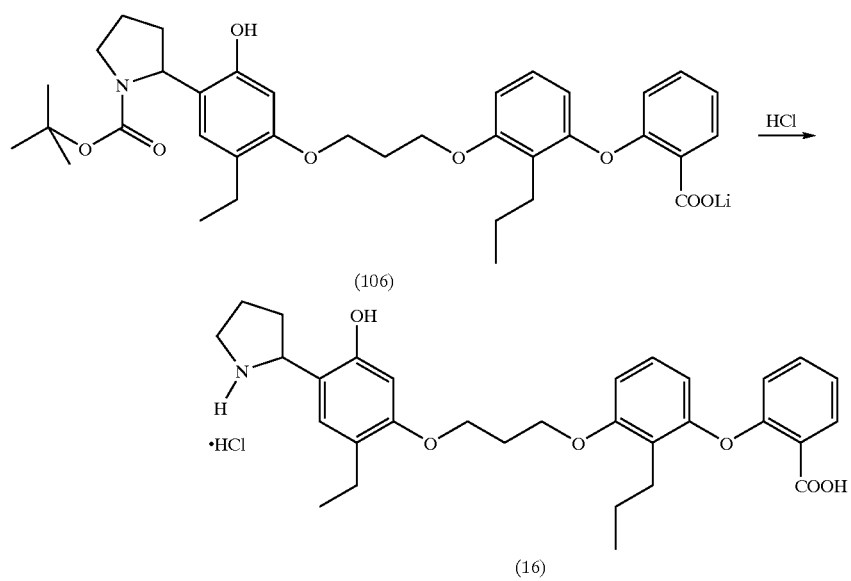

The palladium-catalyzed addition of bromide (60) to N-boc pyrrole-2-boronic acid provides pyrrole (102). Hydrogenation over a palladium catalyst gives pyrrolidine (104). Hydrolysis and salt formation gives pyrrolidine (106). Treatment with hydrochloric acid provides Example (16) as the hydrochloride salt.

Scheme 17

The following scheme illustrates a process for making Example (17), a 3-substituted thiophene LTB$_4$ receptor antagonist:

Scheme 17

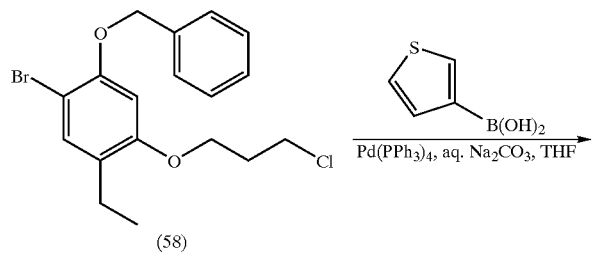

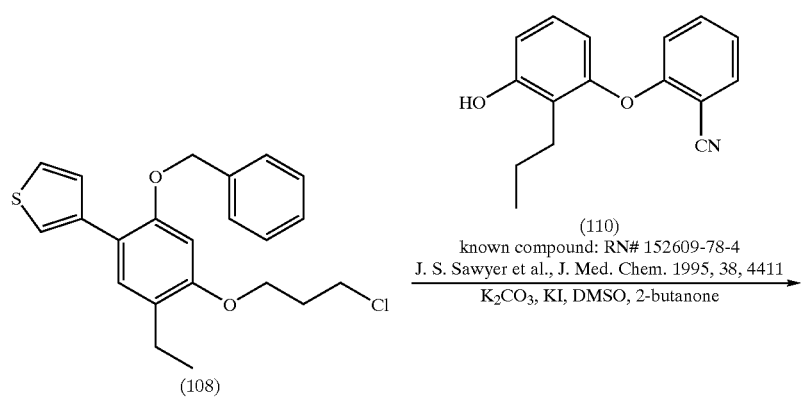
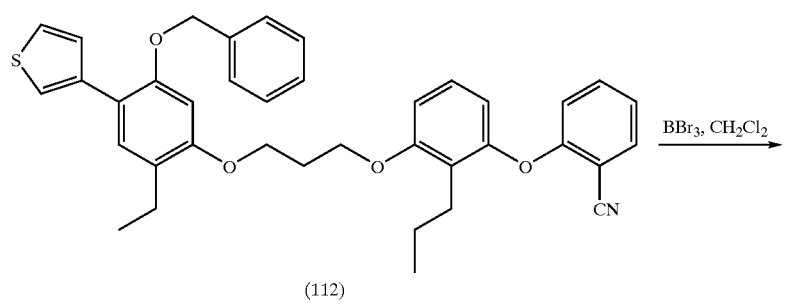
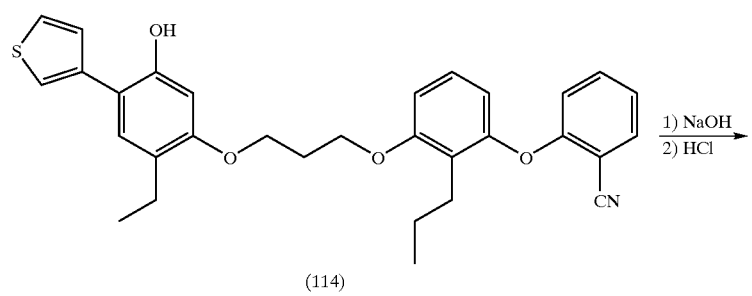
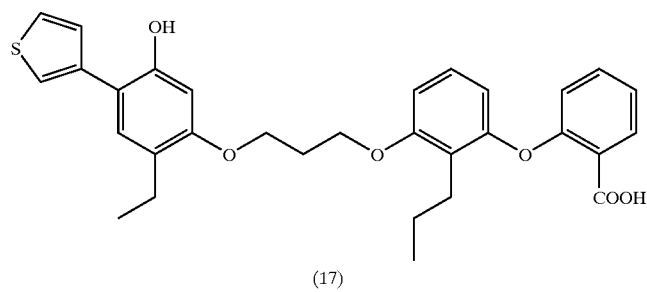
The palladium-catalyzed addition of bromide (58) to thiophene-3-boronic acid provides thiophene (108). Alkylation of known phenol (110) with (108) catalyzed by base provides thiophene (112). Debenzylation with boron tribromide gives thiophene (114). Hydrolysis and protonation provide Example (17).

Scheme 18
The following scheme illustrates a process for making Example (18), a 5-substituted 1,2,3,4-thiatriazole LTB$_4$ receptor antagonist:
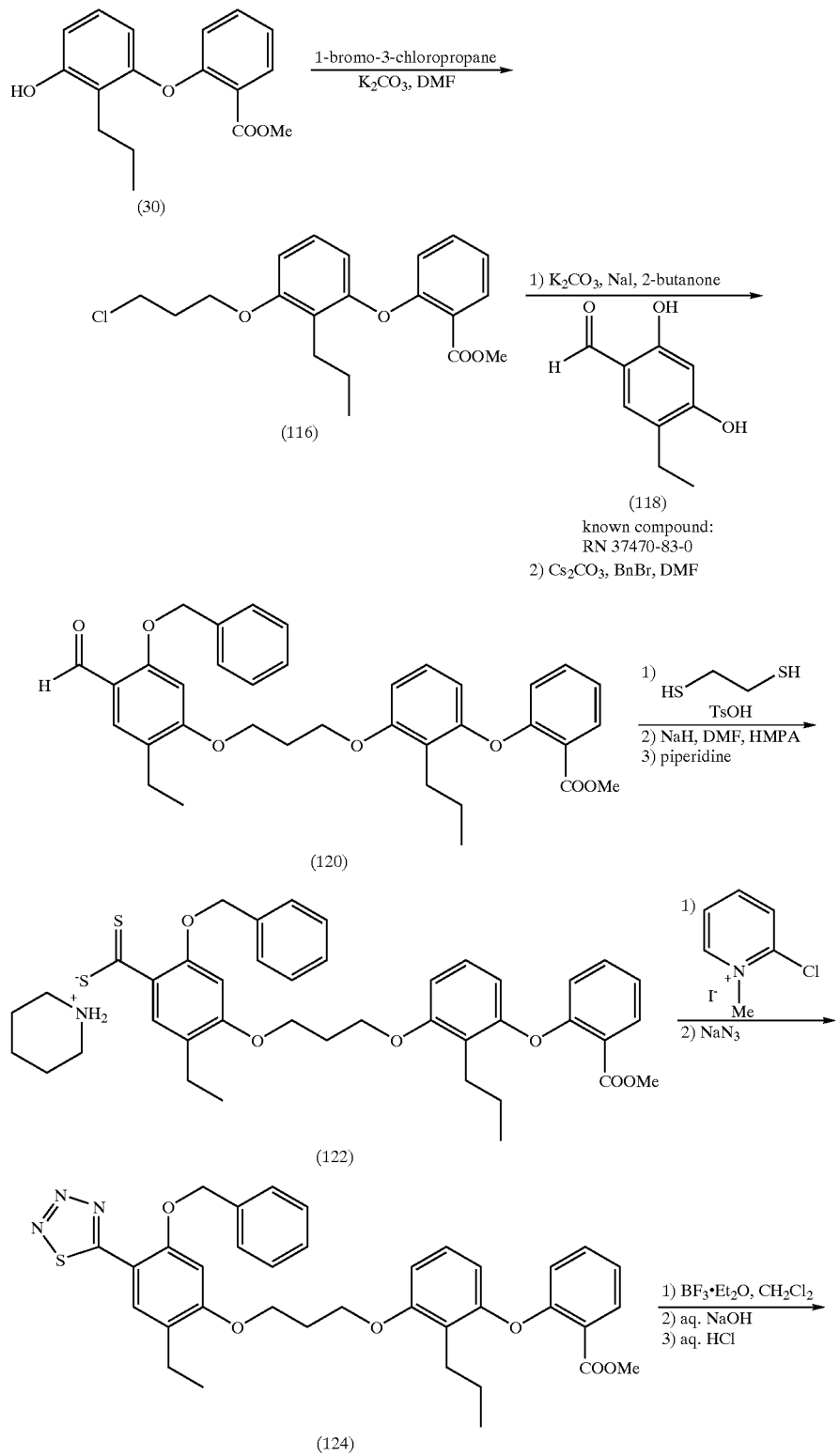

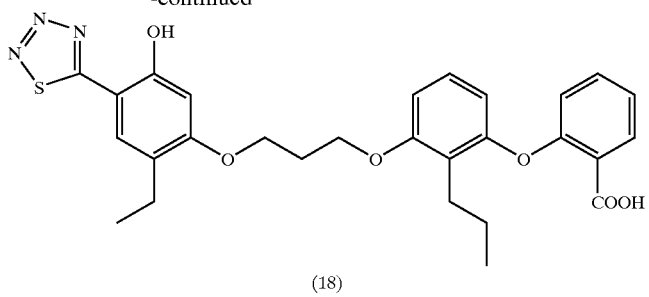

(18)

Reference for formation of dirthioacids: N. C. Gonnella et at. Syn. Comm un. 1979, 17
Reference for formation of 5-substituted 1, 2, 3, 4-thiatriazoles from d ithloacids:
S. I. Ikeda et al., Synthesis 1990, 415

Phenol (30) is alkylated with 1-bromo-3-chloropropane to give chloride (116), that is in turn to be treated with known aldehyde (118) and a base, followed by benzylation with benzyl bromide and a base, to provide aldehyde (120). From aldehyde (120) is made the thioacetal by treatment with 1,2-ethanedithiol. The resulting thioacetal is then to be treated with base to provide the thioacid. Treatment with piperidine makes piperidinium salt (122). By the teaching of Ikeda, infra, (the disclosure of which is incorporated herein by reference) treatment of (122) with 2-chloropyridinium methyl iodide followed by azide ion will give the 1,2,3,4-thiatriazole (124). Debenzylation with boron trifluoride etherate and ethanethiol, followed by hydrolysis and protonation, will provide the product of Example (18).

Scheme 19

The following scheme illustrates a process for making Example (19), a 4-substituted 1,2,3-thiadiazole $LTB_4$ receptor antagonist:

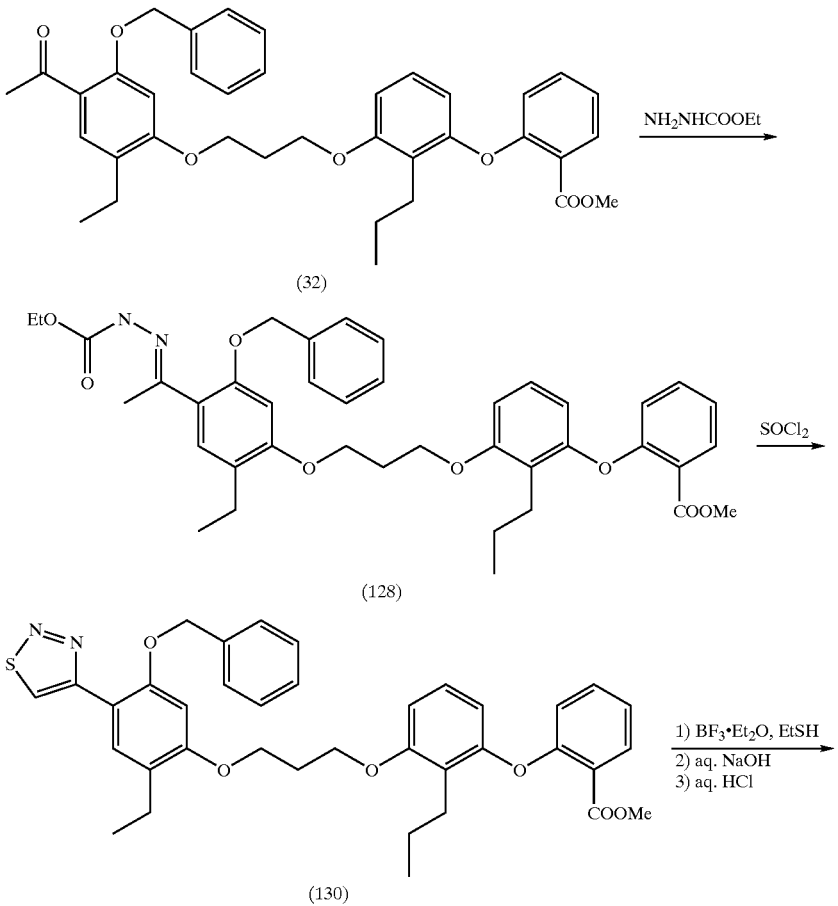

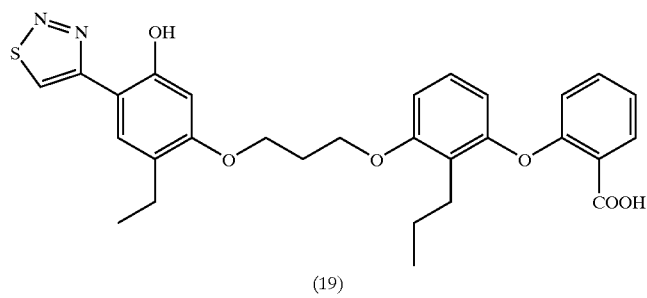

(19)

Reference for 1, 2, 3-thiadiazole formation: E. W. Thomas et al., J. Med. Chem. 1985, 28, 442.

Treatment of acetophenone (32) with ethyl carbazate will give the hydrazone (128). Use of thionyl chloride by the method of Thomas et. al. (infra., the disclosure of which is incorporated herein by reference) will give an intermediate 1,2,3-thiadiazole (130), that is to be debenzylated with boron trifluoride etherate and ethanethiol, then hydrolyzed and protonated to give the product of Example (19).

Scheme 20

The following scheme illustrates a process for making Example (20), a 3-substituted 1,2,5-thiadiazole $LTB_4$ receptor antagonist:

Scheme 20

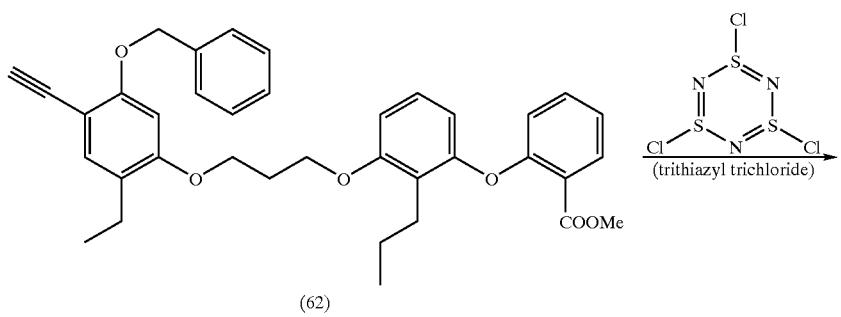

(62)

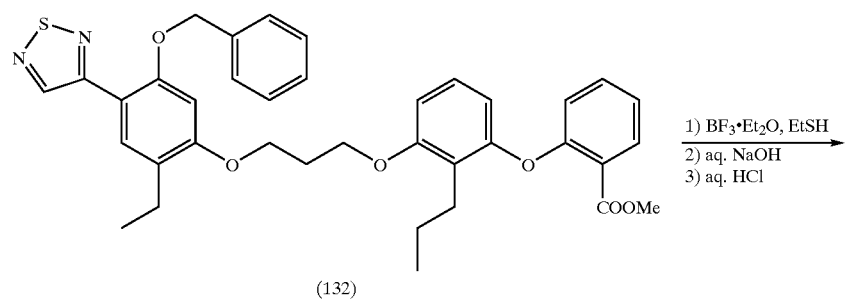

(132)

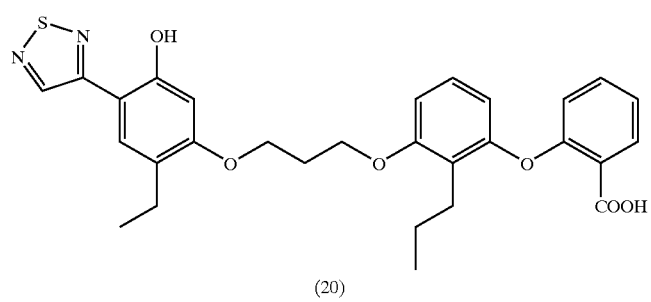

(20)

Reference for 1, 2, 5-thiadiazole formation: E. W. Thomas et al., J. Med. Chem. 1985, 28, 442.

Alkyne (62) is to be treated with trithiazyl trichloride by the method of Thomas et. al. (infra., the disclosure of which is incorporated herein by reference) to provide thiadiazole (132). Debenzylation with boron trifluoride etherate and ethanethiol, followed by hydrolysis and protonation, will provide the product of Example (20).

Scheme 21

The following scheme illustrates a process for making Example (21), a 2-substituted 1,3,4-thiadiazole $LTB_4$ receptor antagonist:

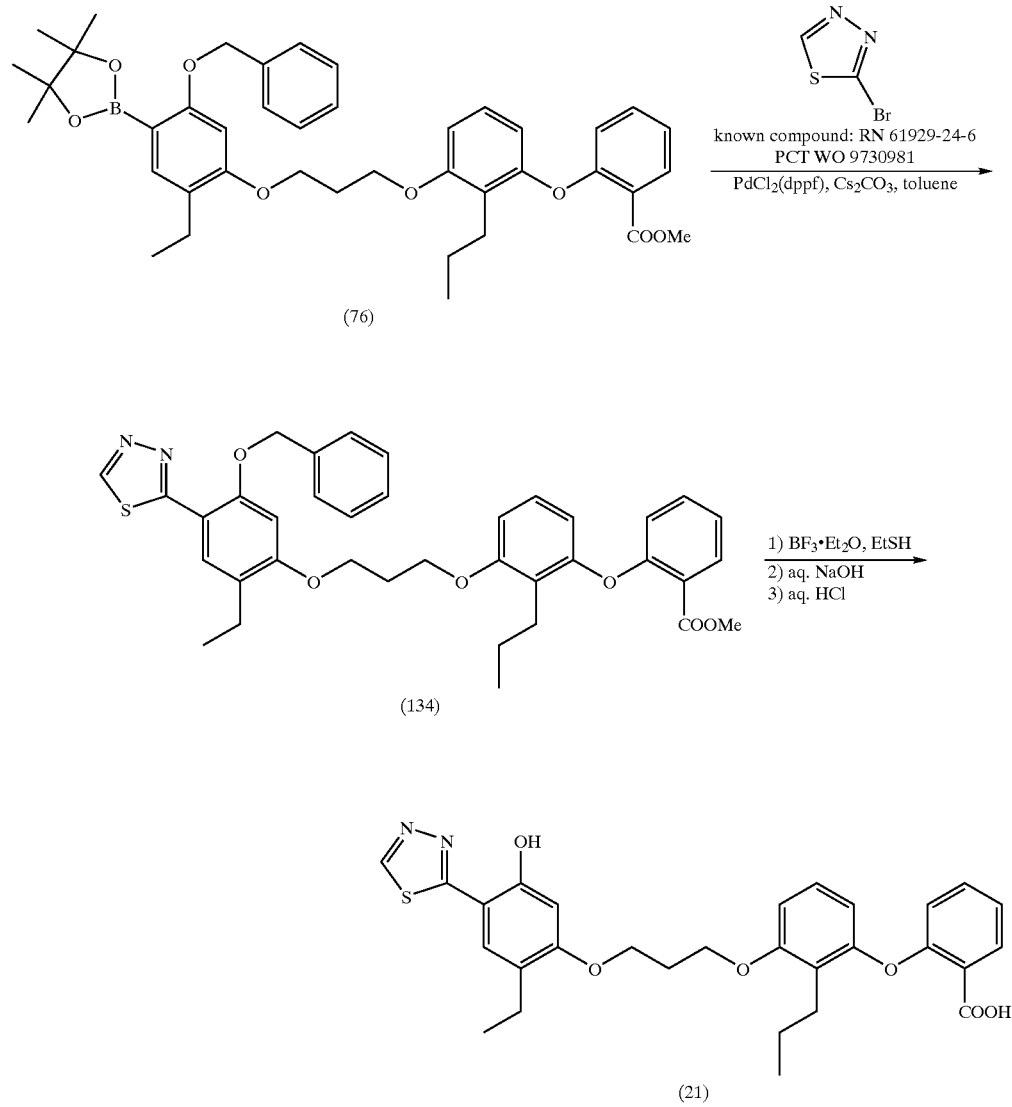

The palladium-catalyzed addition of boronic ester (76) to 2-bromo-1,3,4-thiadiazole will provide ester (134). Debenzylation with boron trifluoride etherate and ethanethiol, followed by hydrolysis and protonation, will provide the product of Example (21).

Scheme 22

The following scheme illustrates a process for making Example (22), a 5-substituted isothiazole LTB$_4$ receptor antagonist:

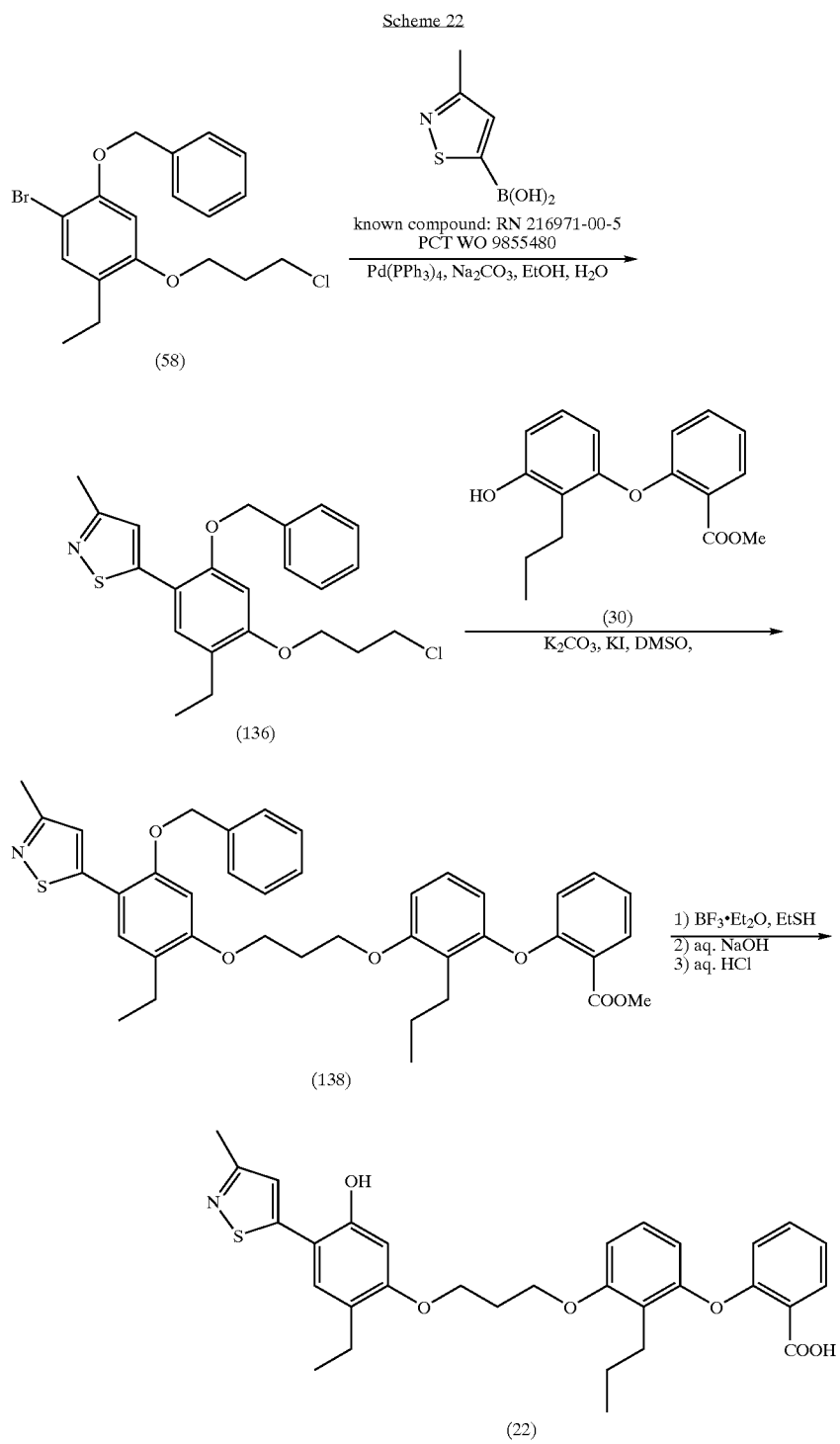

The palladium-catalyzed addition of bromide (58) to 3-methylisothiazole-5-boronic acid will provide isothiazole (136). Alkylation of phenol (30) with (136) catalyzed by base will provide isothiazole (138). Debenzylation with boron trifluoride etherate and ethanethiol, followed by hydrolysis and protonation, will provide the product of Example (22).

Scheme 23

The following scheme illustrates a process for making Example (23), a 2-substituted oxazole LTB$_4$ receptor antagonist:

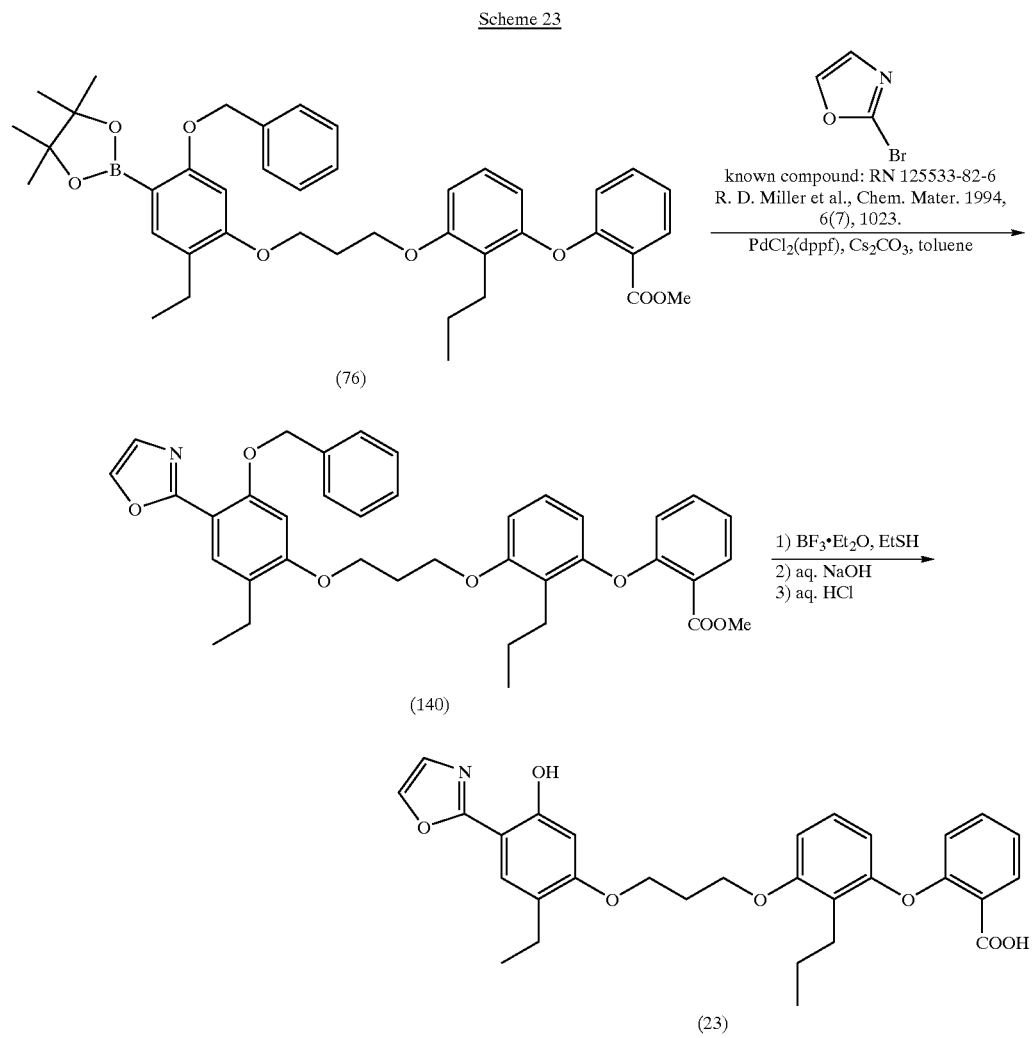

The palladium-catalyzed addition of boronic ester (76) to 2-bromooxazole will provide oxazole (140). Debenzylation with boron trifluoride etherate and ethanethiol, followed by hydrolysis and protonation, will provide the product of Example (23).

Scheme 24

The following scheme illustrates a process for making Example (24), a 3-substituted thiophane LTB$_4$ receptor antagonist:

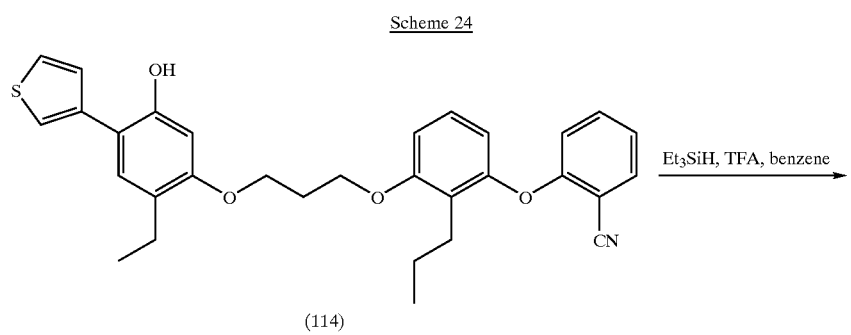

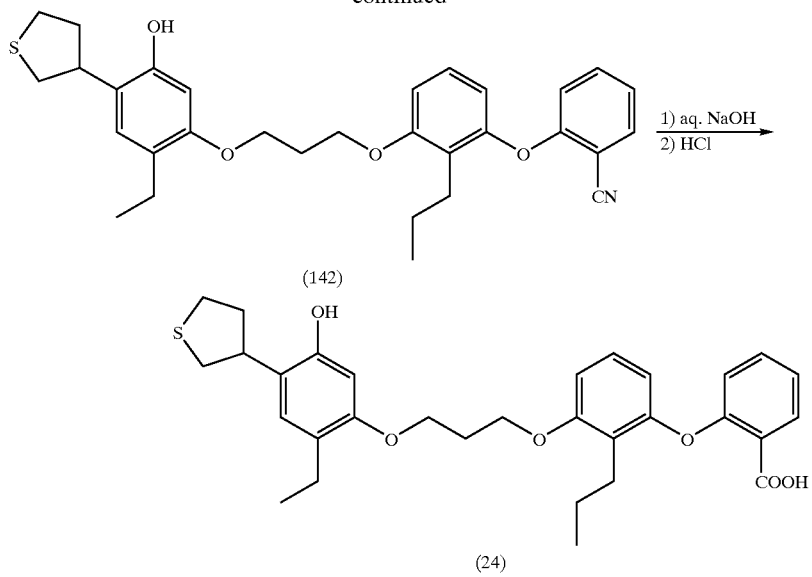

Reference for formation of tetrahydrothiophenes: D. N. Kursanow et al. Tetrahedron 1975, 31, 311

Thiophene (114) may be reduced in the presence of triethylsilane and trifluoroacetic acid by the method of Kursanov et. al. (infra., the disclosure of which is incorporated herein by reference) to provide the thiophane (142). Hydrolysis and protonation will provide the product of Example (24).

V. PREPARATIVE EXAMPLES 1 TO 17:

Example 1

Preparation of 2-{3-[3-(2-Ethyl-5-hydroxy-4-oxazol-4-yl-phenoxy)propoxy]-2-propyl-phenoxy}benzoic acid.

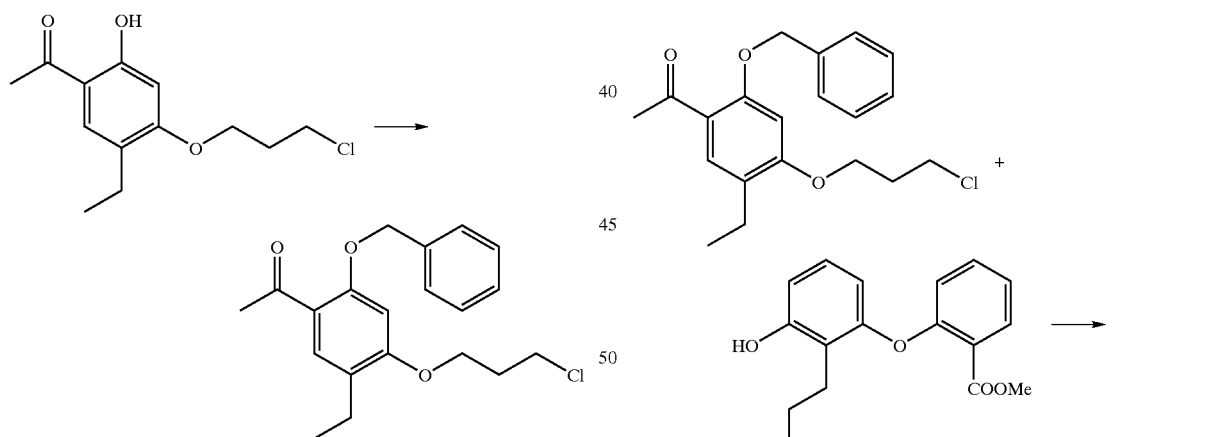

known compound: RN# 156005-61-7
R. W. Harper et al., J. Med. Chem. 1994, 37(15), 2411-20

Know compound: RN# 152609-76-2
J. S. Sawyer et al., J. Med. Chem. 1995, 38, 4411

A. Preparation of 1-[2-benzyloxy-4-(3-chloropropoxy)-5-ethylphenyl]ethanone.

A mixture of 1-[2-hydroxy-4-(3-chloropropoxy)-5-ethylphenyl]ethanone (26.1 g, 102 mmol), cesium carbonate (33.4 g, 103 mmol), and benzyl bromide (12.2 ml, 103 mmol), in N,N-dimethylformamide (300 mL) was stirred for 5 h at room temperature. The mixture was diluted with ethyl acetate and washed four times with water. The organic layer was dried (sodium sulfate), filtered, and concentrated in vacuo. The resulting oil was triturated with ethyl acetate and hexane, allowed to stand for 18 h, then cooled at 0° C. for 3 h. The resulting precipitate was collected via vacuum filtration to provide 24.3 g (69%) of the title compound as white crystals: mp 60–61° C. $^1$H NMR (CDCl$_3$) δ 7.68 (s, 1H), 7.40 (m, 5H), 6.48 (s, 1H), 5.17 (s, 2H), 4.13 (t, J=6 Hz, 2H), 3.75 (t, J=6 Hz, 2H), 2.56 (s, 3H), 2.55 (q, J=7 Hz, 2H), 2.26 (quintet, J=6 Hz, 2H), 1.16 (t, J=7 Hz, 3H); TOF MS ES$^+$ exact mass calculated for C$_{20}$H$_{24}$ClO$_3$ (p+1): m/z= 347.1414. Found: 347.1402; IR (CHCl$_{13}$, cm$^{-1}$) 1659, 1602, 1266. Anal. Calcd for C$_{20}$H$_{23}$ClO$_3$: C, 69.26; H, 6.68. Found: C, 69.30; H, 6.52.

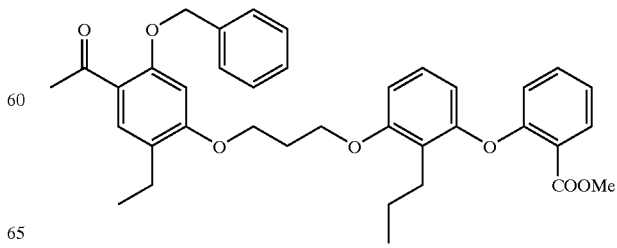

B. Preparation of 2-{3-[3-(4-acetyl-5-benzyloxy-2-ethylphenoxy)propoxy]-2-propyl-phenomy}benzoic acid methyl ester.

A mixture of 1-[2-benzyloxy-4-(3-chloropropoxy)-5-ethylphenyl]ethanone (7.27 g, 21.0 mmol) and sodium iodide (3.14 g, 23.1 mmol) in 2-butanone (100 mL) was heated at reflux for 18 h. The mixture was cooled to room temperature, filtered, and concentrated in vacuo. The residue was dissolved in N,N-dimethylformamide (100 mL) and treated with 2-(3-hydroxy-2-propylphenoxy)benzoic acid methyl ester (6.0 g, 21 mmol) and potassium carbonate (3.2 g, 23 mmol) at room temperature for 15 h. The mixture was diluted with ethyl acetate and washed four times with water and once with saturated sodium chloride solution. The organic layer was dried (sodium sulfate), filtered, and concentrated in vacuo. Chromatography (silica gel, 10% ethyl acetate/90% hexane) of the residue provided 9.2 g (72%) of the title compound as a colorless oil. $^1$H NMR (CDCl$_3$) δ 7.88 (d, J=9 Hz, 1H), 7.69 (s, 1H), 7.38 (m, 6H), 7.12 (d, J=8 Hz, 1H), 7.07 (d, J=8 Hz, 1H), 6.80 (d, J=8 Hz, 1H), 6.67 (d, J=8 Hz, 1H), 6.50 (s, 1H), 6.44 (d, J=9 Hz, 1H), 5.14 (s, 2H), 4.20 (m, 4H), 3.83 (s, 3H), 2.65 (t, J=7 Hz, 2H), 2.57 (q, J=7 Hz, 2H), 2.56 (s, 3H), 2.32 (quintet, J=6 Hz, 2H), 1.55 (hextet, J=7 Hz, 2H), 1.15 (t, J=8 Hz, 3H), 0.90 (t, J=7 Hz, 3H); IR (CHCl$_3$, cm$^{-1}$) 2965, 1726, 1602, 1461. Anal. Calcd for C$_{37}$H$_{40}$O$_7$: C, 74.48; H, 6.76. Found: C, 74.39; H, 6.77.

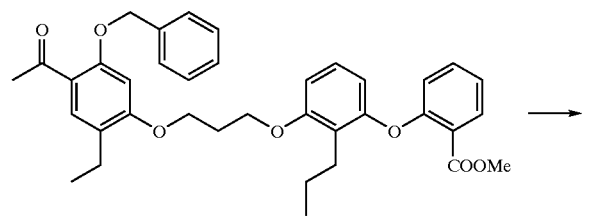

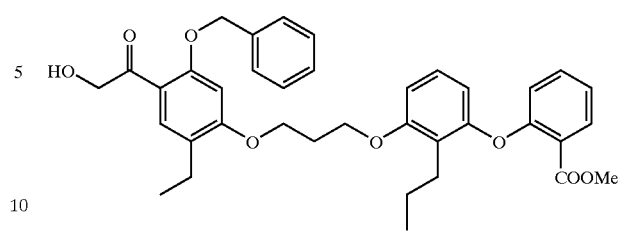

C. Preparation of 2-(3-{3-[5-benzyloxy-2-ethyl-4-(2-hydroxyacetyl)phenoxy]propoxy}-2-propylphenoxy)benzoic acid methyl eater.

A mixture of 2-{3-[3-(4-acetyl-5-benzyloxy-2-ethylphenoxy)propoxy]-2-propyl-phenoxy}benzoic acid methyl ester (5.31 g, 8.89 mmol) and water (10 mL) in acetonitrile (50 mL) was treated with trifluoroacetic acid (1.4 mL), 18 mmol) and [bis(trifluoroacetoxy)iodo]benzene (7.65 g, 17.8 mmol). The resulting mixture was heated at reflux for 4 h then concentrated in vacuo. The residue was dissolved in methylene chloride and washed once with water. The aqueous layer was extracted twice with fresh portions of methylene chloride. The combined organic layers were washed three times with saturated sodium bicarbonate solution, once with saturated sodium chloride solution, dried (sodium sulfate), filtered, and concentrated in vacuo. Chromatography (silica gel, 20% ethyl acetate/80% hexane) of the residue provided 1.68 g (31%) of the title compound as a brown oil. $^1$H NMR (CDCl$_3$) δ 7.92 (s, 1H), 7.88 (d, J=9 Hz, 1H), 7.40 (m, 6H), 7.12 (d, J=9 Hz, 1H), 7.05 (d, J=9 Hz, 1H), 6.79 (d, J=8 Hz, 1H), 6.66 (d, J=8 Hz, 1H), 6.50 (s, 1H), 6.43 (d, J=8 Hz, 1H), 5.15 (s, 2H), 4.65 (s, 2H), 4.22 (m. 4H), 3.83 (s, 3H), 2.65 (m, 4H), 2.34 (quintet, J=6 Hz, 2H), 1.55 (hextet, J=7 Hz, 2H), 1.17 (t, J=8 Hz, 3H), 0.89 (t, J=8 Hz, 3H); TOS MS ES$^+$ exact mass calculated for C$_{37}$H$_{41}$O$_8$ (p+1): m/z=613.2801. Found: 613.2833.

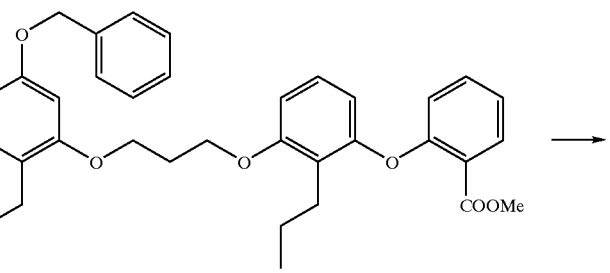

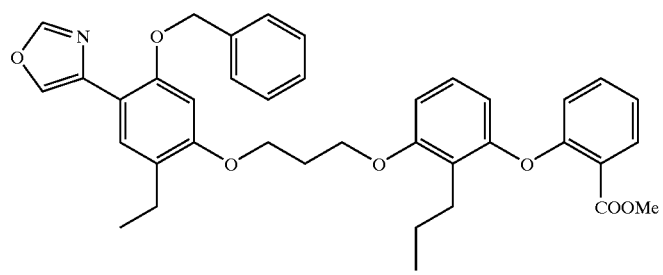

D. Preparation of 2-{3-[3-(5-benzyloxy-2-ethyl-4-oxazol-4-yl-phenoxy)propoxy]-2-propylphenoxy}benzoic acid methyl eater.

To a solution of 2-(3-{3-[5-benzyloxy-2-ethyl-4-(2-hydroxyacetyl)phenoxy]propoxy}-2-propylphenoxy) benzoic acid methyl ester (1.39 g, 2.27 mmol) in methylene chloride (20 mL) cooled to −78° C. was added triflic anhydride (0.57 mL, 3.4 mmol) and 2,6-lutidine (0.40 mL, 3.4 mmol). The resulting mixture was stirred for 1 h then poured into ether and water. The organic layer was separated and washed once with saturated sodium chloride solution, dried (sodium sulfate), filtered, and concentrated in vacuo. The residue was dissolved in a 2:1 mixture of formamide/N,N-dimethylformamide (9 mL) and heated at 120° C. in a sealed tube for 4 h. The mixture was cooled to room temperature and diluted with ethyl acetate. The mixture was washed four times with water, once with saturated sodium chloride solution, dried (sodium sulfate), filtered, and concentrated in vacuo. Chromatography (silica gel, 10% ethyl acetate/90% hexane) of the residue provided 89 mg (6%) of the title product as a colorless oil. $^1$H NMR (CDCl$_3$) δ 7.92 (s, 1H), 7.85 (s, 1H), 7.83 (m, 2H), 7.35 (m, 6H), 7.03 (d, J=8 Hz, 1H), 7.00 (d, J=8 Hz, 1H), 6.73 (d, J=8 Hz, 1H), 6.62 (d, J=8 Hz, 1H), 6.52 (s, 1H), 6.35 (d, J=8 Hz, 1H), 5.07 (s, 2H), 4.14 (m, 4H), 3.76 (s, 3H), 2.61 (m, 4H), 2.26 (quintet, J=6 Hz, 2H), 1.48 (hextet, J=7 Hz, 2H), 1.15 (t, J=8 Hz, 3H), 0.84 (t, J=8 Hz, 3H).

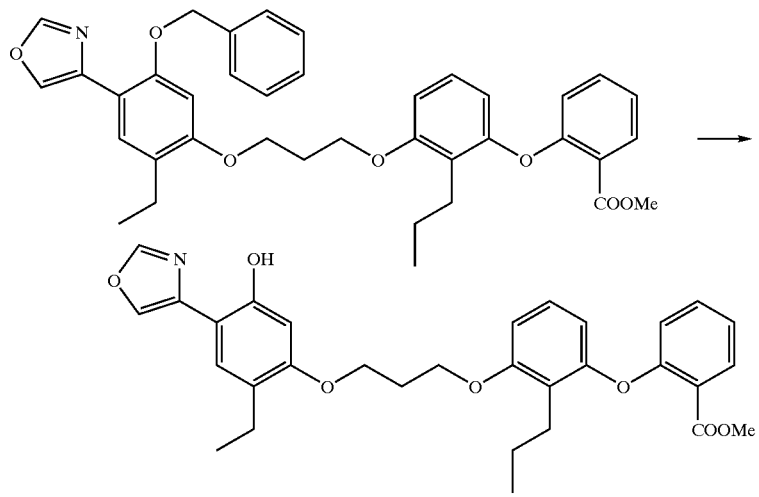

E. Preparation of 2-{3-[3-(2-ethyl-5-hydroxy-4-oxazol-4-yl-phenoxy)propoxy]-2-propylphonomy}benzoic acid methyl ester.

To a solution of 2-{3-[3-(5-benzyloxy-2-ethyl-4-oxazol-4-yl-phenoxy)propoxy]-2-propylphenoxy}benzoic acid methyl ester (89 mg, 0.14 mmol) in ethanethiol (2 mL) was treated with boron trifluoride etherate (0.27 mL, 2.2 mmol) at room temperature for 4 h. The solution was poured into ether and washed once with water, once with saturated sodium bicarbonate solution, once with saturated sodium chloride solution, dried (sodium sulfate), filtered, and concentrated in vacuo. Chromatography (silica gel, 15% ethyl acetate/85% hexane) of the residue provided 34 mg (45%) of the title product as a light brown oil. $^1$H NMR (CDCl$_3$) δ 7.99 (d, J=1 Hz, 1H), 7.90 (d, J=1 Hz, 1H), 7.88 (dd, J=8, 2 Hz, 1H), 7.38 (t, J=7 Hz, 1H), 7.15 (s, 1H), 7.10 (d, J=9 Hz, 1H), 7.06 (d, J=9 Hz, 1H), 6.81 (d, J=9 Hz, 1H), 6.70 (d, J=9 Hz, 1H), 6.52 (s, 1H), 6.44 (d, J=9 Hz, 1H), 4.20 (m, 4H), 3.83 (s, 3H), 2.65 (t, J=8 Hz, 2H), 2.58 (q, J=8 Hz, 2H), 2.33 (quintet, J=6 Hz, 2H), 1.55 (hextet, J=7 Hz, 2H), 1.17 (t, J=8 Hz, 3H), 0.91 (t, J=8 Hz, 3H); MS ES+m/e=532 (p+1).

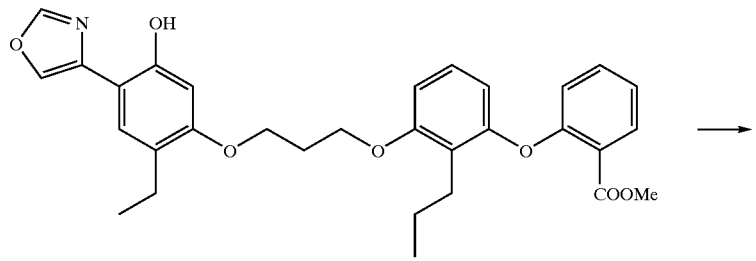

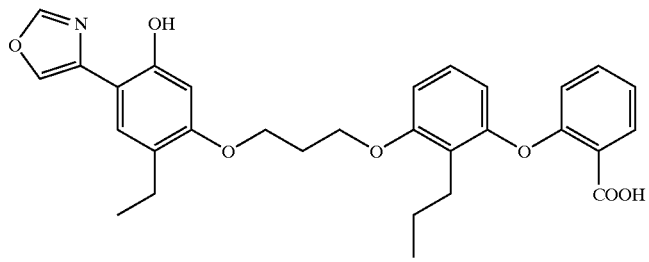

F. Preparation of 2-{3-[3-(2-ethyl-5-hydroxy-4-oxazol-4-yl-pbenoxy)propoxy]-2-propylphonoxy}benzoic acid.

To a solution of 2-{3-[3-(2-ethyl-5-hydroxy-4-oxazol-4-yl-phenoxy)propoxy]-2-propylphenoxy}benzoic acid methyl ester (89 mg, 0.14 mmol) in methanol (2 mL) was added 1 M lithium hydroxide solution (0.28 mL) and the resulting mixture warmed at 60° C. for 3.5 h. The mixture was cooled to room temperature and concentrated in vacuo. The aqueous residue was diluted with water and the pH adjusted to ~4. The mixture was extracted three times with methylene chloride. The combined organic extracts were dried (sodium sulfate), filtered, and concentrated in vacuo to provide 27 mg (92%) of the title compound as a yellow solid. $^1$H NMR (DMSO-$d_6$) δ 12.83 (bs, 1H), 10.12 (bs, 1H), 8.39 (s, 1H), 8.25 (s, 1H), 7.78 (dd, J=8, 1 Hz, 1H), 7.64 (s, 1H), 7.47 (t, J=8 Hz, 1H), 7.16 (m, 2H), 6.80 (t, J=8 Hz, 2H), 6.56 (s, 1H), 6.35 (d, J=8 Hz, 1H), 4.20 (t, J=6 Hz, 2H), 4.12 (t, J=6 Hz, 2H); 2.54 (m, 4H), 2.24 (quintet, J=6 Hz, 2H), 1.43 (hextet, J=8 Hz, 2H), 1.10 (t, J=8 Hz, 3H), 5 0.80 (t, J=8 Hz, 3H); TOF MS ES$^+$ exact mass calculated for $C_{30}H_{32}NO_7$ (p+1): m/z=518.2179. Found: 518.2206; IR (KBr, cm$^{-1}$) 2961, 1696, 1460, 1222. Anal. Calcd for $C_{30}H_{31}NO_7$: C, 69.62; H, 6.04; N, 2.71. Found: C, 68.71; H. 5.82; N, 2.65.

Example 2

Preparation of 2-(3-{3-[2-Ethyl-5-hydroxy-4-(3H-imidazol-4-yl)phenoxy]propoxy}-2-propyl-phenoxy)benzoic acid hydrochloride.

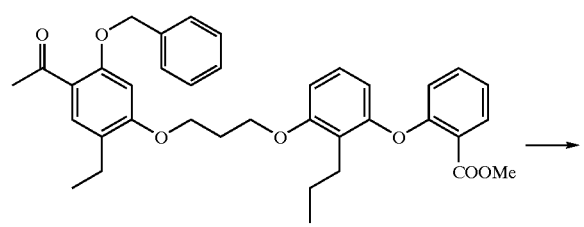

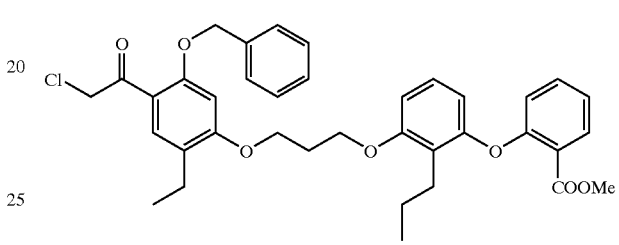

A. Preparation of 2-(3-{3-[5-benzyloxy-4-(2-chloroacetyl)-2-ethylphenoxy]propoxy}-2-propylphenoxy)benzoic acid methyl ester.

To a solution of 2-{3-[3-(4-acetyl-5-benzyloxy-2-ethylphenoxy)propoxy]-2-propyl-phenoxy}benzoic acid methyl ester (3.04 g, 5.09 mmol) in tetrahydrofuran (50 mL) cooled to −78° C. was added a solution of 1 M lithium hexamethyldisilazide in tetrahydrofuran (11.2 mL, 11.2 mmol) portion wise. After stirring for 20 min, trimethylsilyl chloride (2.6 mL. 20 mmol) was added and the mixture warmed to 0° C. and stirred for 30 min. The mixture was evaporated in vacuo and the residue dissolved in hexane. The resulting solution was filtered and concentrated in vacuo. The residue was dissolved in tetrahydrofuran (50 mL), cooled to 0° C., and treated with N-chlorosuccinimide (750 mg, 5.6 mmol). The mixture was warmed to room temperature and stirred for 30 min, then heated at reflux for 2 h. The mixture was cooled to room temperature and treated with water (4 mL) and a solution of 1 N tetra-n-butylammonium fluoride in tetrahydrofuran (6 mL). After stirring for 15 min the mixture was diluted in ether and washed once with water, once with saturated sodium chloride solution, dried (sodium sulfate), filtered, and concentrated in vacuo. Chromatography (silica gel, 10% ethyl acetate/90% hexane) of the residue provided 1.94 g (60%) of the title compound as a white solid. $^1$H NMR (CDCl$_3$) δ 7.89 (d, J=8 Hz, 1H), 7.77 (s, 1H), 7.40 (m, 6H), 7.12 (d, J=9 Hz, 1H), 7.06 (d, J=8 Hz, 1H), 6.80 (d, J=8 Hz, 1H), 6.66 (d, J=8 Hz, 1H), 6.49 (s, 1H), 6.43 (d, J=8 Hz, 1H), 5.15 (s, 2H), 4.68.(s, 2H), 4.20 (q, J=6 Hz, 4H), 3.82 (s, 3H), 2.65 (t, J=7 Hz, 2H), 2.59 (q, J=7 Hz, 2H), 2.32 (quintet, J=6 Hz, 2H), 1.54 (hextet, J=8 Hz, 2H), 1.16 (t, J=8 Hz, 3H), 0.89 (t, J=7 Hz, 3H); TOF MS ES$^+$ exact mass calculated for $C_{37}H_{40}ClO_7$ (p+1): m/z=631.2463. Found: 631.2470; IR (CHCl$_3$, cm$^{-1}$) 2964, 1720, 1603, 1461. Anal. Calcd for $C_{37}H_{39}ClO_7$: C, 70.41; H, 6.23. Found: C, 0.04; H, 5.97.

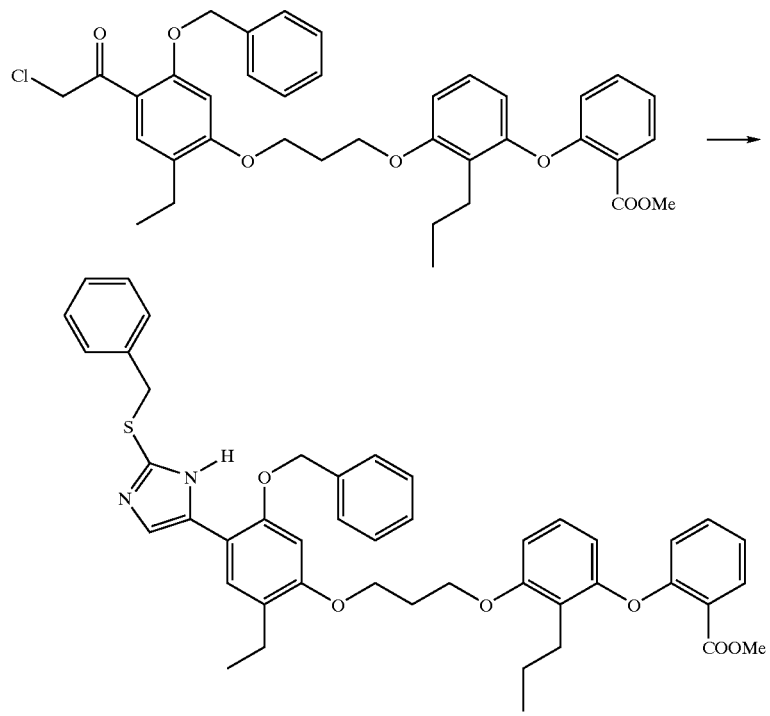

B. Preparation of 2-(3-{3-[5-benzyloxy-4-(2-benzylulfanyl-3H-imidazol-4-yl)-2-ethyl-phenoxy]propoxy}-2-propylphenoxy)benzoic acid methyl enter.

A mixture of 2-(3-{3-[5-benzyloxy-4-(2-chloroacetyl)-2-ethylphenoxy]propoxy}-2-propylphenoxy)benzoic acid methyl ester (800 mg, 1.27 mmol), 2-benzyl-2-thiopseudourea hydrochloride (313 mg, 1.52 mmol), sodium iodide (77 mg, 0.51 mmol), and potassium carbonate (700 mg, 5.06 mmol) in N,N-dimethylformamide (20 mL) was treated at 80° C. for 6 h. The mixture was cooled, diluted with diethyl ether, and washed once with water. The organic layer was dried (sodium sulfate), filtered, and concentrated in vacuo. Chromatography (silica gel, 30% ethyl acetate/70% hexane) of the residue provided 376 mg (40%) of the title compound as a yellow amorphous solid. $^1$H NMR (CDCl$_3$) δ 7.89 (d, J=8 Hz, 1H), 7.36 (m, 9H), 7.20 (m, 5H), 7.21 (d, J=9 Hz, 1H), 7.06 (d, J=8 Hz, 1H), 6.79 (d, J=8 Hz, 1H), 6.67 (d, J=8 Hz, 1H), 6.55 (s, 1H), 6.43 (d, J=8 Hz, 1H), 5.07 (s, 2H), 4.21 (t, J=6 Hz, 2H), 4.18 (t, J=6 Hz, 2H), 4.10 (s, 2H), 3.83 (s, 3H), 2.63 (m, 4H), 2.31 (quintet, J=6 Hz, 2H), 1.55 (hextet, J=7 Hz, 2H), 1.18 (t, J=8 Hz, 3H), 0.90 (t, J=7 Hz, 3H); TOF MS ES exact mass calculated for C$_{45}$H$_{47}$N$_2$O$_6$S (p+1): m/z=743.3155. Found: 743.3142; IR (CHCL$_3$, cm$^{-1}$) 2963, 1720, 1602, 1453. Anal. Calcd for C$_{45}$H$_{46}$N$_2$O$_6$S: C, 72.75; H. 6.24; N, 3.77. Found: C, 72.69; H, 6.17; N, 3.56.

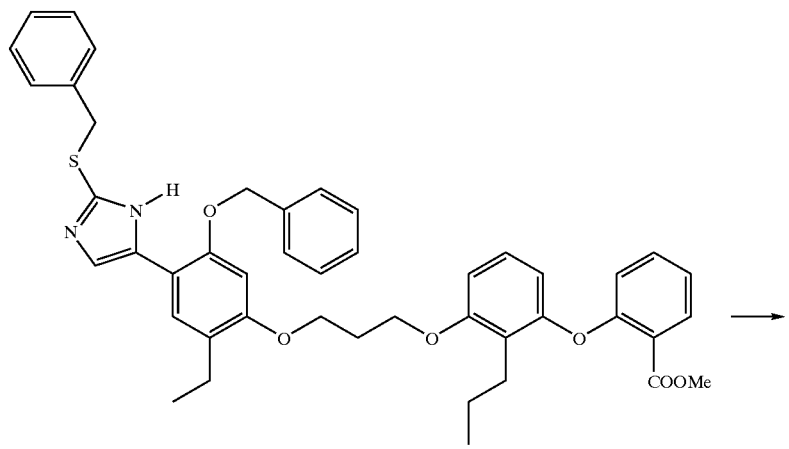

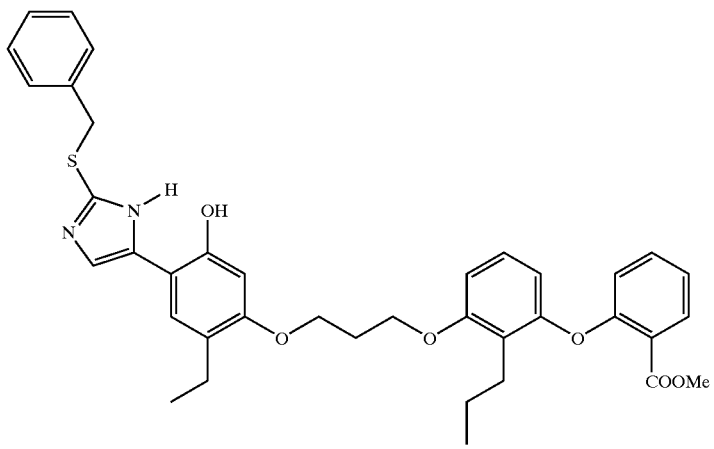

C. Preparation of 2-(3-{3-[4-(2-benzylsulfonyl-3H-imidazol-4-yl)-2-ethyl-5-hydroxyphenoxy]propoxy}-2-propylphenoxy)benzoic acid methyl eater.

A solution of 2-(3-{3-[5-benzyloxy-4-(2-benzylsulfanyl-3H-inidazol-4-yl)-2-ethyl-phenoxy]propoxy}-2-propylphenoxy)benzoic acid methyl ester (360 mg, 0.49 mmol) in ethanethiol (7 mL) was treated with boron trifluoride etherate at room temperature for 3.5 h. The mixture was diluted with diethyl ether and water. The organic layer was separated and washed with saturated sodium bicarbonate solution, dried (sodium sulfate), filtered, and concentrated in vacuo. Chromatography (silica gel, 20% ethyl acetate/80% hexane) of the residue provided 154 mg (48%) of the title compound as an orange oil. $^1$H NMR (CDCl$_3$) δ 7.85 (d, J=8 Hz, 1H), 7.36 (t, J=7 Hz, 1H), 7.20 (m, 7H), 7.12 (s, 1H), 7.05 (m, 3H), 6.79 (d, J=8 Hz, 1H), 6.65 (d, J=8 Hz, 1H), 6.54 (s, 1H), 6.41 (d, J=8 Hz, 1H), 4.20 (s, 2H), 4.17 (m, 4H), 3.82 (s, 3H), 2.62 (t, J=8 Hz, 2H), 2.54 (q, J=7 Hz, 2H), 2.30 (quintet, J=6 Hz, 2H), 1.53 (hextet, J=8 Hz, 2H), 1.14 (t, J=7 Hz, 3H), 0.89 (t, J=8 Hz, 3H); TOF MS ES$^+$ exact mass calculated for C$_{38}$H$_{41}$N$_2$O$_6$S (p+1): m/z= 653.2685. Found: 653.2669. Anal. Calcd for C$_{38}$H$_{40}$N$_2$O$_6$S: C, 69.92; H, 6.18; N, 4.29. Found: C, 69.44; H, 6.25; N, 3.99.

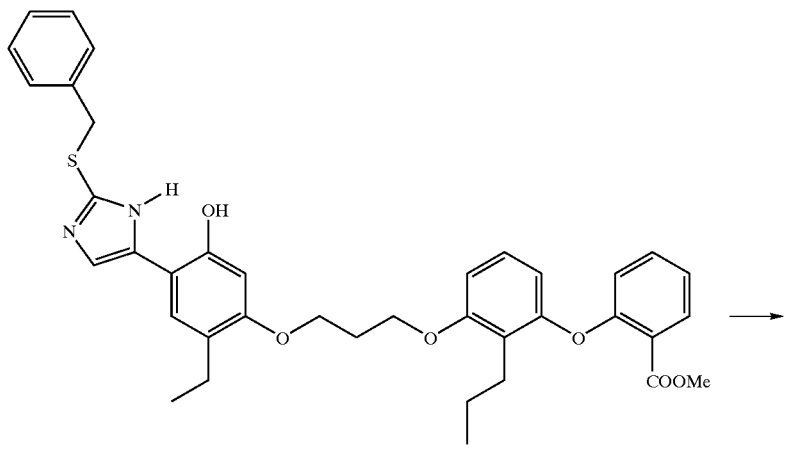

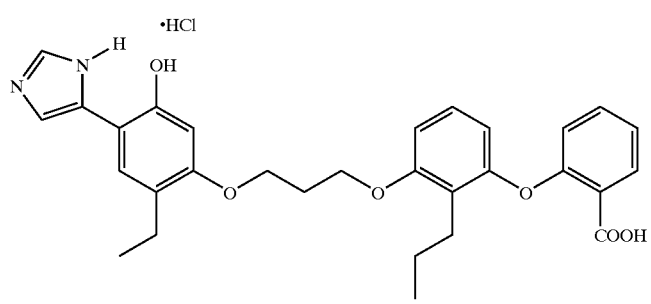

D. Preparation of 2-(3-{3-[2-ethyl-5-hydroxy-4-(3H-imidazol-4-yl)phenoxy]propoxy}-2-propyl-phenoxy)benzoic acid hydrochloride.

A solution of 2-(3-{3-[4-(2-benzylsulfanyl-3H-imidazol-4-yl)-2-ethyl-5-hydroxyphenoxy]propoxy}-2-propylphenoxy)benzoic acid methyl ester (154 mg, 0.235 mmol) in methanol (3 mL) was treated with 1 N lithium hydroxide solution at 60° C. for 3.5 h. The mixture was cooled to room temperature and concentrated in vacuo. The solution was diluted with water and adjusted to pH 4. The aqueous solution was extracted three times with methylene chloride. The combined organic layers were dried (sodium sulfate), filtered, and concentrated in vacuo. The residue was dissolved in ethanol (3 mL) and treated with 0.2 N sodium hydroxide solution (1 mL) and Raney nickel (75 mg) at 75° C. for 4 h. The mixture was cooled to room temperature, filtered through Celite™, and the filtrate concentrated in vacuo. The residue was diluted with water and adjusted to pH 2 with 1 N hydrochloric acid. The resulting precipitate was collected via vacuum filtration to provide 27 mg (21%) of the title compound. TOF MS ES+ exact mass calculated for $C_{30}H_{33}N_2O_6$ (p+1): m/z=517.2339. Found: 517.2340.

Example 3
Preparation of 2-{3-[3-(2-Ethyl-5-hydroxy-4-thiazol-4-yl-phenoxy)propoxy]-2-propyl-phenoxy}benzoic acid.

A. Preparation of 2-{3-[3-(5-benzyloxy-2-ethyl-4-thiazol-4-yl-phenoxy)propoxy]-2-propylphenoxy}benzoic acid methyl ester.

A mixture of 2-(3-{3-[5-benzyloxy-4-(2-chloroacetyl)-2-ethylphenoxy)propoxy]-2-propylphenoxy}benzoic acid methyl ester (500 mg, 0.792 mmol), thioformamide (20 mL, 8.0 mmol), and magnesium carbonate in dioxane (10 mL) was heated at reflux for 2 h. The mixture was cooled to room temperature and diluted with diethyl ether and 0.2 M sodium hydroxide solution. The organic layer was separated, washed with saturated sodium chloride solution, dried (sodium sulfate), filtered, and concentrated in vacuo. Chromatography (silica gel, 10% ethyl acetate/90% hexane) of the residue provided 254 mg (50%) of the title compound as a colorless oil. $^1$H NMR (CDCl$_3$) δ 8.91 (s, 1H), 8.11 (s, 1H), 7.87 (dd, J=8, 1 Hz, 1H), 7.84 (d, J=1 Hz, 1H), 7.40 (m, 6H), 7.08 (m, 2H), 6.80 (d, J=8 Hz, 1H), 6.68 (d, J=8 Hz, 1H), 6.62 (s, 1H), 6.43 (d, J=8 Hz, 1H), 5.16 (s, 2H), 4.21 (t, J=6 Hz, 4H), 3.83 (s, 3H), 2.68 (m, 4H), 2.32 (quintet, J=6 Hz, 2H), 1.56 (hextet, J=8 Hz, 2H), 1.21 Ct, J=7 Hz, 3H), 0.90 (t, J=7 Hz, 3H); TOF MS ES+ exact mass calculated for $C_{38}H_{40}NO_6S$ (p+1): m/z=638.2576. Found: 638.2579. IR (CHCl$_3$, cm$^{-1}$) 2964, 1719, 1563, 1461.

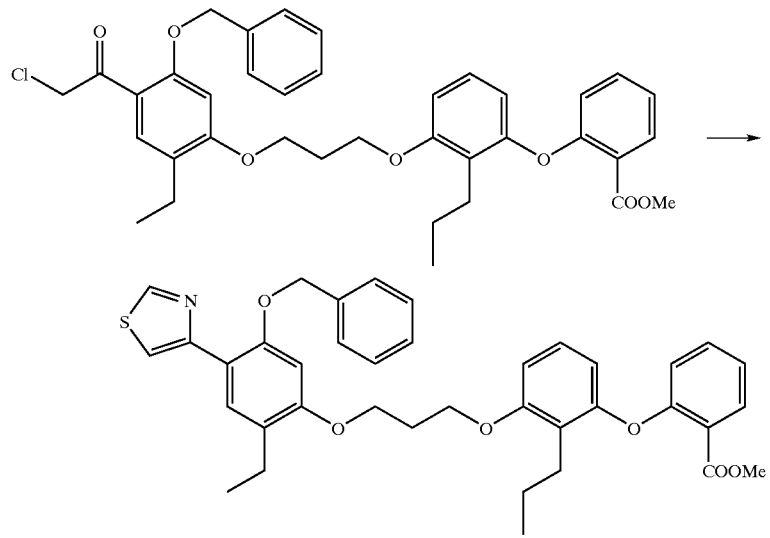

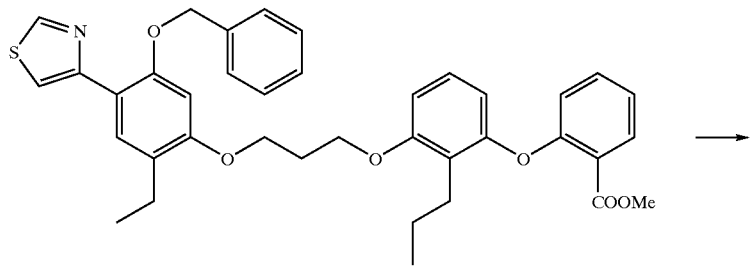

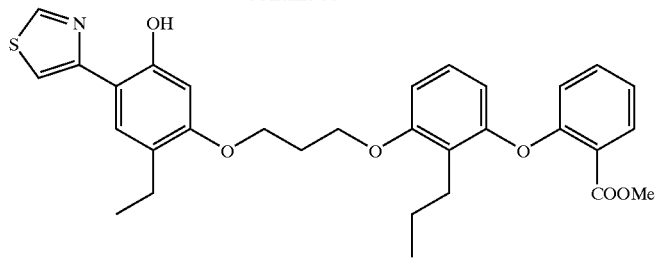

B. Preparation of 2-{3-[3-(2-ethyl-5-hydroxy-4-thiazol-4-yl-phenoxy)propoxy]-2-propylphenoxy}benzoic acid methyl ester.

A solution of 2-{3-[3-(5-benzyloxy-2-ethyl-4-thiazol-4-yl-phenoxy)propoxy]-2-propyl-phenoxy}benzoic acid methyl ester (243 mg, 0.366 mmol) in ethanethiol (7 mL) was treated with boron trifluoride etherate at room temperature for 4 h. The mixture was diluted with diethyl ether, washed once with water, once with saturated sodium bicarbonate solution, dried (sodium sulfate), filtered, and concentrated in vacuo. Chromatography (silica gel, 15% ethyl acetate/85% hexane) of the residue provided 131 mg (65%) of the title compound as a colorless oil. $^1$H NMR (CDCl$_3$) δ 8.88 (d, J=1 Hz, 1H), 7.88 (dd, J=8, 1 Hz, 1H), 7.44 (d, J=1 Hz, 1H), 7.38 (m, 2H), 7.08 (m, 2H), 6.81 (d, J=8 Hz, 1H), 6.68 (d, J=8 Hz, 1H), 6.55 (s, 1H), 6.43 (d, J=8 Hz, 1H), 4.21 (t, J=6 Hz, 4H), 3.83 (s, 3H), 2.63 (m, 4H), 2.33 (quintet, J=6 Hz, 2H), 1.56 (hextet, J=8 Hz, 2H), 1.19 (t, J=8 Hz, 3H), 0.91 (t, J=7 Hz, 3H); TOF MS ES$^+$ exact mass calculated for C$_{31}$H$_{34}$NO$_6$S (p+1): m/z=548.2107. Found: 548.2085.

C. preparation of 2-{3-[3-(2-ethyl-5-hydroxy-4-thiazol-4-yl-phenoxy)propoxy]-2-propylphenoxy}benzoic acid.

A solution of 2-{3-[3-(2-ethyl-5-hydroxy-4-thiazol-4-yl-phenoxy)propoxy]-2-propylphenoxy}benzoic acid methyl ester (130 mg, 0.236 mmol) in methanol (4 mL) was treated with 1 M lithium hydroxide solution at 60° C. for 3 h. The mixture was cooled to room temperature, concentrated in vacuo, and diluted with water. The solution was adjusted to pH ~4 and extracted three times with methylene chloride. The combined organic layers were dried (sodium sulfate), filtered, and concentrated in vacuo. The residue was dissolved in a minimum of methylene chloride and hexane was added until the solution became cloudy. The mixture was concentrated slowly in vacuo to give 96 mg (76%) of the title compound. $^1$H NMR (CDCl$_3$) δ 8.90 (s, 1H), 8.23 (dd, J=8, 1 Hz, 1H), 7.41 (m, 2H), 7.38 (s, 1H), 7.29 (m, 2H), 6.82 (d, J=8 Hz, 1H), 6.71 (d, J=3 Hz, 1H), 6.62 (d, J=8 Hz, 1H), 6.54 (s, 1H), 4.25 (t, J=6 Hz, 2H), 4.22 (t, J=6 Hz, 2H), 2.59 (m, 4H), 2.35 (quintet, J=6 Hz, 2H), 1.50 (hextet, J=8 Hz, 2H), 1.19 (t, J=7 Hz, 3H), 0.88 (t, J=8 Hz, 3H); TOF MS ES$^+$ exact mass calculated for C$_{30}$H$_{32}$NO$_6$S (p+1): m/z=534.1950. Found: 534.1957. IR (CHCl$_3$, cm$^{-1}$) 2965, 1738, 1454. Anal. Calcd for C$_{30}$H$_{31}$NO$_6$S: C, 67.52; H, 5.86; N. 2.62. Found: C, 67.19; H, 5.72; N, 2.53.

Example 4

Preparation of 2-(3-{3-[2-Ethyl-5-hydroxy-4-(2H-pyrazol-3-yl)phenoxy]propoxy}-2-propyl-phenoxy)benzoic acid.

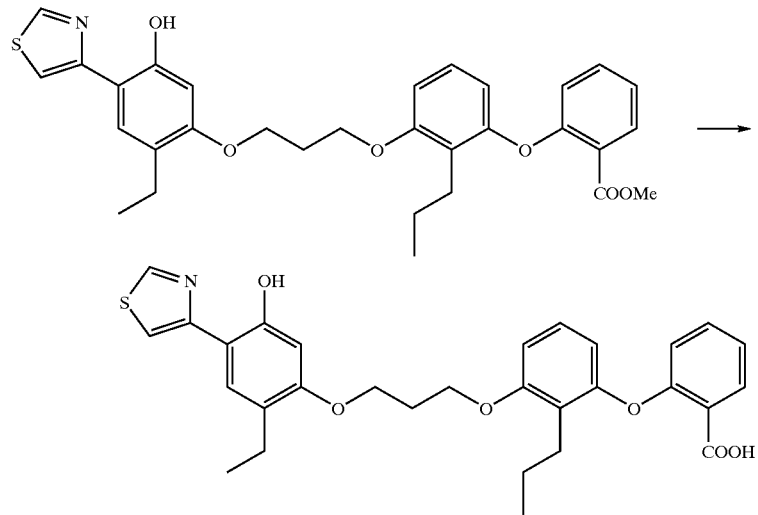

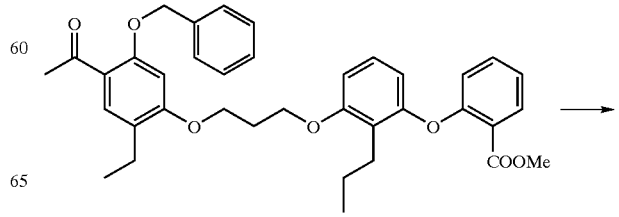

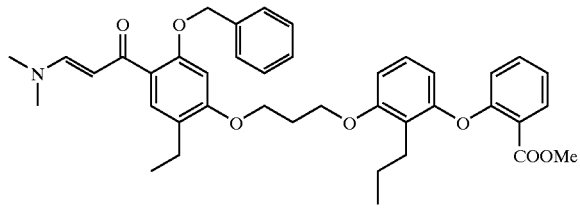

A. Preparation of 2-(3-{3-[5-benzyloxy-4-(3-dimethylaminoacryloyl)-2-ethyl-phenoxy]propoxy}-2-propylphenoxy)benzoic acid methyl eater.

A mixture of 2-(3-{3-[4-acetyl-5-benzyloxy-2-ethylphenoxy]propoxy}-2-propylphenoxy)benzoic acid methyl ester (3.07 g, 5.04 mmol) and dimethylformamide dimethylacetal (0.9 mL, 7 mmol) in N,N-dimethylformamide (3 mL) was heated at 110–120° C. for 35 h. The mixture was cooled to room temperature and diluted with a mixture of ethyl acetate and 1 N hydrochloric acid. The organic layer was separated, washed twice with water, once with saturated sodium chloride solution, dried (sodium sulfate), filtered, and concentrated in vacuo. Chromatography (silica gel, 30% ethyl acetate/70% hexane to ethyl acetate) of the residue provided 2.1 g (63%) of the title compound as a yellow oil. TQF MS ES+ exact mass calculated for $C_{40}H_{46}NO_7$ (p+1): m/z=652.3274. Found: 652.3270. IR (CHCl$_3$, cm$^{-1}$) 2965, 1720, 1605. Anal. Calcd for $C_{40}H_{45}NO_7$: C, 73.71; H, 6.96; N, 2.15. Found: C, 73.72; H, 6.95; N, 2.18.

to room temperature and diluted with ethyl acetate and 0.5 M hydrochloric acid. The organic layer was separated, washed with saturated sodium chloride solution, dried (sodium sulfate), filtered, and concentrated in vacuo. The residue was dissolved in methanol (15 mL) and treated with water (4 mL) and hydrazine monohydrate (0.50 mL, 7.7 mmol) at reflux for 3 h. The mixture was diluted with ethyl acetate and 1 N hydrochloric acid. The organic layer was separated, washed with saturated sodium chloride solution, dried (sodium sulfate), filtered and concentrated in vacuo. Chromatography (30% ethyl acetate/69% hexane/1% acetic acid) of the residue provided 350 mg (65%) of the title compound as the acetate salt. A portion of this material was free-based with sodium bicarbonate to provide an analytical sample. $^1$H NMR (CDCl$_3$) δ 8.20 (dd, J 8, 2 Hz, 1H), 7.55 (s, 1H), 7.44 (s, 1H), 7.38 (m, 5H), 7.15 (m, 2H), 6.78 (d, J=8 Hz, 1H), 6.65 (d, J=8 Hz, 1H), 6.61 (d, J=8 Hz, 1H), 6.58 (s, 1H), 6.55 (bs, 1H), 5.18 (s, 2H), 4.22 (t, J=6 Hz, 2H), 4.17 (t, J=6 Hz, 2H), 2.58 (m, 4H), 2.30 (quintet, J=6 Hz, 2H), 1.47 (hextet, J=8 Hz, 2H), 1.18 (t, J=7 Hz, 3H), 0.88 (t, J=8 Hz, 3H); TOF MS ES$^+$ exact mass calculated for $C_{37}H_{39}N_2O_6$ (p+1): m/z=607.2808. Found: 607.2831. IR (CHCl$_3$, cm$^{-1}$) 2965, 1739, 1604, 1454. Anal. Calcd for $C_{37}H_{38}N_2O_6$: C, 73.25; H, 6.31; N, 4.62. Found: C, 73.31; H, 6.30; N, 4.62.

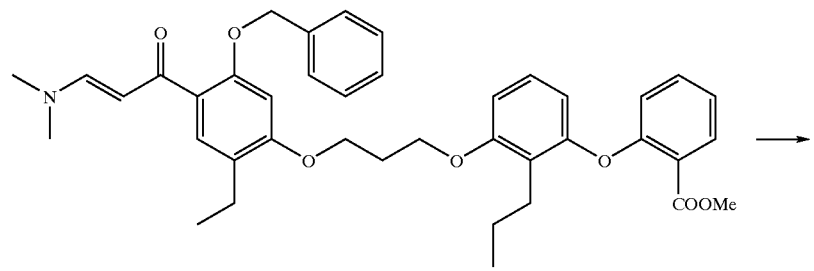

B. Preparation of 2-(3-{3-[5-benzyloxy-2-ethyl-4-(2H-pyrazol-3-yl)phenoxy]propoxy}-2-propylphenoxy)benzoic acid.

A solution of 2-(3-{3-[5-benzyloxy-4-(3-dimethylaminoacryloyl)-2-ethyl-phenoxylpropoxy)-2-propylphenoxy)benzoic acid methyl ester (550 mg, 0.843 mmol in methanol (30 mL) was treated with 1 M lithium hydroxide solution at 60° C. for 3 h. The mixture was cooled

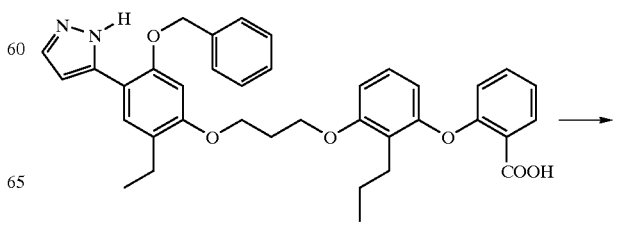

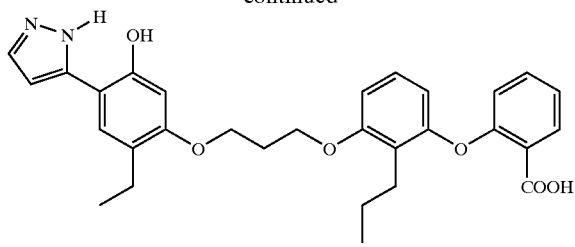

C. Preparation of 2-(3-{3-[2-ethyl-5-hydroxy-4-(2H-pyrazol-3-yl)phenoxy]propoxy}-2-propylphenoxy)benzoic acid.

A solution of 2-(3-{3-[5-benzyloxy-2-ethyl-4-(2H-pyrazol-3-yl)phenoxy]propoxy}-2-propylphenoxy)benzoic acid (300 mg, 0.490 mmol) in ethanethiol (2.5 mL) was treated with boron trifluoride etherate (2 mL) at room temperature for 3 h, at which time an additional portion of boron trifluoride etherate (1 mL) was added and stirring resumed for an additional 1 h. The mixture was diluted with diethyl ether and water. The organic layer was separated, washed with water, dried (sodium sulfate), filtered, and concentrated in vacuo. Chromatography (silica gel, 15% ethyl acetate/85% hexane to 60% ethyl acetate/40% hexane) of the residue provided 60 mg (24%) of the title compound as a white solid. $^1$H NM (CDCl$_3$) δ 8.23 (d, J=8Hz, 1H), 7.61 (s, 1H), 7.42 (t, J=7 Hz, 1H), 7.30 (s, 1H), 7.19 (d, J=8 Hz, 1H), 7.15 (d, J=8 Hz, 1H), 6.81 (d, J=8 Hz, 1H), 6.69 (d, J=8 Hz, 1H), 6.61 (s, 1H), 6.60 (d, J=8 Hz, 1H), 6.54 (s, 1H), 4.20 (m, 4H), 2.58 (m, 4H), 2.33 (quintet, J=6 Hz, 2H), 1.48 (hextet, J=8 Hz, 2H), 1.17 (t, J=8 Hz, 3H), 0.86 (t, J=7 Hz, 3H); TOF MS ES$^+$ exact mass calculated for C$_{30}$H$_{33}$N$_2$O$_6$ (p+1): m/z=517.2339. Found: 517.2334. IR (CHCl$_3$, cm$^{-1}$) 2965, 1738, 1454. Anal. Calcd for C$_{30}$H$_{32}$N$_2$O$_6$: C, 69.75; H, 6.24; N, 5.42. Found: C, 69.73; H, 6.33; N, 5.25.

Example 5
Preparation of 2-{3-[3-(2-Ethyl-5- -4-isoxazol-5-yl-phenoxy)propoxy]-2-propylphenoxy}benzoic acid.

A. Preparation of 2-{3-[3-(5-benzyloxy-2-ethyl-4-isoxazol-5-yl-phenoxy)propoxy]-2-propylphenoxy}benzoic acid methyl eater.

A mixture of 2-(3-{3-[5-benzyloxy-4-(3-dimethylaminoacryloyl)-2-ethylphenoxy]propoxy}-2-propylphenoxy)benzoic acid methyl ester (280 mg, 0.43 mmol), hydroxylamine hydrochloride (75 mg, 1.1 mmol), and water (1 mL) in methanol (4 mL) was heated at reflux for 2 h. The mixture was cooled to room temperature and diluted with diethyl ether and water. The organic layer was separated, washed with saturated sodium chloride solution, dried (sodium sulfate), filtered, and concentrated in vacuo. Chromatography (silica gel, 10% ethyl acetate/90% hexane) of the residue provided 202 mg (76%) of the title compound as a white solid. $^1$H NMR (CDCl$_3$) δ 8.20 (d, J=2 Hz, 1H), 7.88 (dd, J=9, 2 Hz, 1H), 7.79 (s, 1H), 7.40 (m, 7H), 7.08 (m, 2H), 6.68 (d, J=8 Hz, 1H), 6.59 (8, 1H), 6.58 (s, 1H), 6.43 (d, J=8 Hz, 1H), 5.15 (s, 2H), 4.21 (t, J=6 Hz, 4H), 3.82 (s, 3H), 2.65 (m, 4H), 2.33 (quintet, J=6 Hz, 4H), 1.56 (hextet, J=8 Hz, 2H), 1.20 (t, J=7 Hz, 3H), 0.90 (t, J=7 Hz, 3H); TOF MS ES$^+$ exact mass calculated for C$_{38}$H$_{40}$NO$_7$ (p+1): m/z=622.2805. Found: 622.2817. IR (CHCl$_3$, cm$^{-1}$) 2964, 1720, 1461. Anal. Calcd for C$_{38}$H$_{39}$NO$_7$: C, 73.41; H, 6.32; N, 2.25. Found: C, 73.20; H, 6.34; N, 2.27.

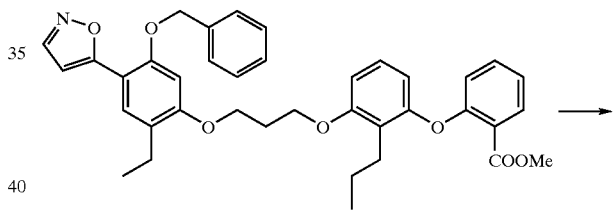

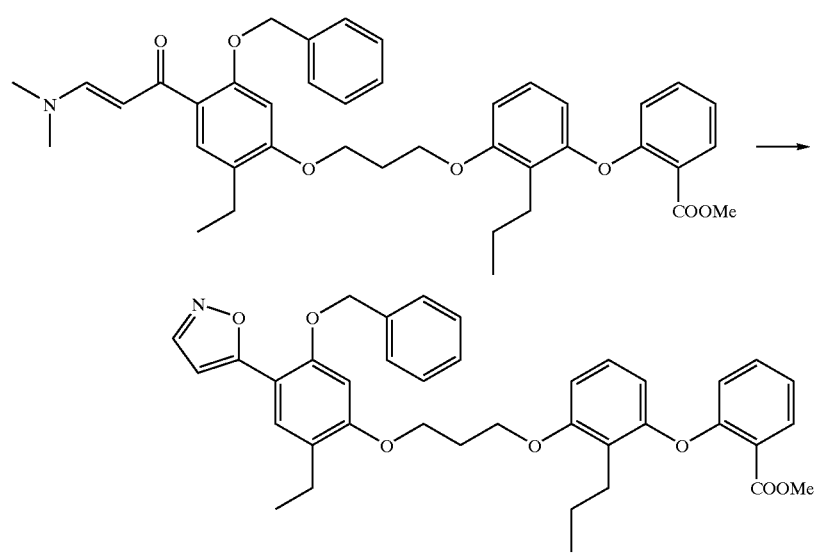

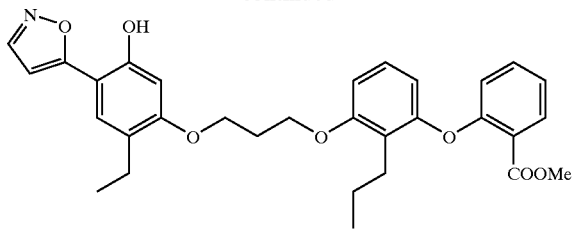

B. Preparation of 2-{3-[3-(2-ethyl-5-hydroxy-4-isoxazol-5-yl-phenoxy)propoxy]-2-propylphenoxy}benzoic acid methyl ester.

A solution of 2-{3-[3-(5-benzyloxy-2-ethyl-4-isoxazol-5-yl-phenoxy)propoxy]-2-propylphenoxy}benzoic acid methyl ester (180 mg, 0.289 mmol) in ethanethiol (5 mL) was treated with boron trifluoride etherate (1.5 mL) at room temperature for 2 h, at which time an additional portion of boron trifluoride etherate (0.5 mL) was added and stirring resumed for an additional 1 h. The mixture was diluted with diethyl ether and water. The organic layer was separated, washed once with saturated sodium bicarbonate solution, once with saturated sodium chloride solution, dried (sodium sulfate), filtered, and concentrated in vacuo. Chromatography (silica gel, 15% ethyl acetate/85% hexane) of the residue provided 94 mg (61%) of the title compound as a colorless oil. $^1$H NMR (CDCl$_3$) δ 8.28 (d, J=1 Hz, 1H), 7.88 (dd, J=8, 2 Hz, 1H), 7.38 (t, J=8 Hz, 1H), 7.36 (s, 1H), 7.08 (t, J=8 Hz, 1H), 7.05 (d, J=8 Hz, 1H), 6.81 (d, J=8 Hz, 1H), 6.67 (d, J=8 Hz, 1H), 6.50 (s, 1H), 6.45 (s, 1H), 6.43 (d, J=8 Hz, 1H), 4.20 (m, 4H), 3.83 (s, 3H), 2.62 (m, 4H), 2.34 (quintet, J=6 Hz, 2H), 1.54 (hextet, J=8 Hz, 2H), 1.18 (t, J=8 Hz, 3H), 0.90 (t, J=7 Hz, 3H); TOF MS ES$^+$ exact mass calculated for C$_{31}$H$_{34}$NO$_7$ (p+1): m/z=532.2335. Found: 532.2335. IR (CHCl$_3$, cm$^{-1}$) 2964, 1715, 1601, 1461. Anal. Calcd for C$_{31}$H$_{33}$NO$_7$: C, 70.04; H, 6.26; N, 2.63. Found: C, 70.13; H, 6.35; N, 2.63.

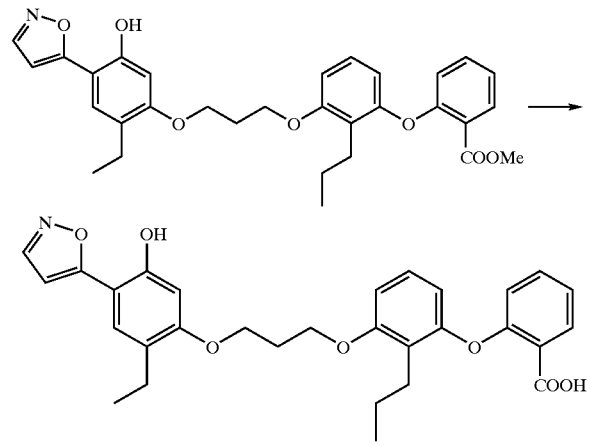

C. Preparation of 2-{3-[3-(2-ethyl-5-hydroxy-4-isoxazol-5-yl-phenoxy)propoxy]-2-propylphenoxy}benzoic acid.

To a solution of 2-{3-[3-(2-ethyl-5-hydroxy-4-isoxazol-5-yl-phenoxy)propoxy]-2-propylphenoxy}benzoic acid methyl ester (94 mg, 0.18 mmol) in methanol (3 mL) was added 1 M lithium hydroxide solution (1 mL) and the resulting mixture warmed at 60° C. for 3 h. The mixture was cooled to room temperature and concentrated in vacuo. The aqueous residue was diluted with water and the pH adjusted to ~4. The mixture was extracted three times with methylene chloride. The combined organic extracts were dried (sodium sulfate), filtered, and concentrated in vacuo to provide 12 mg (13%) of the title compound as an off-white amorphous solid. $^1$H NMR (CDCl$_3$) δ 8.26 (s, 1H), 8.20 (dd, J=8, 1 Hz, 1H), 7.49 (t, J=6 Hz, 1H), 7.36 (s, 1H), 7.18 (d, J=8 Hz, 1H), 7.15 (d, J=8 Hz, 1H), 7.02 (bs, 1H), 6.80 (d, J=8 Hz, 1H), 6.69 (d, J=8 Hz,.1H), 6.60 (d, J=8 Hz, 1H), 6.50 (s, 1H), 6.46 (s, 1H), 4.22 (t, J=6 Hz, 2H), 4.19 (t, J=6 Hz, 2H); 2.57 (m, 4H), 2.34 (quintet, J=6 Hz, 2H), 1.47 (hextet, J=8 Hz, 2H), 1.16 (t, J=8 Hz, 3H), 0.85 (t, J=7 Hz, 3H); TOS MS ES$^+$ exact mass calculated for C$_{30}$H$_{32}$NO7 (p+1): m/z=518.2179. Found: 518.2175. Anal. Calcd for C$_{30}$H$_{31}$NO$_7$: C, 69.62; H, 6.04; N, 2.71. Found: C, 69.57; H, 6.15; N, 2.74.

Example 6

Preparation of 2-(3-{3-[12-Ethyl-5-hydroxy-4-(3H-[1,2,3]triazol-4-yl)phenoxylpropoxy}-2-propyl-phenoxy)benzoic acid.

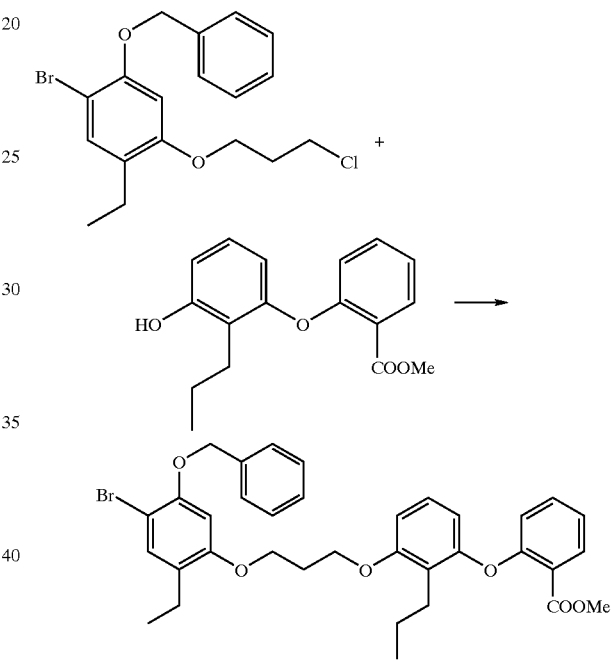

A. Preparation of 2-{3-[3-(5-benzyloxy-4-bromo-2-ethylphenoxy)propoxy]-2-propylphenoxy}-benzoic acid methyl ester.

A mixture of 5-benzyloxy-4-bromo-1-(3-chloropropoxy)-2-ethylbenzene (1.19 g, 3.11 mmol), 2-(3-hydroxy-2-propylphenoxy)benzoic acid methyl ester (0.89 g, 3.1 mmol), potassium carbonate (1.29 g, 9.34 mmol), potassium iodide (0.52 g, 3.1 mmol), and methyl sulfoxide (2 mL) in 2-butanone (20 mL) was heated at reflux for 48 h. The mixture was cooled to room temperature, diluted with diethyl ether, and washed once with water. The organic layer was dried (sodium sulfate), filtered, and concentrated in vacuo. Chromatography (silica gel, 6% ethyl acetate/94% hexane) of the residue provided 1.34 g (68%) of the title compound as a colorless oil. $^1$H NMR (CDCl$_3$) δ 7.91 (dd, J=8, 2 Hz, 1H), 7.50 (d, J=7 Hz, 2H), 7.38 (m, 5H), 7.15 (d, J=8 Hz, 1H), 7.10 (d, J=3 Hz, 1H), 6.83 (d, J=8 Hz, 1H), 6.71 (d, J=8 Hz, 1H), 6.55 (s, 1H), 6.48 (, J=8 Hz, 1H), 5.16 (s, 2H), 4.21 (t, J=6 Hz, 2H), 4.15 (t, J=6 Hz, 2H), 3.83 (s, 3H), 2.68 (t, J=8 Hz, 2H), 2.58 (q, J=7 Hz, 2H), 2.31 (quintet, J=6 Hz, 2H), 1.58 (hextet, J=6 Hz, 2H), 1.17 (t, J=7 Hz, 3H), 0.93 (t, J=7 Hz, 3H).

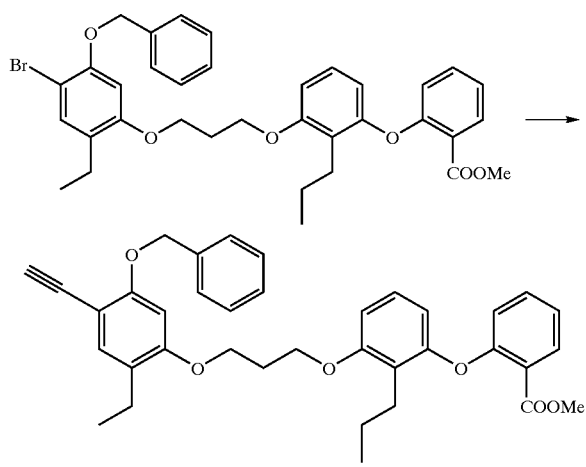

B. Preparation of 2-{3-[3-(5-benzyloxy-2-ethyl-4-ethynylphenoxy)propxy]-2-propyl-phenoxy}benzoic acid methyl eater.

A mixture of 2-{3-[3-(5-benzyloxy-4-bromo-2-ethylphenoxy)propoxy]-2-propylphenoxy}-benzoic acid methyl ester (1.50 g, 2.37 mmol), tri-n-butylethynyltin (0.82 mL, 2.8 mmol), and tetrakis(triphenylphosphine)palladium (0) (1.0 g, 0.95 mmol) in N,N-dimethylformamide (25 mL) was purged with argon and heated in a sealed tube at 120° C. for 24 h. The mixture was cooled to room temperature and filtered. The filtrate was diluted with ethyl acetate, washed four times with water, once with saturated sodium chloride solution, dried (sodium sulfate), filtered, and concentrated in vacuo. Chromatography (silica gel, 10% ethyl acetate/90% hexane) of the residue provided 532 mg (39%) of the title compound as a brown oil. $^1$H NMR (CDCl$_3$) δ 7.88 (dd, J=8, 2 Hz, 1H), 7.79 (s, 1H), 7.20–7.50 (m, 6H), 7.10 (d, J=8 Hz, 1H), 7.05 (d, J=8 Hz, 1H), 6.80 (d, J=8 Hz, 1H), 6.66 (d, J=8 Hz, 1H), 6.43 (m, 2H), 5.16 (s, 2H), 4.17 (t, J=6 Hz, 2H), 4.11 (t, J=6 Hz, 2H), 3.83 (s, 3H), 3.23 (s, 1H), 2.64 (t, J=8 Hz, 2H), 2.53 (q, J=7 Hz, 2H), 2.27 (quintet, J=6 Hz, 2H), 1.53 (m, 2H), 1.13 (t, J=7 Hz, 3H), 0.89 (t, J=7 Hz, 3H); TOF MS ES$^+$ exact mass calculated for C$_{37}$H$_{39}$O$_6$ (p+1): m/z= 579.2747. Found: 579.2739.

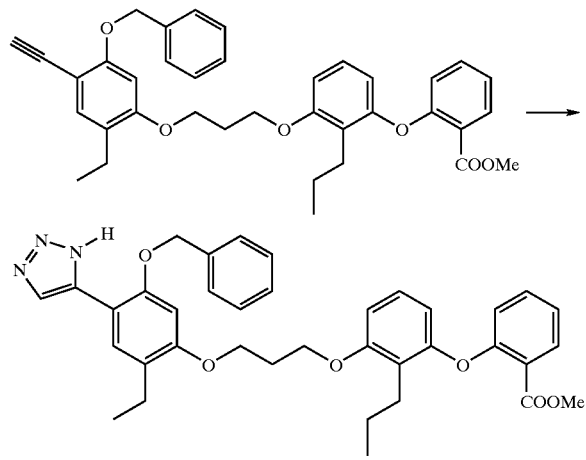

C. Preparation of 2-(3-{3-[5-benzyloxy-2-ethyl-4-(3H-[1,2,3]triazol-4-yl)phenoxy]-propoxy}-2-propylpbonoxy) benzoic acid methyl ester.

A mixture of 2-{3-[3-(5-benzyloxy-2-ethyl-4-ethynylphenoxy)propoxy]-2-propyl-phenoxy}benzoic acid methyl ester (517 mg, 0.893 mmol) and trimethylsilyl azide (3.0 mL, 18 mmol) was heated in toluene (20 mL) in a sealed tube at 130° C. for 120 h. The mixture was cooled to room temperature and concentrated in vacuo. Chromatography (silica gel, 10% ethyl acetate/90% hexane to 50% ethyl acetate/50% hexane) of the residue provided 347 mg (88% based upon recovered starting material) of the title compound as a brown solid. $^1$H NMR (CDCl$_3$) δ 8.10 (bs, 1H), 7.89 (dd, J=8, 2 Hz, 1H), 7.76 (s, 1H), 7.40 (m, 7H), 7.10 (d, J=8 Hz, 1H), 7.05 (d, J=8 Hz, 1H), 6.79 (d, J=8 Hz, 1H), 6.67 (d, J 8 Hz, 1H), 6.62 (s, 1H), 6.43 (d, J=8 Hz, 1H), 5.18 (s, 2H), 4.21 (m, 4H), 3.82 (s, 3H), 2.65 (m, 4H), 2.32 (quintet, J=6 Hz, 2H), 1.56 (hextet, J=8 Hz, 2H), 1.21 (t, J=8.Hz, 3H), 0.90 (t, J=7 Hz, 3H); TOF MS ES$^+$ exact mass calculated for C$_{37}$H$_{40}$N$_3$O$_6$ (p+1) m/z=622.2917. Found: 622.2946. IR (CHCl$_3$, cm$^{-1}$) 3400, 1721, 1602, 1453. Anal. Calcd for C$_{37}$H$_{39}$N$_3$O$_6$: C, 71.48; H, 6.32; N, 6.76. Found: C, 70.28; H, 6.07; N, 6.54.

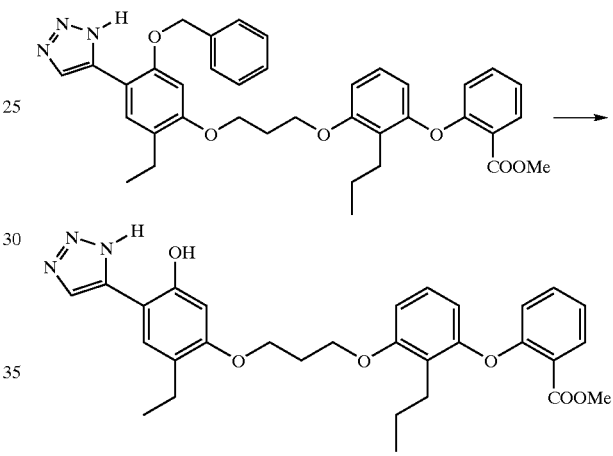

D. Preparation of 2-(3-{3-[2-ethyl-5-hydroxy-4-(3H-[1,2,3]triazol-4-yl)phenoxy]-propoxy}-2-propyl-phenoxy)benzoic acid methyl ester.

A solution of 2-(3-{3-[5-benzyloxy-2-ethyl-4-(3H-[1,2,3]triazol-4-yl)phenoxy]propoxy}-2-propylphenoxy)benzoic acid methyl ester (330 mg, 0.531 mmol) in ethanethiol (9 mL) was treated with boron trifluoride etherate (2.0 mL, 16 mmol) for 1 h at room temperature and then with an additional portion of boron trifluoride etherate (1.0 mL) for 1 h. The mixture was diluted with diethyl ether and water. The organic layer was washed once with saturated sodium bicarbonate solution, once with saturated sodium chloride solution, dried (sodium sulfate), filtered, and concentrated in vacuo. Chromatography (silica gel, 30% ethyl acetate/70% hexane to 50% ethyl acetate/50% hexane) of the residue provided 180 mg (63%) of the title compound as a brown solid. $^1$H NMR (CDCl$_3$) δ 7.97 (s, 1H), 7.88 (dd, J=8, 2 Hz, 1H), 7.37 (t, J=8 Hz, 1H), 7.31 (s, 1H), 7.10 (d, J=8 Hz, 1H), 7.05 (d, J=8 Hz, 1H), 6.81 (d, J=8 Hz, 1H), 6.67 (d, J=8 Hz, 1H), 6.59 (s, 1H), 6.43 (d, J=8 Hz, 1H), 4.20 (m, 4H), 3.83 (s, 3H), 2.63 (m, 4H), 2.34 (quintet, J=6 Hz, 2H), 1.55 (hextet, J=8 Hz, 2H), 1.19 (t, J=8 Hz, 3H), 0.90 (t, J=7 Hz, 3H); TOF MS ES$^+$ exact mass calculated for C$_{30}$H$_{34}$N$_3$O$_6$ (p+1): m/z=532.2447. Found: 532.2466. IR (CHCl$_3$, cm$^{-1}$) 2964, 1718, 1453. Anal. Calcd for C$_{30}$H$_{33}$N$_3$O$_6$: C, 67.78; H, 6.26; N, 7.90. Found: C, 66.80; H, 6.02; N, 7.53.

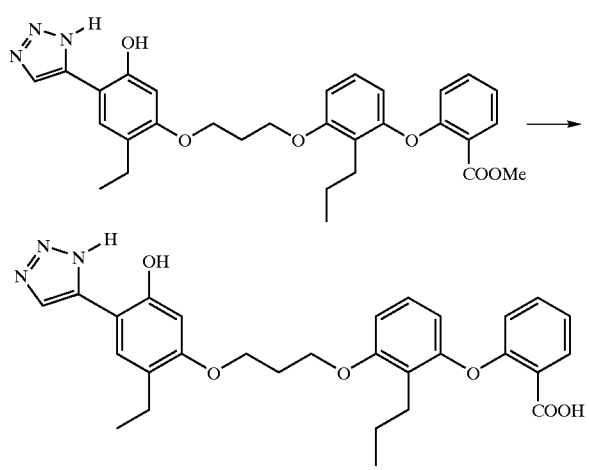

E. Preparation of 2-(3-{3-[2-ethyl-5-hydroxy-4-(3H-1,2,3] triazol-4-yl)phenoxy]-propoxy}-2-propyl]phenoxy)benzoic acid.

A solution of 2-(3-{3-[2-ethyl-5-hydroxy-4-(3H-[1,2,3] triazol-4-yl)phenoxy]propoxy}-2-propylphenoxy)benzoic acid methyl ester (160 mg, 0.30 mmol) in methanol (5 mL) was treated 1 N lithium hydroxide solution (1.5 mL) at 60° C. for 3.5 h. The mixture was cooled to room temperature, diluted with water, and adjusted to ~pH 4. The resulting mixture was extracted three times with methylene chloride. The combined organic extracts were dried (sodium sulfate), filtered, and concentrated in vacuo to provide 134 mg (86%) of the title compound as a tan solid. $^1$H NMR (DMSO-d) δ 14.98 (bs, 1H), 12.80 (bs, 1H), 10.02 (bs, 1H), 8.17 (bs, 1H), 7.77 (dd, J=7, 2 Hz, 1H), 7.60 (bs, 1H), 7.47 (t, J=8 Hz, 1H), 7.18 (t, J=8 Hz, 1H), 7.14 (t, J=8 Hz, 1H), 6.82 (d, J=8 Hz, 1H), 6.68 (d, J=8 Hz, 1H), 6.57 (s, 1H), 6.35 (d, J=8 Hz, 1H), 4.22 (t, J=6 Hz, 2H), 4.15 (t, J=6 Hz, 2H), 2.54 (m, 4H), 2.25 (quintet, J=6 Hz, 2H), 1.45 (hextet, J=8 Hz, 2H), 1.11 (t, J=7 Hz, 3H), 0.81 (t, J=7 Hz, 3H); TOF MS ES$^+$ exact mass calculated for $C_{29}H_{32}N_3O_6$ (p+1): m/z=518.2291. Found: 518.2302. IR (CHCl$_3$, cm$^{-1}$) 2965, 1738, 1454. Anal. Calcd for $C_{29}H_{31}N_3O_6$: C, 67.30; H, 6.04; N, 8.12. Found: C, 67.15; H, 5.98; N, 7.93.

Example 7

Preparation of 2-{3-[3-(2-Ethyl-5-hydroxy-4-pyrrol-1-yl-phenoxy)propoxy]-2-propyl-phenomy}benzoic acid methyl ester.

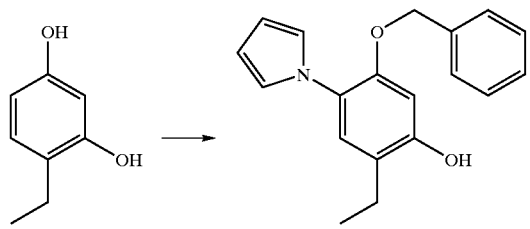

A. Preparation of 5-benzyloxy-2-ethyl-4-pyrrol-1-yl-phenol.

To a mixture of potassium nitrosodisulfonate (40.0 g, 149 mmol) and potassium hydrogen phosphate (10 g) in water (1.2 L) at room temperature was added a solution of 4-ethylbenzene-1,3-diol (10.0 g, 2.37 mmol) and potassium hydrogen phosphate (10.5 g) in water (150 mL). The mixture was stirred for 15 min and adjusted to pH ~3. The solution was extracted three times with diethyl ether. The organic layer was dried (sodium sulfate), filtered, and concentrated in vacuo. The residue was dissolved in acetonitrile (70 mL) and treated at room temperature with 65% 3-pyrroline (12 mL). The resulting mixture was stirred for 1 h and concentrated in vacuo, dissolved in ethyl acetate and hexane, and filtered down a short column of silica gel. The resulting solution was concentrated in vacuo. The residue was dissolved in N,N-dimethylformamide (10 mL) and treated with benzyl bromide (0.85 mL, 7.1 mmol) and potassium carbonate (960 mg, 6.9 mmol) at room temperature for 15 h. The mixture was diluted with ethyl acetate, washed four times with water, once with saturated sodium chloride solution, dried (sodium sulfate), filtered, and concentrated in vacuo. Chromatography (silica gel, ethyl acetate/hexane gradient) of the residue provided 316 mg (2%) of the title compound. TOF MS ES$^+$ exact mass calculated for $C_{19}H_{20}NO_2$ (p+1): m/z=294.1494. Found: 294.1471.

B. Preparation of 1-[2-benzyloxy-4-(3-chloropropoxy)-5-ethylphenyl]-1H-pyrrole.

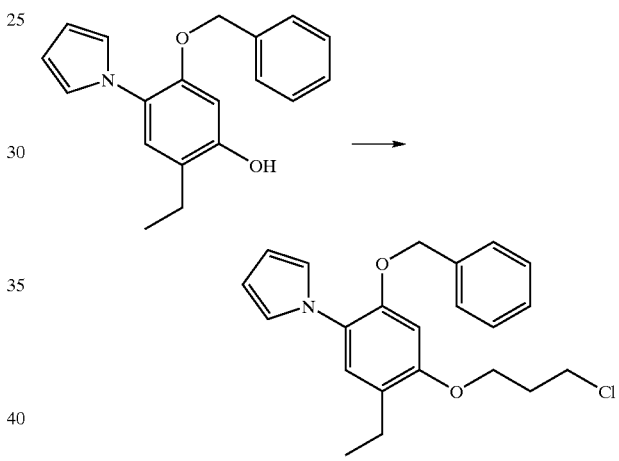

A mixture of 5-benzyloxy-2-ethyl-4-pyrrol-1-yl-phenol (316 mg, 1.08 mmol), potassium carbonate (223 mg, 1.62 mmol), and 1-bromo-3-chloropropane (0.16 mL, 1.6 mmol) in N,N-dimethylformamide (5 mL) was stirred at room temperature for 18 h. The mixture was diluted with ethyl acetate and water, washed four times with water, once with saturated sodium chloride solution, dried (sodium sulfate), filtered, and concentrated in vacuo. Chromatography (silica gel, 5% ethyl acetate/95% hexane) of the residue provided 314 mg (79%) of the title compound as a colorless oil. TOF MS ES$^+$ exact mass calculated for $C_{22}H_{25}NClO_2$ (p+1): m/z=370.1574. Found: 370.1548.

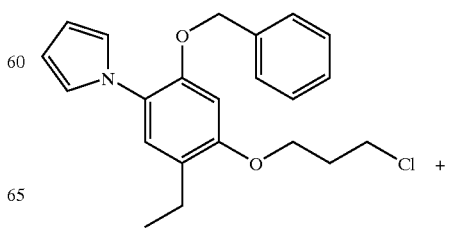 +

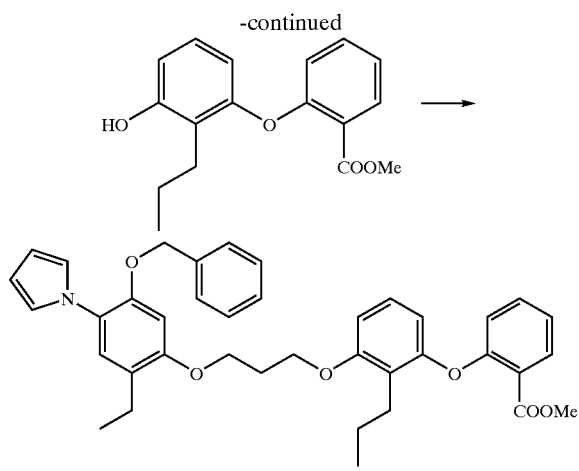

C. Preparation of 2-{3-[3-(5-benzyloxy-2-ethyl-4-pyrrol-1-yl-phenoxy)propoxy]-2-propylphenoxy}benzoic acid methyl ester.

A mixture of 1-[2-benzyloxy-4-(3-chloropropoxy)-5-ethylphenyl]-1H-pyrrole (310 mg, 0.85 mmol) and sodium iodide (140 mg, 0.94 mol) in 2-butanone (5 mL) was heated at reflux for 6 h. The mixture was cooled to room temperature, filtered, and concentrated in vacuo. The residue was dissolved in N,N-dimethylformamide (7 mL) and treated with 2-(3-hydroxy-2-propylphenoxy)benzoic acid methyl ester (242 mg, 0.85 mmol.) and potassium carbonate (129 g, 93 mmol) at room temperature for 15 h. The mixture was diluted with ethyl acetate and water, washed four times with water, once with saturated sodium chloride solution, dried (sodium sulfate), filtered; and concentrated in vacuo. Chromatography (silica gel, 5% ethyl acetate/95% hexane) of the residue provided 196 mg (37%) of the title compound as a colorless oil. $^1$H NMR (CDCl$_3$) δ 7.86 (dd, J=8, 2 Hz, 1H), 7.37 (dt, J=8, 2 Hz, 1H), 7.30 (m, 5H), 7.07 (m, 3H), 6.84 (m, 2H), 6.79 (d, J=8 Hz, 1H), 6.65 (d, J=8 Hz, 1H), 6.58 (s, 1H), 6.42 (d, J=8 Hz, 1H), 6.29 (m, 2H), 4.92 (s, 2H), 4.17 (t, J=6 Hz, 2H), 4.15 (t, J=6 Hz, 2H), 3.83 (s, 3H), 2.65 (t, J=8 Hz, 2H),. 2.58 (q, J=7 Hz, 2H), 2.30 (quintet, J=6 Hz, 2H), 1.55 (hextet, J=8 Hz, 2H), 1.16 (t, J=7 Hz, 3H), 0.80 (t, J=7 Hz, 3H); TOF MS ES$^+$ exact mass calculated for C$_{39}$H$_{42}$NO$_6$ (p+1): m/z=620.3012. Found: 620.3021.

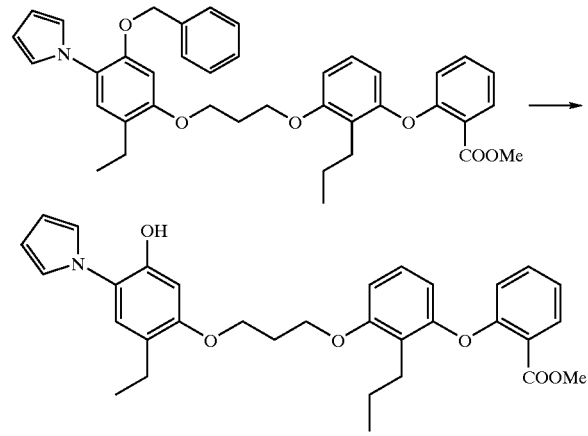

D. Preparation of 2-{3-[3-(2-ethyl-5-hydroxy-4-pyrrol-1-yl-phenoxy)propoxy]-2-propyl-phenoxy}benzoic acid methyl ester.

A solution of 2-{3-[3-(5-benzyloxy-2-ethyl-4-pyrrol-1-yl-phenoxy)propoxy]-2-propylphenoxy}benzoic acid methyl ester (195 mg, 0.315 mmol) in ethanethiol (5 mL) was treated with boron trifluoride etherate (1.3 mL, 9.5 mmol) at room temperature for 2.5 h. The mixture was diluted with diethyl ether and water. The organic layer was washed with saturated sodium bicarbonate solution, dried (sodium sulfate), filtered, and concentrated in vacuo. Chromatography (silica gel, 10% ethyl acetate/90% hexane) of the residue provided 39 mg (23%) of the title compound as a colorless oil. $^1$H NMR (CDCl$_3$) δ 7.89 (d, J=8 Hz, 1H), 7.37 (t, J=8 Hz, 1H), 7.07 (m, 2H), 6.98 (s, 1H), 6.68 (m, 3H), 6.65 (d, J=8 Hz, 1H), 6.57 (s, 1H), 6.42 (d, J=8 Hz, 1H), 6.35 (m, 2H), 5.04 (bs, 1H), 4.19 (m, 2H), 3.83 (s, 3H), 2.64 (t, J=8 Hz, 2H), 2.58 (g, J=7 Hz, 2H), 2.32 (quintet, J=6 Hz, 2H), 1.55 (m, 2H), 1.14 (t, J=7 Hz, 3H), 0.90 (t, J=7 Hz, 3H); TOF MS ES$^+$ exact mass calculated for C$_{32}$H$_{36}$NO$_6$ (p+1): m/z=530.2543. Found: 530.2516.

Example 8

Preparation of 2-(3-{3-[4-(3-Bromo-[1,2,4]thiadiazol-5-yl)-2-ethyl-5-hydroxyphenoxy]-propoxy}-2-propylphonomy) benzoic acid.

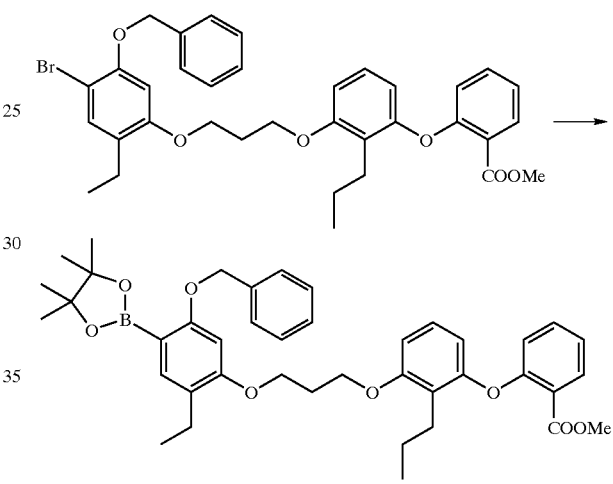

A. Preparation of 2-(3-{3-[5-benzyloxy-2-ethyl-4-(4,4,5,5-tetramethyl-[1,3,2]diaxabarolan-2-yl)phenoxy]propoxy}-2-propylphenoxy)benzoic acid methyl ester.

A mixture of 2-{3-[3-(5-benzyloxy-4-bromo-2-ethylphenoxy)propoxy]-2-propylphenoxy}-benzoic acid methyl ester (8.30 g, 13.1 mmol), triethylamine (5.2 mL, 39 mmol), and PdCl$_2$(dppf) (320 mg, 0.39 mmol) in de-oxygenated toluene (80 mL) was treated with a 1 M solution of 4,4,5,5-tetramethyl-[1,3,2]dioxaborolane in tetrahydrofuran (20 mL, 20 mmol) and heated at reflux for 6 h. The mixture was filtered down a short column of silica gel and the filtrate concentrated in vacuo. Chromatography (silica gel, 35% ethyl acetate/65% hexane) of the residue provided a dark oil that was subjected to further chromatography (silica gel, hexane to 30% ethyl acetate/70% hexane) to give 7.70 g (84%) of the title compound. $^1$H NMR (CDCl$_3$) δ 7.86 (dd, J=8, 2 Hz, 1H), 7.60 (d, J=8 Hz, 2H), 7.47 (s, 1H), 7.34 (m, 3H), 7.24 (t, J=8 Hz, 1H), 7.09 (d, J=9 Hz, 1H), 7.04 (d, J=9 Hz, 1H), 6.79 (d, J=9 Hz, 1H), 6.66 (d, J=9 Hz, 1H), 6.47 (s, 1H), 6.43 (d, J=8 Hz, 1H), 5.07 (s, 2H), 4.18 (m, 4H), 3.81 (s, 3H), 2.64 (t, J=8 Hz, 2H), 2.56 (q, J=7 Hz, 2H), 2.30 (quintet, J=6 Hz, 2H), 1.53 (hextet, J=8 Hz, 2H), 1.34 (s, 12H),1.14 (t, J=7 Hz, 3H), 0.89 (t, J=7 Hz, 3H); TOF MS ES$^+$ exact mass calculated for C$_{41}$H$_{53}$NBO$_8$ (p+NH$_4$): m/z=698.3864. Found: 698.3889. IR (CHCl$_3$, cm$^{-1}$) 2964, 1720, 1604, 1453. Anal. Calcd for C$_{41}$H$_{49}$BO$_8$: C, 72.35; H, 7.26. Found: C, 72.30; H, 7.12.

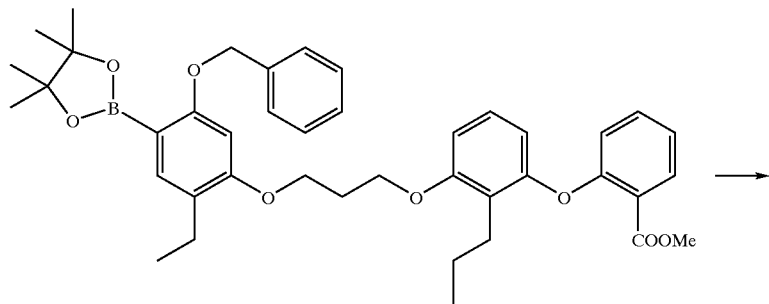

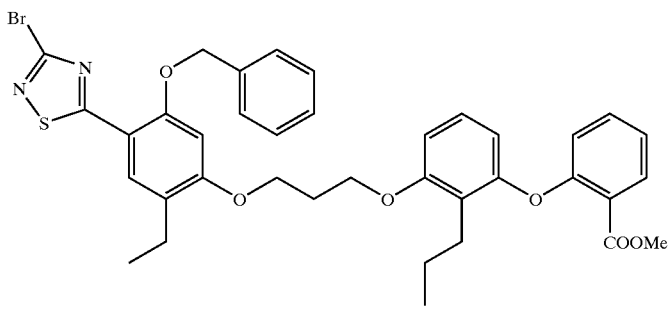

B. Preparation of 2-(3-{3-[5-benzyloxy-4-(3-bromo-[1,2,4]thiadiazol-5-yl)-2-ethyl-phenoxy]propoxy}-2-propylphenoxy)benzoic acid methyl ester.

A mixture of 2-(3-{3-[5-benzyloxy-2-ethyl-4-(4,4,5,5-tetramethyl-[1,3,2]dioxaborolan-2-yl)phenoxy]propoxy}-2-propylphenoxy)benzoic acid methyl ester (310 mg, 0.46 mmol), 3-bromo-5-chloro-1,2,4-thiadiazole (120 mg, 0.60 mmol), cesium carbonate (300 mg, 0.92 mmol), and PdCl$_2$(dppf) (20 mg, 0.024 mmol) in de-oxygenated toluene (10 mL) was heated at 100° C. for 15 h. The mixture was diluted with a solution of 35% ethyl acetate/65% hexane and filtered down a short column of silica gel. The filtrate was concentrated in vacuo. Chromatography (silica gel, hexane to 30% ethyl acetate/70% hexane) of the residue provided 232 mg (70%) of the title compound. $^1$H NMR (CDCl$_3$) δ 8.13 (s, 1H), 7.87 (dd, J=8, 2 Hz, 1H), 7.44 (m, 2H), 7.37 (m, 4H), 7.08 (t, dJ=8, 1 Hz, 1H), 7.04 (d, J=9 Hz, 1H), 6.78 (d, J=9 Hz, 1H), 6.66 (d, J=9 Hz, 1H), 6.55 (s, 1H), 6.43 (d, J=8 Hz, 1H), 5.28 (s, 2H), 4.21 (t, J=6 Hz, 2H), 4.19 (t, J=6 Hz, 2H), 3.81 (s, 3H), 2.62 (m, 4H), 2.34 (quintet, J=6 Hz, 2H), 1.55 (hextet, J=8 Hz, 2H), 1.17 (t, J=7 Hz, 3H), 0.88 (t, J=7 Hz, 3H); MS ES$^+$ m/e 717, 719.

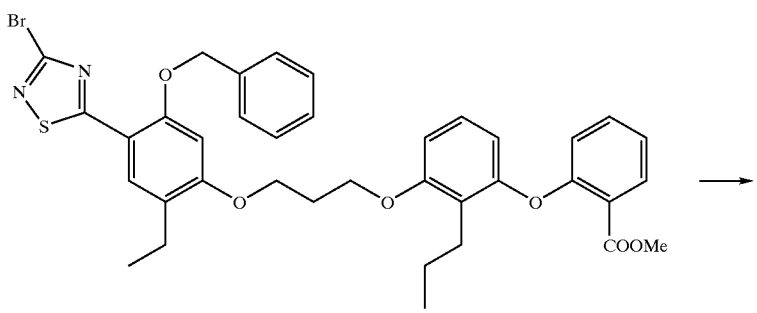

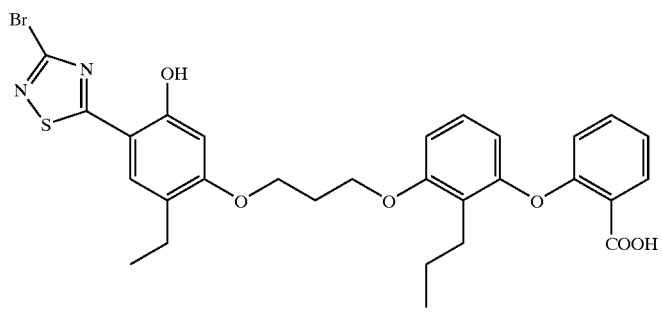

C. Preparation of 2-(3-{3-[4-(3-bromo-[1,2,4]thiadiazol-5-yl)-2-ethyl-5-hydroxyphenoxy]propoxy}-2-propylphenoxy)benzoic acid.

A solution of 2-(3-{3-[5-benzyloxy-4-(3-bromo-[1,2,4]thiadiazol-5-yl)-2-ethyl-phenoxy]propoxy}-2-propylphenoxy}benzoic acid methyl ester (230 mg, 0.31 mmol) in ethanethiol (4 mL) was treated with boron trifluoride etherate (0.32 mL, 2.5 mmol) at room temperature for 6 h, at which time an additional portion of boron trifluoride etherate was added and stirring continued for 7 h. The reaction mixture was diluted with water, concentrated in vacuo, and extracted with diethyl ether. The residue was dissolved in methanol (5 mL) and treated with 1 N lithium hydroxide solution (2 mL) at 65° C. for 1 h. The mixture was concentrated in vacuo and the residue diluted with water and adjusted to ~pH 3 with 1 N hydrochloric acid. The resulting precipitate was collected via vacuum filtration and dissolved in dilute aqueous base. Reverse phase chromatography (1:1 acetonitrile/water) provided 43 mg (23%) of the title compound as a yellow solid. $^1$H NMR (DMSO-d$_6$) δ 7.85 (s, 1H), 7.80 (dd, J=8, 2 Hz, 1H), 7.45 (m, 2H), 7.15 (m, 3H), 6.83 (d, J=9 Hz, 1H), 6.80 (d, J=9 Hz, 1H), 6.62 (s, 1H), 6.35 (d, J=9 Hz, 1H), 4.20 (m, 4H), 2.55 (m, 4H), 2.27 (quintet, J=5 Hz, 2H), 1.44 (hextet, J=8 Hz, 2H), 1.13 (t, J=7 Hz, 3H), 0.81 (t, J=7 Hz, 3H); MS ES$^+$ m/e 551 (p+NH$_4^+$–Br); IR (KBr, cm$^{-1}$) 2900, 1696, 1603, 1461. Anal. Calcd for C$_{29}$H$_{29}$BrN$_2$O$_6$S: C, 56.77; H, 4.76; N, 4.56. Found: C, 56.63; H, 4.72; N, 3.98.

Example 9

Preparation of 2-{3-[3-(2-Ethyl-5-hydroxy-4-thiophen-2-yl-phenoxy)propoxy]-2-propyl-phenoxy}benzoic acid sodium salt.

A. Preparation of 2-{3-[3-(2-ethyl-5-hydroxy-4-thiophen-2-yl-phenoxy)propoxy]-2-propylphenoxy}benzoic acid methyl ester.

A mixture of 2-(3-{3-[5-benzyloxy-2-ethyl-4-(4,4,5,5-tetramethyl-[1,3,2]dioxaborolan-2-yl)phenoxy]propoxy}-2-propylphenoxy)benzoic acid methyl ester (300 mg, 0.44 mmol), 2-bromothiophene (110 mg, 0.66 mmol), cesium carbonate (300 mg, 2.17 mmol), and PdCl$_2$(dppf) (20 mg, 0.024 mmol) in de-oxygenated toluene (10 mL) was heated at 105° C. for 66 h. The mixture was cooled to room temperature and concentrated in vacuo. The residue was dissolved in methylene chloride and filtered down a short column of silica gel. The filtrate was concentrated in vacuo. Chromatography (silica gel, 30% ethyl acetate/70% hexane) of the residue provided an oil that was dissolved in ethanethiol (4 mL) and treated with boron trifluoride etherate (0.44 mL, 3.4 mmol) at room temperature for 3 h. The mixture was diluted with water and extracted with diethyl ether. The organic layer was dried (sodium sulfate), filtered, and concentrated in vacuo. Chromatography (silica gel, hexane to 30% ethyl acetate/70% hexane) of the residue provided 120 mg (50%) of the title compound as a yellow film. $^1$H NMR (CDCl$_3$) δ 7.85 (dd, J=8, 2 Hz, 1H), 7.35 (t, J=8 Hz, 1H), 7.15 (d, J=7 Hz, 1H), 7.03–7.15 (m, 5H), 6.80 (d, J=9 Hz, 1H), 6.66 (d, J=9 Hz, 1H), 6.51 (s, 1H), 6.42 (d, J=8 Hz, 1H), 5.44 (bs, 1H), 4.18 (m, 4H), 3.82 (s, 3H), 2.62 (t, J=8 Hz, 2H), 2.58 (q, J=7 Hz, 2H), 2.54 (quintet, J=6 Hz, 2H), 1.52 (hextet, J=8 Hz, 2H), 1.16 (t, J=7 Hz, 3H), 0.90 (t, J=7 Hz, 3H); MS ES$^+$ m/e 545 (p–1).

B. Preparation of 2-{3-[3-(2-ethyl-5-hydroxy-4-thiophen-2-yl-phenoxy)propoxy]-2-propylphenoxy}benzoic acid sodium salt.

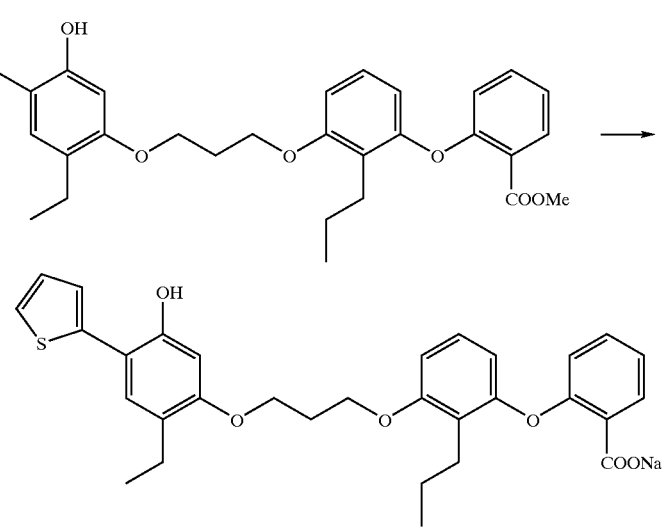

A solution of 2-{3-[3-(2-ethyl-5-hydroxy-4-thiophen-2-yl-phenoxy)propoxy]-2-propylphenoxy}benzoic acid methyl ester (120 mg, 0.22 mmol) in methanol (3 mL) was treated with 1 N lithium hydroxide solution (0.5 mL) at room temperature for 1 h and then with an additional portion of 1 N lithium hydroxide solution (0.75 mL) for 18 h. The mixture was heated at 50° C. then concentrated in vacuo. The residue was acidified with dilute hydrochloric acid and extracted with diethyl ether. The organic layer was washed once with water and concentrated in vacuo. The residue was diluted with 1 N sodium hydroxide solution (0.22 mL), diethyl ether, and toluene. The mixture was concentrated in vacuo, dissolved in methylene chloride, and concentrated in vacuo to provide 120 mg (98%) of the title compound as a green film. $^1$H NMR (DMSO-d$_6$) δ 7.71 (d, J=8 Hz, 1H), 7.42 (m, 2H), 7.31 (m, 2H), 7.10 (m, 2H), 6.99 (m, 1H), 6.76 (t, J=7 Hz, 2H), 6.52 (s, 1H), 6.30 (d, J=8 Hz, 1H), 4.16 (t, J=7 Hz, 2H), 4.07 (t, J=7 Hz, 2H), 2.50 (m, 4H), 2.20 (m, 2H), 1.40 (m, 2H), 1.06 (t, J=8 Hz, 3H), 0.77 (t, J=7 Hz, 3H); MS ES$^+$ m/e 533 (p+1–Na$^+$). IR (CHCl$_3$, cm$^{-1}$) 2900, 1738, 1604, 1454.

Example 10

Preparation of 2-(3-{3-[2-ethyl-5-hydroxy-4-(1-methyl-1H-pyrazol-4-yl)-phenoxy]propoxy}-2-propylphenoxy)benzoic acid.

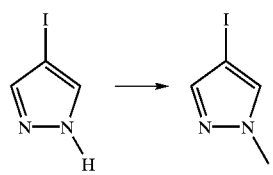

A. Preparation of 4-iodo-1-methylpyrazole (Known compound: RN 39806-90-1).

To a solution of 4-iodopyrazole (1.3 g, 6.8 mmol) in dioxane (10 mL) was added iodomethane (0.42 mL, 6.8 mmol) and the resulting mixture stirred at room temperature for 96 h. The mixture was concentrated in vacuo and the residue mixed with methylene chloride and filtered. The filtrate was concentrated in vacuo to provide 1.35 g (95%) of the title compound as a colorless oil. $^1$H NMR (CDCl$_3$) δ 7.47 (s, 1H), 7.38 (s, 1H), 3.90 (s, 3H).

B. Preparation of 2-(3-{3-[5-benzyloxy-2-ethyl-4-(1-methyl-1H-pyrazol-4-yl)phenoxy]-propoxy}-2-propylphenoxy)benzoic acid methyl ester.

A mixture of 2-(3-{3-[5-benzyloxy-2-ethyl-4-(4,4,5,5-tetramethyl-[1,3,2]dioxaborolan-2-yl)phenoxy]propoxy}-2-propylphenoxy)benzoic acid methyl ester (1.00 g, 1.47 mmol), 4-iodo-1-methylpyrazole (450 mg, 2.16 mmol), cesium carbonate (1.20 g, 3.62 mmol), and PdCl$_2$(dppf) (72 mg, 0.088 mmol) in de-oxygenated toluene (35 mL) was heated at 100° C. for 24 h. Additional portions of 4-iodo-1-methylpyrazole (~30 mg) and PdCl$_2$(dppf) (~30 mg) were added and heating continued at 100° C. for 40 h. The mixture was cooled to room temperature, concentrated in vacuo, diluted with methylene chloride, and filtered down a short plug of silica gel. The filtrate was concentrated in vacuo. Chromatography (silica gel, 35% ethyl acetate/65% hexane to 65% ethyl acetate/35% hexane) of the residue provided 710 mg (76%) of the title compound. $^1$H NMR (CDCl$_3$) δ 7.86 (dd, J=8, 2 Hz, 1H), 7.80 (s, 1H), 7.69 (s, 1H), 7.37 (m, 6H), 7.28 (s, 1H), 7.09 (d, J=9 Hz, 1H), 7.04 (d, J=9 Hz, 1H), 6.78 (d, J=9 Hz, 1H), 6.67 (d, J=9 Hz, 1H), 6.56 (s, 1H), 6.42 (d, J=8 Hz, 1H), 5.08 (s, 2H), 4.18 (t, J=6 Hz, 2H), 4.15 (t, J=6 Hz, 2H), 3.85 (s, 3H), 3.81 (s, 3H), 2.63 (t, J=8 Hz, 2H), 2.59 (q, J=7 Hz, 2H), 2.30 (quintet, J=6 Hz, 2H), 1.55 (hextet, J=8 Hz, 2H), 1.23 (t, J=7 Hz, 3H), 0.89 (t, J=7 Hz, 3H).

C. Preparation of 2-(3-{3-[2-ethyl-5-hydroxy-4-(1-methyl-1H-pyrazol-4-yl)-phenoxy]propoxy}-2-propylphenoxy)benzoic acid.

A solution of 2-(3-{3-[5-benzyloxy-2-ethyl-4-(1-methyl-1H-pyrazol-4-yl)phenoxy]propoxy}-2-propylphenoxy)benzoic acid methyl ester (710 mg, 1.12 mmol) in ethanethiol (5 mL) was treated with boron trifluoride etherate (1.42 mL, 11.2 mmol) at room temperature for 20 h. The reaction mixture was diluted with water, concentrated in vacuo, and extracted with diethyl ether. The organic layer was dried (magnesium sulfate), filtered, and concentrated in vacuo. The residue was triturated twice with hexane and the residue dissolved in methanol (5 mL). This solution was treated with 1 N lithium hydroxide solution (5 mL) at ~95° C. for 2 h. The mixture was concentrated in vacuo and the residue diluted with water, washed twice with diethyl ether, and the aqueous layer acidified with 1 N hydrochloric acid. The resulting solution was extracted with diethyl ether. The organic layer was dried (magnesium sulfate), filtered, and concentrated in vacuo. Chromatography (silica gel, 10% methanol/90% methylene chloride) provided 338 mg (57%) of the title compound as a tan foam. $^1$H NMR (DMSO-d$_6$) δ 12.85 (bs, 1H), 9.50 (bs, 1H), 7.98 (s, 1H), 7.78 (m, 2H), 7.48 (dt, J=8, 2 Hz, 1H), 7.44 (s, 1H), 7.18 (t, J=8 Hz, 1H), 7.13 (t, J=9 Hz, 1H), 6.79 (d, J=9 Hz, 1H), 6.77 (d, J=9 Hz, 1H), 6.53 (s, 1H), 6.35 (d, J=9 Hz, 1H), 4.20 (t, J=6 Hz, 2H), 4.08 (t, J=6 Hz, 2H), 3.85 (s, 3H), 2.50 (m, 4H), 2.24 (quintet, J=5 Hz, 2H), 1.45 (hextet, J=8 Hz, 2H), 1.09 (t, J=7 Hz, 3H), 0.82 (t, J=7 Hz, 3H); MS ES$^+$ m/e 531 (p+1); IR (KBr, cm$^{-1}$) 2961, 1697, 1602, 1460, 1222. Anal. Calcd for C$_{31}$H$_{34}$N$_2$O$_6$: C, 70.17; H, 6.46; N, 5.28. Found: C, 69.27; H, 6.08; N, 4.63.

Example 11

Preparation of 2-{3-[3-(2-Ethyl-5-hydroxy-4-thiazol-2-yl-phenoxy)propoxy]-2-propyl-phenoxy}benzoic acid.

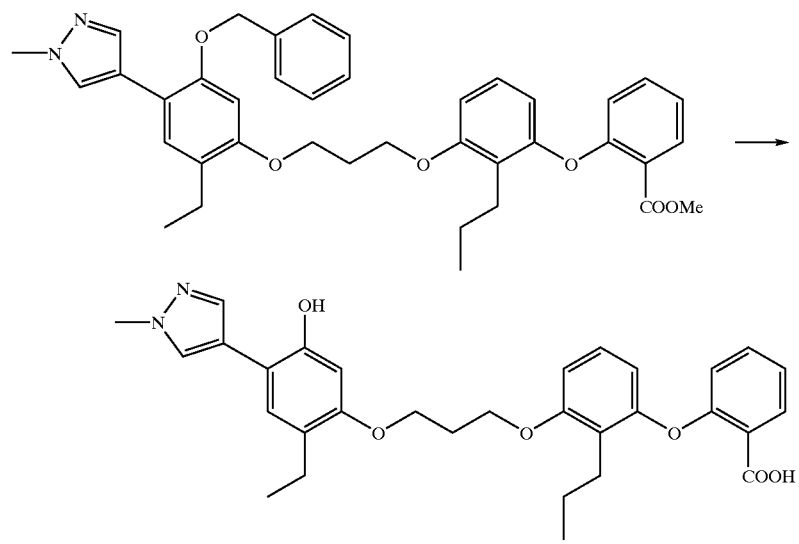

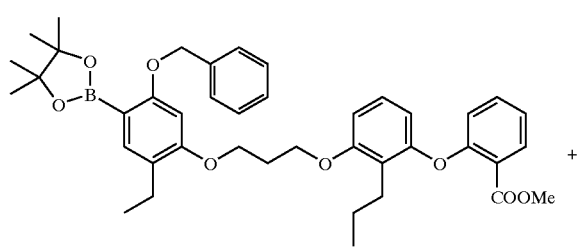

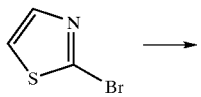

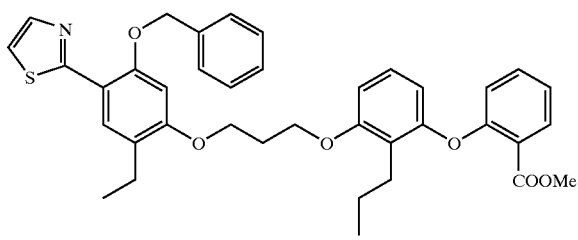

A. Preparation of 2-{3-[3-(5-benzyloxy-2-ethyl-4-thiazol-2-yl-phenoxy)propoxy]-2-propylphenoxy}benzoic acid methyl ester.

A mixture of 2-(3-{3-[5-benzyloxy-2-ethyl-4-(4,4,5,5-tetramethyl-[1,3,2]dioxaborolan-2-yl)phenoxy]propoxy}-2-propylphenoxy)benzoic acid methyl ester (960 mg, 1.41 mmol), 2-bromothiazole (0.25 mL, 2.8 mmol), cesium carbonate (1.15 g, 3.52 mmol), and PdCl$_2$(dppf) (35 mg, 0.040 mmol) in de-oxygenated toluene (35 mL) was heated at 60° C. for 16 h then at 100° C. for 7 h. Additional portions of 2-bromothiazole (0.13 mL) and PdCl$_2$(dppf) (~30 mg) were added and heating continued at 100° C. for 72 h. The mixture was cooled to room temperature, concentrated in vacuo, diluted with methylene chloride, and filtered down a short plug of silica gel. The filtrate was concentrated in vacuo. Chromatography (silica gel, hexane to 35% ethyl acetate/65% hexane) of the residue provided 282 mg (31%) of the title compound. $^1$H NMR (CDCl$_3$) δ 8.20 (s, 1H), 7.86 (dd, J=8, 1 Hz, 1H), 7.82 (d, J=3 Hz, 1H), 7.49 (d, J=7 Hz, 2H), 7.35 (m, 4H), 7.23 (d, J=3 Hz, 1H), 7.09 (d, J=9 Hz, 1H), 7.04 (d, J=9 Hz, 1H), 6.7B (d, J=9 Hz, 1H), 6.65 (d, J=9 Hz, 1H), 6.57 (s, 1H), 6.42 (d, J=8 Hz, 1H), 5.24 (s, 2H), 4.17 (m, 4H), 3.81 (s, 3H), 2.63 (m, 4H), 2.33 (quintet, J=6 Hz, 2H), 1.55 (hextet, J=8 Hz, 2H), 1.19 (t, J=7 Hz, 3H), 0.88 (t, J=7 Hz, 3H).

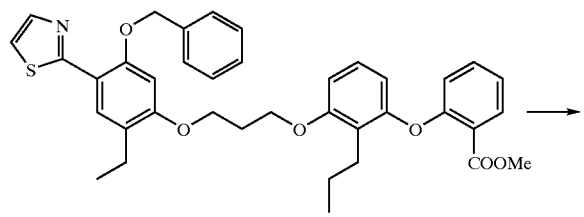

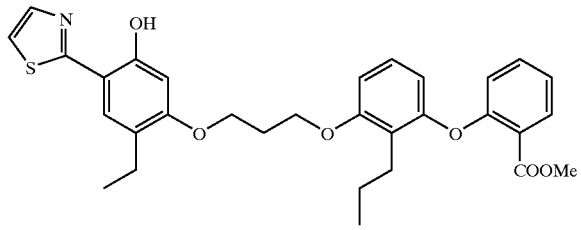

B. Preparation of 2-{3-[3-(2-ethyl-5-hydroxy-4-thiazol-2-yl-phenoxy)propoxy]-2-propylphenoxy}benzoic acid methyl eater.

A solution of 2-{3-[3-(5-benzyloxy-2-ethyl-4-thiazol-2-yl-phenoxy)propoxy]-2-propylphenoxy}benzoic acid methyl ester (282 mg, 0.442 mmol) in ethanethiol (3 mL) was treated with boron trifluoride etherate (0.56 mL, 4.4 mmol) at room temperature for 3 h. The reaction mixture was diluted with water, concentrated in vacuo, and extracted with diethyl ether. The organic layer was dried (magnesium sulfate), filtered, and concentrated in vacuo. Chromatography (silica gel, ethyl acetate/hexane) provided 107 mg (44%) of the title compound. $^1$H NMR (CDCl$_3$) δ 7.88 (dd, J=8, 2 Hz, 1H), 7.80 (d, J=4 Hz, 1H), 7.35 (dt, J=8, 2 Hz, 1H), 7.28 (d, J=4 Hz, 1H), 7.24 (s, 1H), 7.09 (dt, J=9, 2 Hz, 1H), 7.05 (t, J=9 Hz, 1H), 6.79 (d, J=9 Hz, 1H), 6.66 (d, J=9 Hz, 1H), 6.61 (s, 1H), 6.42 (d, J=9 Hz, 1H), 4.24 (t, J=6 Hz, 2H), 4.18 (t, J=6 Hz, 2H), 3.81 (s, 3H), 2.63 (t, J=7 Hz, 2H), 2.58 (q, J=7 Hz, 2H), 2.34 (quintet, J=6 Hz, 2H), 1.52 (hextet, J=8 Hz, 2H), 1.17 (t, J=7 Hz, 3H), 0.88 (t, J=7 Hz, 3H); MS ES$^+$ m/e 548 (p+1).

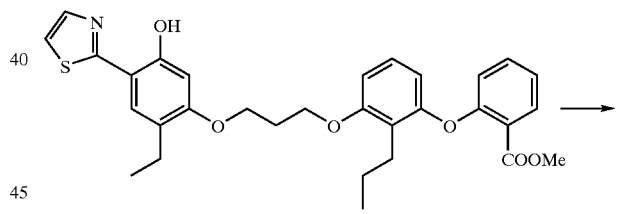

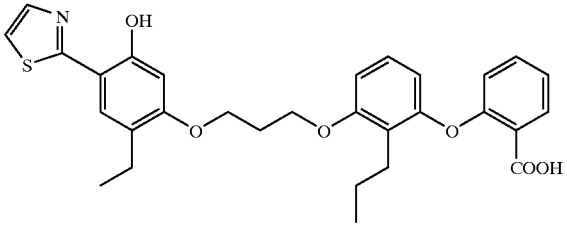

C. Preparation of 2-{3-[3-(2-ethyl-5-hydroxy-4-thiazol-2-yl-phenoxy)propoxy]-2-propylphenoxy}benzoic acid.

2-{3-[3-(2-Ethyl-5-hydroxy-4-thiazol-2-yl-phenoxy)propoxyl-2-propylphenoxy}benzoic acid methyl ester (107 mg, 0.196 mmol) was dissolved in a 1:1 solution of methanol/dioxane (3 mL) and treated with 1 N lithium hydroxide solution (1 mL) at 60° C. for 2 h. The mixture was concentrated in vacuo and the residue diluted with water, washed twice with diethyl ether, and the aqueous layer acidified with 1 N hydrochloric acid. The resulting solution was extracted twice with methylene chloride and the combined organic layers dried (magnesium sulfate), filtered, and concentrated in vacuo. Trituration (hexane) of the residue provided 72 mg (69%) of the title compound as a tan powder. $^1$H NMR (CDCl$_3$) δ 8.22 (dd, J=8, 2 Hz, 1H), 7.70 (d, J=4 Hz, 1H), 7.41 (dt, J=8, 2 Hz, 1H), 7.35 (s, 1H), 7.18 (m, 3H), 6.82 (d, J=9 Hz, 1H), 6.69 (d, J=9 Hz, 1H), 6.62 (d, J=9 Hz, 1H), 6.55 (s, 1H), 4.22 (t, J=6 Hz, 2H), 4.21 (t, J=6 Hz, 2H), 2.57 (m, 4H), 2.35 (quintet, J=6 Hz, 2H), 1.49 (hextet, J=8 Hz, 2H), 1.18 (t, J=7 Hz, 3H}, 0.86 (t, J=7 Hz, 3H); MS ES$^+$ m/e 534 (p+1); IR (KBr, cm$^{-1}$) 2957, 1695, 1599, 1457. Anal. Calcd for C$_{30}$H$_{31}$NO$_6$S: C, 67.52; H, 5.B6; N, 2.62. Found: C, 67.44; H, 5.95; N, 2.55.

Example 12
Preparation of 2-(3-{3-[4-(3,5-Dimethylisoxazol-4-yl)-2-ethyl-5-hydroxyphenoxy]propoxy}-2-propylphenoxy)benzoic acid sodium salt.

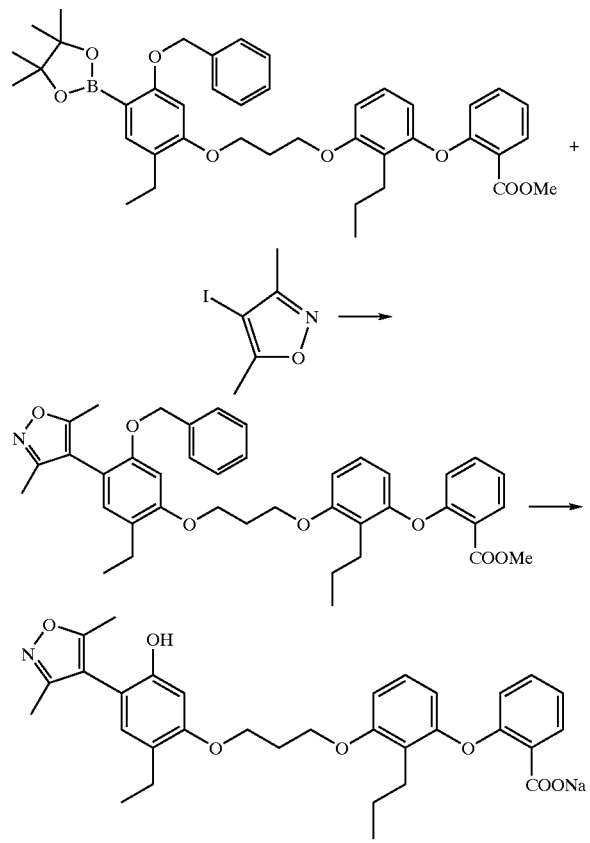

A mixture of 2-(3-{3-[5-benzyloxy-2-ethyl-4-(4,4,5,5-tetramethyl-[1,3,2]dioxaborolan-2-yl)phenoxy]propoxy}-2-propylphenoxy)benzoic acid methyl ester (305 mg, 0.448 mmol), 3,5-dimethyl-4-iodoisoxazole (110 mg, 0.493 mmol), cesium carbonate (293 mg, 0.899 mmol), and PdCl$_2$(dppf) (15 mg, 0.018 mmol) in de-oxygenated toluene (10 mL) was heated at 95° C. for 10 h. Additional portions of 3,5-dimethyl-4-iodoisoxazole (110 mg), cesium carbonate (260 mg), and PdCl$_2$(dppf) (~15 mg) were added and heating continued at 110° C. for 20 h. The mixture was cooled to room temperature, concentrated in vacuo, diluted with methylene chloride, and filtered down a short plug of silica gel with 20% ethyl acetate/80% hexane. The filtrate was concentrated in vacuo. The resulting colorless oil was dissolved in methylene chloride (4 mL), cooled to 0° C., and treated with iodotrimethylsilane (0.40 mL, 2.7 mmol). The resulting mixture was allowed to warm to room temperature and stirred for 18 h. An additional portion of iodotrimethylsilane (0.70 mL) was added and stirring continued for 72 h. The mixture was poured into dilute sodium thiosulfate solution. The organic layer was separated, washed with water, dried (sodium sulfate), filtered, and concentrated in vacuo. The resulting foam was dissolved in a 1:1 mixture of tetrahydrofuran/1 N hydrochloric acid (5 mL) and stirred at room temperature for 18 h. The mixture was concentrated in vacuo and treated with 1 equivalent 1 N sodium hydroxide solution in ether. The resulting mixture was concentrated in vacuo to provide 59 mg (23%) of the title compound as an off-white solid. $^1$H NMR (DMSO-d$_6$) δ 7.40 (dd, J=9, 2 Hz, 1H), 7.13 (dt, J=8, 2 Hz, 1H), 6.97 (m, 2H), 6.79 (s, 1H), 6.68 (d, J=9 Hz, 1H), 6.65 (d, J=9 Hz, 1H), 6.60 (s, 1H), 6.21 (d, J=8 Hz, 1H), 4.19 (t, J=6 Hz, 2H), 4.01 (t, J=6 Hz, 2H), 2.66 (t, J=8 Hz, 2H), 2.48 (q, J=8 Hz, 2H), 2.24 (s, 3H), 2.17 (quintet, J=6 Hz, 2H), 2.07 (s, 3 H), 1.49 (hextet, J=8 Hz, 2H), 1.07 (t, J=7 Hz, 3H), 0.85 (t, J=7 Hz, 3H); TOF MS ES$^+$ exact mass calculated for C$_{32}$H$_{36}$NO$_7$ (p+1): m/z=546.2492. Found: 546.2514; IR (KBr, cm$^{-1}$) 3400, 1605, 1460.

Example 13
Preparation of 2-{3-[3-(2-Ethyl-4-furan-2-yl-5-hydroxyphenoxy)propoxy]-2-propylphenoxy}-benzoic acid sodium salt.

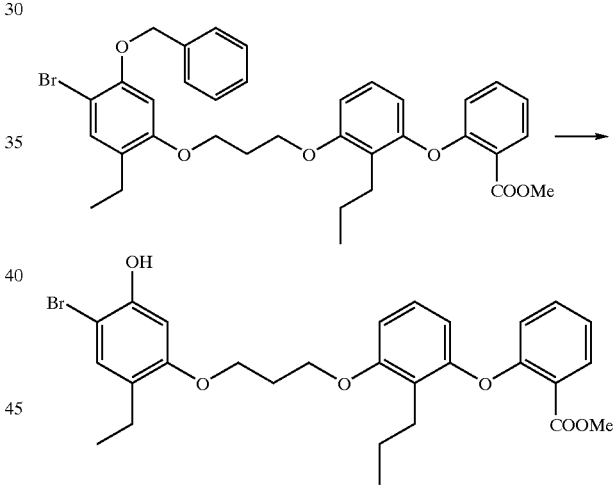

A. Preparation of 2-{3-[3-(4-bromo-2-ethyl-5-hydroxyphenoxy)propoxy]-2-propylphenoxy}benzoic acid= ethyl ester.

A solution of 2-{3-[3-(5-benzyloxy-4-bromo-2-ethylphenoxy)propoxy]-2-propylphenoxy}-benzoic acid methyl ester (2.50 g, 3.95 mmol) in methylene chloride (40 mL) was cooled to −70° C. and treated with boron tribromide (0.25 mL, 2.6 mmol). After 25 min the mixture was poured into cold water and the resulting mixture extracted with methylene chloride. The combined organic extracts were washed once with water, once with saturated sodium chloride solution, dried (sodium sulfate), filtered, and concentrated in vacuo to provide 1.1 g (52%) of the title compound as a pale yellow oil. 1$^1$H NMR (CDCl3) δ 7.89 (d, J=9 Hz, 1H), 7.38 (t, J=8 Hz, 1H), 7.18 (s 1H), 7.12 (d, J=9 Hz, 1H), 7.08 (d, J=2 Hz, 1H) , 6.81 (d, J=9 Hz, 1H) , 6.68 (d, J=9 Hz, 1H), 6.56 (s, 1H), 6.46 (d, J=9 Hz, 1H), 5.40 (s, 1H), 4.18 (t, J=6 Hz, 2H), 4.11 (t, J=6 Hz, 2H), 3.84 (s, 3H), 2.65 (t, J=8 Hz, 2H), 2.54 (q, J=7 Hz, 2H), 2.32 (quintet, J=6 Hz, 2H), 1.54 (hextet, J=8 Hz, 2H), 1.13 (t, J=7 Hz, 3H), 0.89 (t, J=7 Hz, 3H); MS ES⁻ m/z=541 (M–H), 543 (M–H+2).

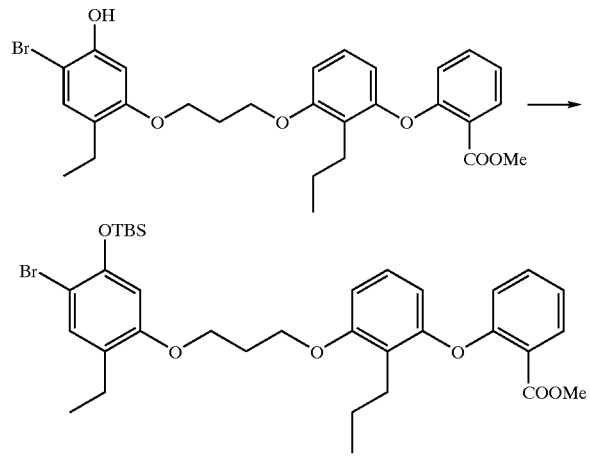

B. Preparation of 2-(3-{3-[4-bromo-5-(tert-butyldimethylsilanyloxy)-2-ethylphenoxy]-propoxy}-2-propylphenoxy)benzoic acid methyl eater.

A solution of 2-{3-[3-(4-bromo-2-ethyl-5-hydroxyphenoxy) propoxy]-2-propylphenoxy}benzoic acid methyl ester (1.00 g, 1.84 mmol) in methylene chloride (20 mL) was treated with imidazole (0.19 g, 2.8 mmol) and tert-butyldimethylsilyl chloride (0.388 g, 2.57 mmol) at room temperature for 2 h. The mixture was poured into water and the organic layer separated, washed once with water, once with saturated sodium chloride solution, filtered through a short pad of silica gel, and concentrated in vacuo to provide 1.1 g (91%) of the title compound as a colorless oil. ¹H NMR (CDCl₃) δ 7.88 (d, J=9 Hz, 1H), 7.38 (t, J=8 Hz, 1H), 7.22 (s 1H), 7.12 (d, J=9 Hz, 1H), 7.08 (d, J=2 Hz, 1H), 6.80 (d, J=9 Hz, 1H), 6.69 (d, J=9 Hz, 1H), 6.45 (d, J=9 Hz, 1H), 6.40 (s, 1H), 4.20 (t, J=6 Hz, 2H), 4.11 (t, J=6 Hz, 2H), 3.83 (s, 3H), 2.64 (t, J=8 Hz, 2H), 2.54 (q, J=7 Hz, 2H), 2.32 (quintet, J=6 Hz, 2H), 1.54 (hextet, J=8 Hz, 2H), 1.13 (t, J=7 Hz, 3H), 1.03 (s, 9H), 0.89 (t, J=7 Hz, 3H), 0.23 (s, 6H).

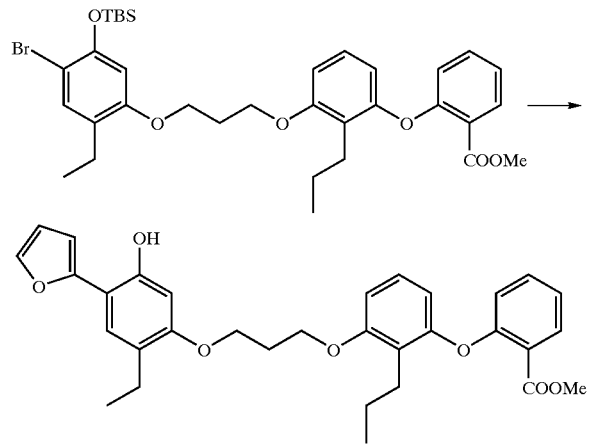

C. Preparation of 2-{3-[3-(2-ethyl-4-furan-2-yl-5-hydroxyphenoxy)propoxy]-2-propyl-phenoxy}benzoic acid methyl ester.

A mixture of 2-(3-{3-[4-bromo-5-(tert-butyldimethylsilanyloxy)-2-ethylphenoxy]propoxy}-2-propylphenoxy)benzoic acid methyl ester (1.05 g, 1.60 mmol), furan-2-boronic acid (0.358 g, 3.20 mmol), tetrakis (triphenylphosphine)palladium(0) (0.185 g, 0.160 mmol), and 2 M aqueous sodium carbonate solution (8 mL) in tetrahydrofuran (20 mL) was heated at reflux for 18 h. The mixture was cooled to room temperature, diluted with water, and extracted with ethyl acetate. The organic layer was separated, washed once with water, once with saturated sodium chloride solution, dried (sodium sulfate), filtered, and concentrated in vacuo. Chromatography (silica gel, 10% ethyl acetate/90% hexane) of the residue provided 0.8 g (94%) of the title compound as a colorless oil. ¹H NMR (CDCl₃) δ 7.90 (d, J=9 Hz, 1H), 7.48 (s, 1H), 7.38 (t, J=8 Hz, 1H), 7.21 (s 1H), 7.13 (s, 1H), 7.10 (d, J=9 Hz, 1H), 7.07 (d, J=2 Hz, 1H), 6.81 (d, J=9 Hz, 1H), 6.69 (d, J=9 Hz, 1H), 6.52 (m, 3H), 6.44 (d, J=9 Hz, 1H), 4.20 (m, 4H), 3.83 (s, 3H), 2.67 (t, J=8 Hz, 2H), 2.59 (q, J=7 Hz, 2H), 2.32 (quintet, J=6 Hz, 2H), 1.55 (hextet, J=8 Hz, 2H), 1.18 (t, J=7 Hz, 3H), 0.91 (t, J=7 Hz, 3H); MS ES⁻ m/z=589 (p+AcO⁻). Anal. Calcd for C₃₂H₃₄O₇: C, 72.43; H, 6.46. Found: C, 72.21; H, 6.15.

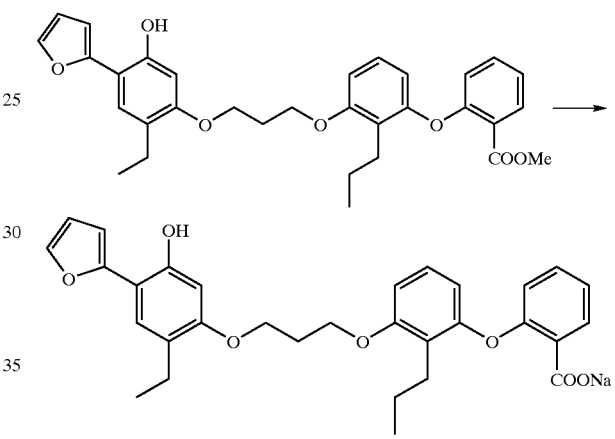

D. Preparation of 2-{3-[3-(2-ethyl-4-furan-2-yl-5-hydrophenoxy)propoxy]-2-]propylphenoxy}benzoic acid sodium salt.

2-{3-[3-(2-Ethyl-4-furan-2-yl-5-hydroxyphenoxy) propoxy]-2-propylphenoxy}benzoic acid methyl ester (250 mg, 0.47 mmol) was dissolved in tetrahydrofuran (4 mL) and treated with 1 N lithium hydroxide solution (2 mL) at 50° C. for 16 h. The mixture was concentrated in vacuo and the residue diluted with water and extracted twice with ethyl acetate. The combined organic extracts were washed once with water, once with saturated sodium chloride solution, dried (sodium sulfate), filtered, and concentrated in vacuo. The residue was dissolved in ethyl acetate and shaken with 1 N hydrochloric acid. The organic layer was dried (sodium sulfate), filtered, and concentrated in vacuo. The residue was dissolved in diethyl ether and treated with 1 N aqueous sodium hydroxide solution (0.32 mL). The mixture was concentrated in vacuo and azeotroped successively with diethyl ether, chloroform, and diethyl ether and dried to provide 168 mg (66%) of the title product as a cream solid. ¹H NMR (DMSO-d₆) δ 7.56 (s, 1H), 7.44 (d, J=8 Hz, 1H), 7.35 (s, 1H), 7.13 (m, 1H), 6.97 (m, 2H), 6.77 (d, J=2 Hz, 1H), 6.65 (m, 4H), 6.48 (d, J=2 Hz, 1H), 6.24 (d, J=9 Hz, 1H), 4.15 (t, J=6 Hz, 2H), 3.96 (t, J=6 Hz, 2H), 2.66 (t, J=8 Hz, 2H), 2.42 (q, J=7 Hz, 2H), 2.13 (quintet, J=6 Hz, 2H), 1.48 (hextet, J=8 Hz, 2H), 1.09 (t, J=7 Hz, 3H), 0.84 (t, J=7 Hz, 3H); TOF MS ES⁺ exact mass calculated for C₃₁H₃₃O₇ (p+1): m/z=517.2226. Found: 517.2230. IR (KBr, cm⁻¹) 3400, 2961, 1599, 1460.

Example 14

Preparation of 2-(3-{3-[2-Ethyl-5-hydroxy-4-furan-3-yl]phenoxy]propoxy}-2-propylphenoxy)benzoic acid.

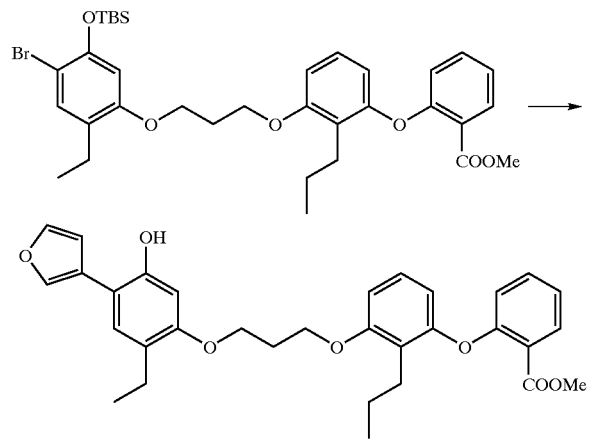

A. Preparation of 2-{3-[3-(2-ethyl-4-furan-3-yl-5-hydroxyphenoxy)propoxy]-2-propyl-phenoxy}benzoic acid methyl ester.

A mixture of 2-(3-{3-[4-bromo-5-(tert-butyldimethylsilanyloxy)-2-ethylphenoxy]propoxy}-2-propylphenoxy)benzoic acid methyl ester (2.10 g, 3.19 mmol), furan-3-boronic acid (0.722 g, 6.45 mmol), tetrakis(triphenylphosphine)palladium(0) (0.37 g, 0.32 mmol), and 2 M aqueous sodium carbonate solution (16 mL) in tetrahydrofuran (30 mL) was heated at reflux for 48 h. The mixture was cooled to room temperature, diluted with water, and extracted with ethyl acetate. The organic layer was separated, washed once with water, once with saturated sodium chloride solution, dried (sodium sulfate), filtered, and concentrated in vacuo. Chromatography (silica gel, 15% ethyl acetate/85% hexane) of the residue provided 0.29 g (17%) of the title compound as a yellow oil. TOF MS ES+ exact mass calculated for $C_{32}H_{35}O_7$ (p+1): m/z=531.2383. Found: 531.2396.

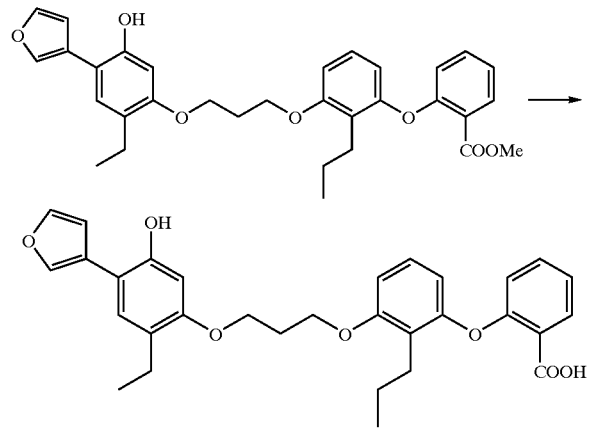

B. Preparation of 2-{3-[3-(2-ethyl-4-furan-3-yl-5-hydroxyphenoxy)propoxy]-2-propylphenoxy}benzoic acid sodium salt.

2-{3-[3-(2-Ethyl-4-furan-3-yl-5-hydroxyphenoxy)propoxy]-2-propylphenoxy}benzoic acid methyl ester (170 mg, 0.32 mmol) was dissolved in tetrahydrofuran (4 mL) and methanol (1 mL) and treated with 1 N lithium hydroxide solution (4 mL) at 50° C. for 2 h. The mixture was concentrated in vacuo and the residue acidified with hydrochloric acid and the resulting mixture extracted twice with ethyl acetate. The combined organic extracts were washed once with water, once with saturated sodium chloride solution, dried (sodium sulfate), filtered, and concentrated in vacuo. Chromatography (silica gel, 2% methanol/98% chloroform) of the residue gave 45 mg of material that was again submitted to chromatography (silica gel, 1% methanol/99% chloroform) to provide 25 mg (15%) of the title compound as an oil. TOF MS ES+ exact mass calculated for $C_{31}H_{33}O_7$ (p+1): m/z=517.226. Found: 517.2230.

Example 15

Preparation of 2-(3-{3-[2-Ethyl-5-hydroxy-4-(tetrahydrofuran-3-yl)phenoxy]propoxy}-2-propylphenoxy)benzoic acid sodium salt hemihydrate.

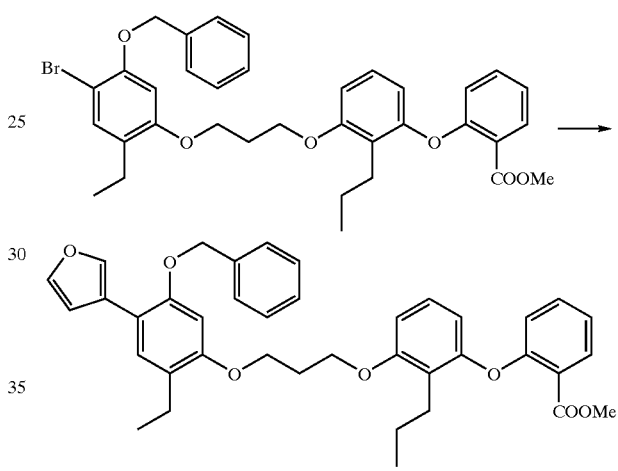

A. Preparation of 2-{3-[3-(5-benzyloxy-2-ethyl-4-furan-3-yl-phenoxy)propoxy]-2-propylphenoxy}benzoic acid methyl ester.

A mixture of 2-{3-[3-(5-benzyloxy-4-bromo-2-ethylphenoxy)propoxy]-2-propylphenoxy}-benzoic acid methyl ester (3.00 g, 4.73 mmol), furan-3-boronic acid (1.06 g, 9.47 mmol), tetrakis(triphenylphosphine)palladium(0) (0.54 g, 0.47 mmol), and 2 M aqueous sodium carbonate solution (20 mL) in tetrahydrofuran (40 mL) was heated at 100° C. for 48 h. The mixture was cooled to room temperature, diluted with water, and extracted with ethyl acetate. The organic layer was separated, washed once with water, once with saturated sodium chloride solution, dried (sodium sulfate), filtered, and concentrated in vacuo. Chromatography (silica gel, 10% ethyl acetate/90% hexane) of the residue provided 1.9 g (65%) of the title compound as a yellow oil. $^1$H NMR (CDCl$_3$) δ 7.88 (dd, J=8, 2 Hz, 1H), 7.87 (s, 1H), 7.40 (m, 7H), 7.26 (s 1H), 7.05 (m, 2H), 6.80 (d, J=9 Hz, 1H), 6.76 (d, J=2 Hz, 1H), 6.67 (d, J=9 Hz, 1H), 6.60 (s, 1H), 6.43 (d, J=9 Hz, 1H), 5.11 (s, 2H), 4.18 (m, 4H), 3.83 (s, 3H), 2.66 (t, J=8 Hz, 2H), 2.62 (q, J=7 Hz, 2H), 2.30 (quintet, J=6 Hz, 2H), 1.57 (hextet, J=8 Hz, 2H), 1.20 (t, J=7 Hz, 3H), 0.92 (t, J=7 Hz, 3H); MS ES+ m/z=621 (p+1); IR (CHCl$_3$, cm$^{-1}$) 3000, 1727, 1603, 1461.

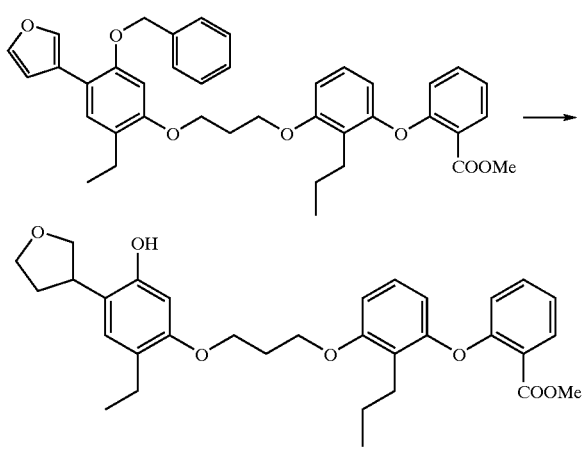

B. Preparation of 2-(3-{3-[2-ethyl-5-hydroxy-4-(tetrahydrofuran-3-yl)phenoxy]-propoxy}-2-propylphenoxy)benzoic acid methyl aster.

A solution of 2-{3-[3-(5-benzyloxy-2-ethyl-4-furan-3-yl-phenoxy)propoxy]-2-propylphenoxy}benzoic acid methyl ester (1.8 g, 2.9 mmol) in ethyl acetate (40 mL) was treated with 10% palladium-on-carbon (0.39 g) and hydrogenated at 48 psi and 45° C. for 72 h. The mixture was cooled to room temperature, filtered through Celite™, and the filtrate concentrated in vacuo to provide 1.2 g (77%) of the title compound as a colorless oil. $^1$H NMR (CDCl$_3$) δ 7.88 (dd, J=8, 2 Hz, 1H), 7.57 (dt, J=8, 2 Hz, 1H), 7.09 (d, J=9 Hz, 1H), 7.04 (d, J=9 Hz, 1H), 6.81 (d, J=9 Hz, 1H), 6.80 (s, 1H), 6.67 (d, J=9 Hz, 1H), 6.44 (d, J=9 Hz, 1H), 6.43 (s, 1H), 4.19 (m, 3H), 4.10 (m, 2H), 4.02 (dd, J=12, 3 Hz, 1H), 3.88 (dd, J 12, 8 Hz, 1H), 3.84 (s, 3H), 3.73 (q, J=9 Hz, 1H), 3.45 (m, 1H), 2.64 (t, J=8 Hz, 2H), 2.53 (q, J=7 Hz, 2H), 2.38 (m, 1H), 2.28 (quintet, J=6 Hz, 2H), 1.99 (m, 1H), 1.55 (hextet, J=8 Hz, 2H), 1.15 (t, J=7 Hz, 3H), 0.90 (t, J=7 Hz, 3H); MS ES$^-$ m/z=593 (p+CH$_3$COO$^-$); IR (CHCl$_3$, $^-$cm$^{-1}$) 2963, 1719, 1589, 1461. Anal. Calcd for C$_{32}$H$_{38}$O$_7$: C, 71.89; H, 7.16. Found: C, 71.41; H, 7.06.

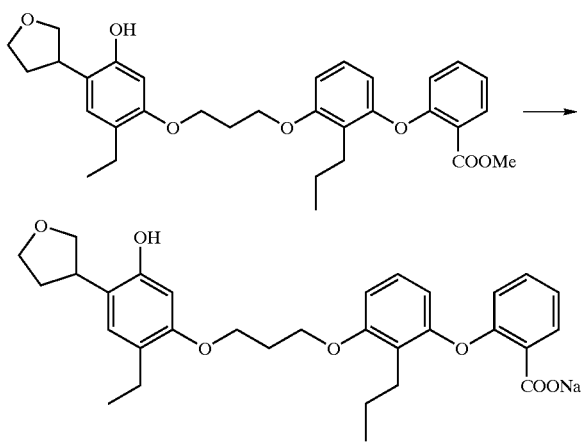

C. Preparation of 2-(3-{3-[2-ethyl-5-hydroxy-4-(tetrahydrofuran-3-yl)phenoxy]-propoxy}-2-propylphenoxy)benzoic acid sodium salt hemihydrate.

A solution of 2-(3-{3-[2-ethyl-5-hydroxy-4-(tetrahydrofuran-3-yl) phenoxy]propoxy}-2-propylphenoxy)benzoic acid methyl ester (0.92 g, 1.7 mmol) in tetrahydrofuran (10 mL) and methanol (5 mL) was treated with 1 M aqueous lithium hydroxide solution (10 mL) at 55° C. for 2 h. The mixture was allowed to cool to room temperature and stirred for an additional 18 h. The mixture was concentrated in vacuo and the remaining aqueous mixture was washed once with diethyl ether. The aqueous layer was acidified with concentrated hydrochloric acid and the resulting solution extracted with ethyl acetate. The ethyl acetate layer was washed once with water, once with saturated sodium chloride solution, dried (sodium sulfate), filtered, and concentrated in vacuo. The resulting colorless oil was dissolved in diethyl ether and treated with 1 N aqueous sodium hydroxide solution (1.72 mL). The resulting biphasic mixture was diluted with chloroform and concentrated in vacuo. Diethyl ether was added and the mixture concentrated in vacuo. The resulting white foam was dried in vacuo at room temperature for 60 h to provide 0.78 g (84%) of the title compound: mp 67–71° C. $^1$H NMR (DMSO-d$_6$) δ 7.62 (dd, J=8, 2 Hz, 1H), 7.30 (dt, J=8, 2 Hz, 1H), 7.05 (m, 2H), 6.85 (s, 1H), 6.73 (d, J=9 Hz, 1H), 6.70 (d, J=9 Hz, 1H), 6.53 (s, 1H), 6.34 (d, J=9 Hz, 1H), 4.15 (t, J=6 Hz, 2H), 4.04 (t, J=6 Hz, 2H), 3.95 (m, 1H), 3.88 (m, 1H), 3.75 (q, J=9 Hz, 1H), 3.49 (m 2H), 2.60 (t, J=8 Hz, 2H), 2.45 (q, J=7 Hz, 2H), 2.15 (m, 3H), 1.90 (m, 1H), 1.48 (hextet, J=8 Hz, 2H), 1.06 (t, J=7 Hz, 3H), 0.83 (t, J=7 Hz, 3H); MS ES$^+$ m/z=519 (p–Na$^+$); IR (CHCl$_3$, cm$^{-1}$) 2964, 1783, 1604, 1461. Anal. Calcd for C$_{31}$H$_{35}$NaO$_7$·0.5 H$_2$O: C, 67.50; H, 6.58. Found: C, 67.76; H, 6.68.

Example 16

Preparation of 2-{3-[3-(2-Ethyl-5-hydroxy-4-pyrrolidin-2-yl-phenoxy)propoxy]-2-propyl-phenoxy}benzoic acid hydrochloride hydrate.

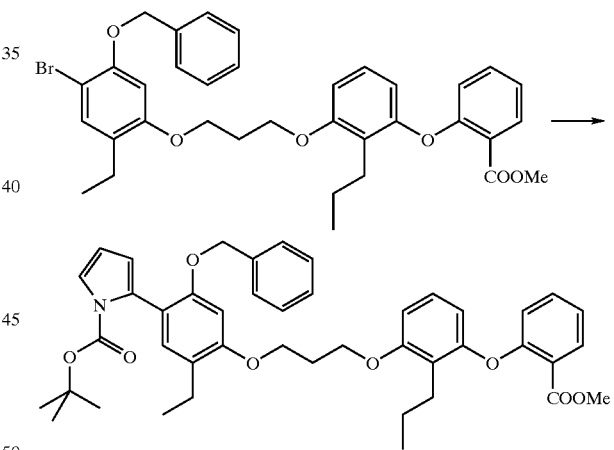

A. Preparation of 2-(2-benzyloxy-5-ethyl-4-{3-[3-(2-methoxycarbonylphenoxy)-2-propylphenoxy] propoxy}phenyl)pyrrole-1-carboxylic acid tert-butyl ester.

A mixture of 2-{3-[3-(5-benzyloxy-4-bromo-2-ethylphenoxy)propoxy]-2-propylphenoxy}-benzoic acid methyl ester (3.00 g, 4.73 mmol), N-boc pyrrole-2-boronic acid (1.99 g, 9.43 mmol), tetrakis(triphenylphosphine)palladium(0) (0.54 g, 0.47 mmol), and 2 M aqueous sodium carbonate solution (25 mL) in tetrahydrofuran (60 mL) was heated at reflux for 40 h. The mixture was cooled to room temperature, diluted with water, and extracted with ethyl acetate. The organic layer was separated, washed once with water, once with saturated sodium chloride solution, dried (sodium sulfate), filtered, and concentrated in vacuo. Chromatography (silica gel, 10% ethyl acetate/90% hexane) of the residue provided 2.6 g (76%) of the title compound as a solid. $^1$H NMR (CDCl$_3$) δ 7.88 (dd, J=8, 2 Hz, 1H), 7.15–7.40 (m, 7H), 7.08 (m, 3H), 6.82 (d, J=9 Hz, 1H), 6.68 (d, J=9 Hz, 1H), 6.52 (s, 1H), 6.44 (d, J=9 Hz, 1H), 6.23 (t, J=4 Hz, 1H), 6.12 (m, 1H), 4.95 (s, 2H), 4.20 (t, J=6 Hz, 2H); 4.15 (t, J=6 Hz, 2H), 3.84 (s, 3H), 2.66 (t, J=8 Hz, 2H), 2.60 (q, J=7 Hz, 2H), 2.30 (quintet, J=6 Hz, 2H), 1.57 (hextet, J=8 Hz, 2H), 1.28 (s, 9H), 1.18 (t, J=7 Hz, 3H), 0.93 (t, J=7 Hz, 3H); TOS MS ES$^+$ exact mass calculated for C$_{44}$H$_{53}$N$_2$O$_8$ (p+NH$^4$): m/z=737.3802. Found: 737.3804; IR (CHCl$_3$, cm$^{-1}$) 2964, 1730, 1461. Anal. Calcd for C$_{44}$H$_{49}$NO$_8$: C, 73.41; H, 6.86; N, 1.94. Found: C, 73.76; H, 6.76; N, 2.04.

propoxy}phenyl)pyrrole-1-carboxylic acid tert-butyl ester (0.98 g, 1.4 mmol) in ethyl acetate (40 mL) was treated with 10% palladium-on-carbon (0.98 g) and hydrogenated at 45 psi and 45° C. for 25 h, at room temperature for 20 h, then at 45° C. for 19 h. The mixture was cooled to room temperature, filtered through Celite™, and the filtrate concentrated in vacuo to provide 0.76 g (88%) of the title compound as a colorless oil. $^1$H NMR (CDCl$_3$) δ 7.87 (dd, J=8, 2 Hz, 1H), 7.37 (dt, J=8, 2 Hz, 1H), 7.10 (d, J=9 Hz, 1H), 7.04 (d, J=9 Hz, 1H), 6.91 (s, 1H), 6.81 (d, J=9 Hz, 1H),

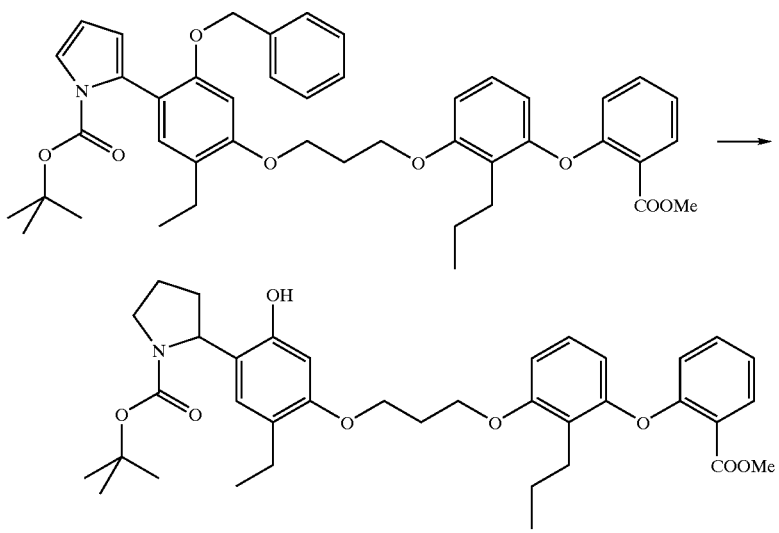

B. Preparation of 2-(5-ethyl-2-hydroxy-4-{3-[3-(2-methoxycarbonylphenoxy)-2-propylphenoxy]propoxy}phenyl)-pyrrolidine-1-carboxylic acid tert-butyl eater.
A solution of 2-(2-benzyloxy-5-ethyl-4-{3-[3-(2-methoxycarbonylphenoxy)-2-propylphenoxy]

6.67 (d, J=9 Hz, 1H), 6.47 (s, 1H), 6.44 (d, J=9 Hz, 1H), 5.09 (m, 1H), 4.18 (d, J=6 Hz, 2H), 4.14 (t, J=6 Hz, 2H), 3.84 (s, 3H), 3.45 (m, 2H), 2.64 (t, J=8 Hz, 2H), 2.54 (m, 3H), 2.25 (m, 5H), 2.06 (m, 1H), 1.54 (hextet, J=8 Hz, 2H), 1.43 (s, 9H), 1.15 (t, J=7 Hz, 3H), 0.90 (t, J=7 Hz, 3H).

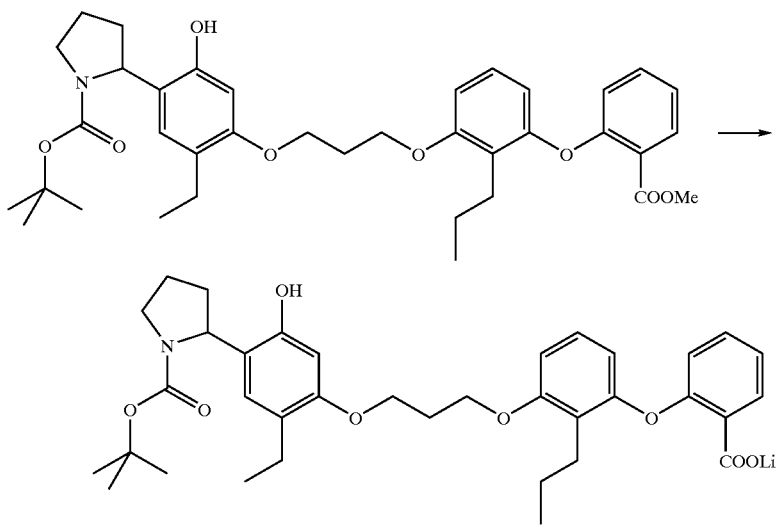

C. Preparation of 2-(4-{3-[3-(2-carboxyphenoxy)-2-propylphenoxy]propoxy}-5-ethyl-2-hydroxyphenyl)pyrrolidine-1-carboxylic acid tert-butyl eater lithium salt hydrate.

A solution of 2-(5-ethyl-2-hydroxy-4-{3-[3-(2-methoxycarbonylphenoxy)-2-propylphenoxy]propoxy) phenyl}pyrrolidine-1-carboxylic acid tert-butyl ester (0.114 g, 0.18 mmol) in a 1:1 mixture of methanol/tetrahydrofuran (4 mL) was treated with solution of 1 M lithium hydroxide (4 mL) at room temperature for 18 h. The mixture was concentrated in vacuo and the residue dissolved in water. The resulting mixture was extracted with ethyl acetate. The organic extract was dried (sodium sulfate), filtered, and concentrated in vacuo. The residue was diluted with diethyl ether, concentrated in vacuo, and dried to provide 90 mg (78%) of the title compound. MS ES+ m/z=620 (p+1−Li+); IR (KBr, cm$^{-1}$) 2964, 1672, 1603, 1416. Anal. Calcd for $C_{36}H_{44}NO_8Li\cdot H_2O$: C, 67.17; H, 7.20; N, 2.18. Found: C, 66.72; H, 6.99; N, 2.27.

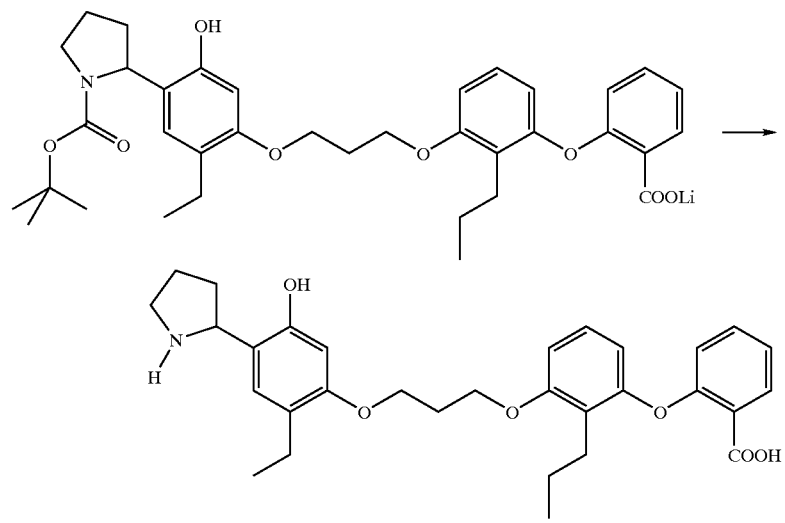

D. Preparation of 2-{3-[3-(2-ethyl-5-hydroxy-4-pyrrolidin-2-yl-phenoxy)propoxy]-2-propylphenoxy}benzoic acid hydrochloride hydrate.

Into a solution of 2-(4-{3-[3-(2-carboxyphenoxy)-2-propylphenoxy]propoxy}-5-ethyl-2-hydroxyphenyl)pyrrolidine-1-carboxylic acid tert-butyl ester lithium salt hydrate (0.100 g, 0.16 mmol) in anhydrous diethyl ether (5 mL) was bubbled gaseous HCl. The resulting mixture was allowed to stir for 1 h. The mixture was concentrated in vacuo. Chromatography (SCX cation exchange resin, 1:1 tetrahydrofuran/methanol to dilute ammonia/methanol) of the residue provided a tan solid. This material was dissolved in ether and treated with gaseous HCl. This mixture was concentrated in vacuo to provide 48 mg (52%) of the title compound. $^1$H NMR (DMSO-$d_6$) δ 12.80 (bs, 1H), 10.12 (s, 1H), 9.34 (bs, 1H), 8.36 (bs, 1H), 7.79 (dd, J=9, 2 Hz, 1H), 7.47 (dt, J=8, 2 Hz, 1H), 7.17 (t, J=8 Hz, 1H), 7.12 (d, J=9 Hz, 1H), 7.07 (s, 1H), 6.80 (d, J=9 Hz, 1H), 6.78 (d, J=9 Hz, 1H), 6.58 (s, 1H), 6.35 (d, J=9 Hz, 1H), 4.56 (m, 1H), 4.20 (t, J=6 Hz, 2H); 4.11 (t, J=6 Hz, 2H), 3.25 (m, 2H), 2.50 (m, 5H), 1.90–2.60 (m, 5H), 1.44 (hextet, J=8 Hz, 2H), 1.08 (t, J=7 Hz, 3H), 0.82 (t, J=7 Hz, 3H); TOS MS ES+ exact mass calculated for $C_{31}H_{38}NO_6$ (p+1): m/z=520.2699. Found: 520.2672.

Example 17

Preparation of 2-{3-[3-(2-Ethyl-5-hydroxy-4-thiophen-3-yl-phenoxy)propoxy]-2-propyl-phenoxy}benzoic acid hydrate.

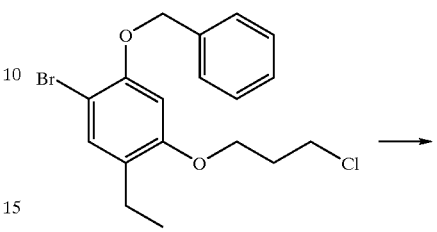

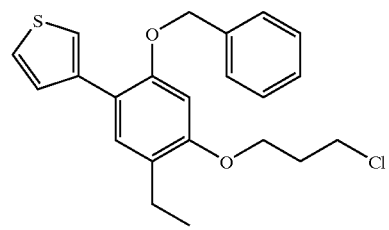

Known compound:
Sawyer et al., J. Med. Chem. 1995, 38, 4411.

A. Preparation of 3-[2-benzyloxy-4-(3-chloropropoxy)-5-ethylphenyl]thiophene. A mixture of 4-(benzyloxy)-5-bromo-2-(3-chloropropoxy)ethylbenzene (1.90 g, 5.30 mmol), 3-thiopheneboronic acid (2.00 g, 15.9 mmol), tetrakis(triphenylphosphine)palladium(0) (312 mg, 0.270 mmol), 2 M aqueous sodium carbonate solution (4 mL), and n-propanol (4 mL) in toluene (16 mL) was refluxed for 4 h. The mixture was cooled to room temperature, diluted with diethyl ether, washed once with water and once with satu rated sodium chloride solution. The organic layer was dried (magnesium sulfate), filtered, and concentrated in vacuo. Chromatography (silica gel, 5% ethyl acetate/95% hexane) of the residue provided 1.54 g (80%) of the title product as a white solid: mp 65–67° C. $^1$H NMR (CDCl$_3$) δ 7.58 (d, J=2.8 Hz, 1H), 7.49 (d, J=5.2 Hz, 1H), 7.45–7.30 (m, 7H), 6.62 (s, 1H), 5.13 (s, 2H), 4.14 (t, J=5.8 Hz, 2H), 3.81 (t, J=6.3 Hz, 2H), 2.66 (q, J=7.5 Hz, 2H), 2.29 (quintet, J=6.0 Hz, 2H), 1.24 (t, J=7.5 Hz, 3H); MS FD m/e 386 (p); IR (CHCl$_3$, cm$^{-1}$) 2969, 1613, 1501, 1138. Anal. Calcd for C$_{22}$H$_{23}$O$_2$ClS: C, 68.29; H, 5.99. Found: C, 68.53; H, 6.00.

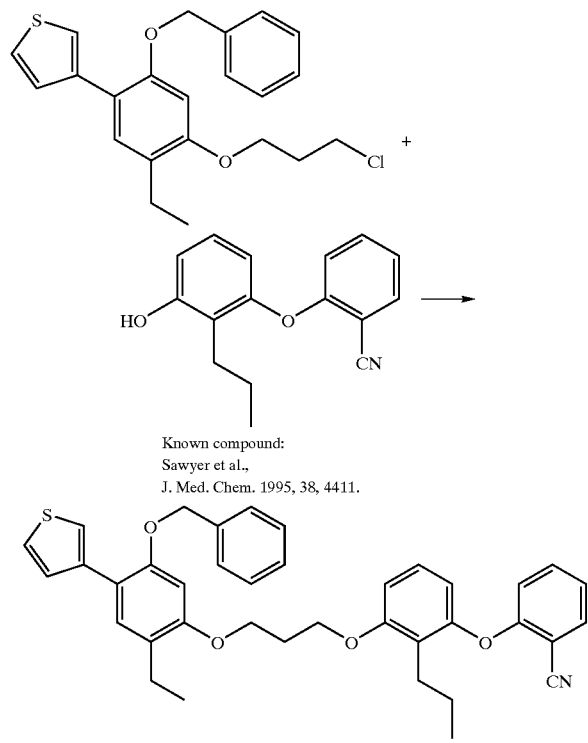

B. Preparation of 2-[2-propyl-3-[3-[5-(benzyloxy3)-2-ethyl-4-(thiophen-3-yl)phenoxy]propoxy]phenoxy]benzonitrile.

A mixture of 4-(benzyloxy)-2-(3-chloropropoxy)-5-(thiophen-3-yl)ethylbenzene (1.25 g, 3.23 mmol), 3-(2-cyanophenoxy)-2-propylphenol (0.82 g, 3.2 mmol), potassium iodide (0.21 g, 1.3 mmol), potassium carbonate (1.12 g, 8.08 mmol), and methyl sulfoxide (2 mL) in 2-butanone (10 mL) was refluxed for 60 h. The mixture was cooled to room temperature, diluted with ether, and washed with water. The organic layer was dried (magnesium sulfate), filtered, and concentrated in vacuo. Chromatography (silica gel, 5% ethyl acetate/95% hexane) of the residue provided 1.31 g (67%) of the title product as a colorless oil. $^1$H NMR (CDCl$_3$) δ 7.66 (d, J=7.8 Hz, 1H), 7.57 (d, J=2.9 Hz, 1H), 7.48 (d, J=5.2 Hz, 1H), 7.45–7.25 (m, 8H), 7.20 (t, J=8.2 Hz, 1H), 7.10 (t, J=8.1 Hz, 1H), 6.82 (d, J=8.3 Hz, 1H), 6.77 (d, J=8.6 Hz, 1H), 6.64 (s, 1H), 6.63 (d, J=6.4 Hz, 1H), 5.11 (s, 2H), 4.26 (t, J=6.0 Hz, 2H), 4.22 (t, J=6.0 Hz, 2H), 2.65 (m, 4H), 2.36 (quintet, J=5.9 Hz, 2H), 1.58 (hextet, J=7.5 Hz, 2H), 1.24 (t, J=7.5 Hz, 3H), 0.95 (t, J=7.3 Hz, 3H); MS FD m/e 603 (p); IR (CHCl$_3$, cm$^{-1}$) 2967, 2250, 1613, 1501. Anal. Calcd for C$_{38}$H$_{37}$NO$_4$S: C, 75.59; H, 6.18; N, 2.32. Found: C, 74.65; H, 6.21; N, 2.57.

C. Preparation of 2-[2-propyl-3-[3-[2-ethyl-5-hydroxy-4-(thiophen-3-yl)phenoxy]propoxy]phenoxy]benzonitrile.

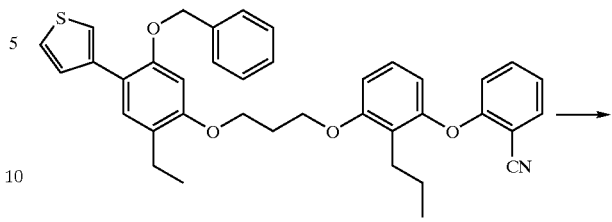

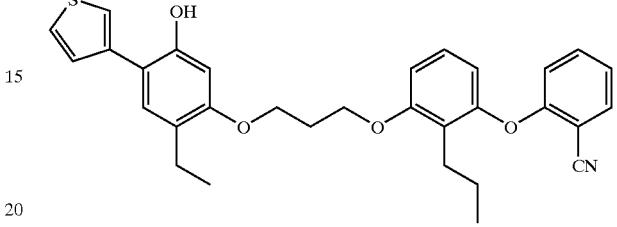

To a solution of 2-[2-propyl-3-[3-[5-(benzyloxy)-2-ethyl-4-(thiophen-3-yl)phenoxy]propoxy]phenoxy]benzonitrile (900 mg, 1.49 mmol) in methylene chloride (25 mL) cooled to −78° C. was added 1 M boron tribromide solution in methylene chloride (2.99 mL, 2.99 mmol) over 2 min. The resulting deep violet solution was stirred for 30 min and allowed to warm to room temperature. The mixture was diluted with water and shaken. The organic layer was separated, dried (magnesium sulfate), filtered, and concentrated in vacuo. Chromatography (silica gel, 25% ethyl acetate, 75% hexane) provided 400 mg (52%) of the title product as a colorless oil. $^1$H NMR (CDCl$_3$) δ 7.84 (d, J=4.8 Hz, 1H), 7.71 (d, J=4.9 Hz, 1H), 7.66 (d, J=7.7 Hz, 1H), 7.62 (s, 1i), 7.42 (t, J=7.1 Hz, 1H), 7.27 (t, J=6.6 Hz, 1H), 7.20 (s, 1H), 7.08 (t, J=6.9 Hz, 1H), 6.85 (s, 1H), 6.89 (d, J=8.1 Hz, 1H), 6.74 (d, J=8.5 Hz, 1H), 6.60 (d, J=7.6 Hz, 1H), 4.71 (s, 1H, —OH), 4.26 (t, J=6.0 Hz, 4H), 2.72 (q, J=7.4 dHz, 2H), 2.59 (t, J=7.3 Hz, 2H), 2.39 (quintet, J=6.1 Hz, 2H), 1.54 (hextet, J=7.7 Hz, 2H), 1.25 (t, J=7.5 Hz, 3H), 0.91 (t, J=7.4 Hz, 3H).

D. Preparation of 2-[2-propyl-3-[3-[2-ethyl-5-hydroxy-4-(thiophen-3-yl)phenoxy]propoxy]phenoxy]benzoic acid hydrate.

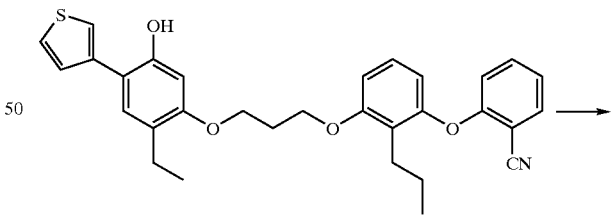

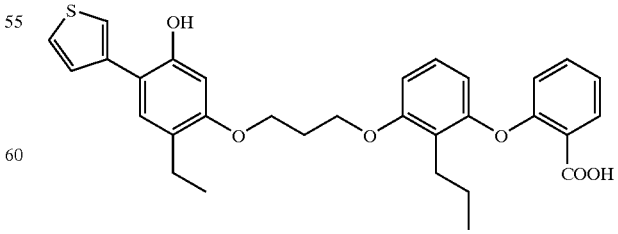

A solution of 2-[2-propyl-3-[3-[2-ethyl-5-hydroxy-4-(thiophen-3-yl)phenoxy]propoxy]phenoxy]benzonitrile (400 mg, 0.780 mmol) in 2:1 methanol/water (6 mL) was treated with 12.5 M aqueous sodium hydroxide (4.0 mL) at reflux for 36 h. The mixture was cooled to room temperature, diluted with water, and extracted once with diethyl ether. The aqueous layer was acidified with concentrated hydrochloric acid and extracted twice with methylene chloride. The combined methylene chloride layers were dried (magnesium sulfate), filtered, and concentrated in vacuo to provide a tan solid: mp 90–95° C. (dec). $^1$H NMR (CDCl$_3$) δ 8.24 (d, J=7.8 Hz, 1H), 7.47 (d, J=5.0 Hz, 1H), 7.44 (t, J=8.6 Hz, 1H), 7.36 (d, J=3 Hz, 1H), 7.24 (d, J=4.9 Hz, 1H), 7.19 (m, 2H), 7.09 (s, 1H), 6.84 (d, J=8.0 Hz, 1H), 6.73 (d, J=8.3 Hz, 1H), 6.64 (d, J=8.0 Hz, 1H), 6.55 (s, 1H), 5.38 (bs, 1H, —OH), 4.26 (t, J=6.2 Hz, 2H), 4.21 (t, J=7.1 Hz, 2H), 2.60 (m, 4H), 2.36 (quintet, J=5.8 Hz, 2H), 1.51 (hextet, J=7.1 Hz, 2H), 1.19 (t, J=7.5 Hz, 3H), 0.90 (t, J=7.4 Hz, 3H); MS FD m/e 532 (p); IR (KBr, cm$^{-1}$) 3200 (br), 2961, 1697, 1457, 1110. Anal. Calcd for C$_{31}$H$_{32}$O$_6$S.H$_2$O: C, 67.62; H, 6.22. Found: C, 67.34; H, 5.87.

VI. Pharmaceutical Compositions of the Invention

Preferably compounds of the invention (per Formulae I or II) or pharmaceutical formulations containing these compounds are in unit dosage form for administration to a mammal. The unit dosage form can be a capsule, an IV bag, a tablet, or a vial. The quantity of Active Ingredient in a unit dose of composition is a therapeutically effective amount and may be varied according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the compounds of the invention (e.g., compounds of Formula I, II) together with a pharmaceutically acceptable carrier or diluent therefor. The present pharmaceutical formulations are prepared by known procedures using well known and readily available ingredients.

In making the compositions of the present invention, the Active Ingredient will usually be admixed with a carrier, or diluted by a carrier, or enclosed within a carrier which may be in the form of a capsule, sachet, paper or other container. When the carrier serves as a diluent, it may be a solid, lyophilzed solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of about 0.05 to about 5.0 mg/ml in a 4% dextrose/ 0.5% Na citrate aqueous solution.

Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active Ingredient. In tablets the Active Ingredient is mixed with a carrier having the necessary binding properties in suitable proportions and compacted in the shape and size desired.

Advantageously, compositions containing the compound of Formula (I) may be provided in dosage unit form, preferably each dosage unit containing from about 5 to about 500 mg (from about 5 to 50 mg in the case of parenteral or inhalation administration, and from about 25 to 500 mg in the case of oral or rectal administration. Dosages from about 0.5 to about 300 mg/kg per day, preferably 0.5 to 20 mg/kg, of Active Ingredient may be administered although it will, of course, readily be understood that the amount of the compound or compounds of Formula I actually to be administered will be determined by a physician, in the light of all the relevant circumstances.

Powders and tablets preferably contain from about 1 to about 99 weight percent of the Active Ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active Ingredient can be dissolved or suspended in a pharmaceutically acceptable carrier, such as sterile water, sterile organic solvent or a mixture of both. By "pharmaceutically acceptable" it is meant the carrier, diluent or excipient must be compatible with the other ingredientsof the formulation and not deleterious to the recipient thereof.

The Active Ingredient can also be dissolved in a suitable organic solvent, for instance aqueous propylene glycol. Other compositions can be made by dispersing the finely divided Active Ingredient in aqueous starch or sodium carboxymethyl cellulose solution or in a suitable oil.

The following pharmaceutical formulations 1 to 8 are illustrative only and are not intended to limit the scope of the invention in any way. "Active Ingredient", refers to a compound according to Formula (I) or (II) or a pharmaceutically acceptable salt, solvate, or prodrug thereof.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
|---|---|
| Active Ingredient | 0.25 |
| Ethanol | 25.75 |
| Propellant 22 (Chlorodifluoromethane) | 74.00 |
| Total | 100.00 |

The Active Ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of Active Ingredient, are made as follows:

| Active Ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve (355 μm) and mixed thoroughly. The aqueous solution containing polyvinylpyrrolidone is mixed with the resultant powder, and the mixture then is passed through a No. 14 mesh U.S. sieve (1.4 mm). The granules so produced are dried at 50° C. and passed through a No. 18 mesh U.S. sieve (1.00 mm). The sodium carboxymethyl starch, magnesium stearate and talc, previously passed through a No. 60 mesh U.S. sieve (250 μm), are then added to the granules which, after mixing, are compressed on a tablet machine to yield tablets each weighing 150 mg.

Formulation 5

Capsules, each containing 80 mg of Active Ingredient, are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 U.S. sieve (355 μm), and filled into hard gelatin capsules in 200 mg quantities.

Formulation 6

Suppositories, each containing 225 mg of Active Ingredient, are made as follows:

| Active Ingredient | 225 mg |
|---|---|
| Saturated fatty acid glycerides | 2,000 mg |
| Total | 2,225 mg |

The Active Ingredient is passed through a No. 60 U.S. sieve (250 μm) and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active Ingredient per 5 ml dose, are made as follows:

| Active Ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active Ingredient is passed through a No. 45 mesh U.S. sieve (355 μm) and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active Ingredient | 100 mg |
|---|---|
| Isotonic saline | 1,000 ml |

The solution of the above materials generally is administered intravenously to a subject at a rate of 1 ml per minute.

All of the products of the Examples described below as well as intermediates used in the following procedures showed satisfactory nmr and ir spectra. They also had the correct mass spectral values.

VII. Method of Using the Compounds of the Invention

This invention is a method for preventing or treating $LTB_4$ induced inflammation in a mammal by contacting the $LTB_4$ in a mammal with an $LTB_4$ antagonizing amount of the heterocyclic substituted diphenyl compounds of the invention (as per formula I or II) or a salt, solvate or prodrug of said compounds.

Another aspect of this invention is a method for preventing or treating Inflammatory Diseases such as inflammatory bowel disease, septic shock, adult respiratory distress syndrome, panceatitis, trauma, bronchial asthma, allergic rhinitis, rheumatoid arthritis, osteoarthritis, and related diseases which comprises administering to a mammal (including a human) a therapeutically effective dose of heterocyclic substituted diphenyl compounds of the invention (as per formula I or II) or a salt, solvate or prodrug of said compounds.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of the compound of formulae (I). When route of administration is parenteral the dose is about 0.1 to about 100 milligrams per day. Intravenous administration can include a continuous drip. When the route is oral the dose is about 1 to about 1000 milligrams per day. Preferred dosages are from about 0.5 to about 300 mg/kg per day, most preferably 0.5 to 20 mg/kg, of Active Ingredient may be administered although it will, of course, readily be understood that the amount of the compound or compounds of Formula I actually to be administered will be determined by a physician, in the light of all the relevant circumstances.

VIII. Assay Method

The following Assay method was used to evaluate the effects of 3 compounds for $LTB_4$-mediated CD11b upregulation on human neutrophils:

Note: The Assay procedure described herein was modeled after a previously published method(viz., Prostaglandins, Leukot, Essent. Fatty Acids. 46:265–270. 1992, Biochem. Pharmacol. 49:1683–1690. 1995), the disclosure of which is incorporated herein by reference.

The compound C (within the scope of the invention) was evaluated for $LTB_4$ antagonist efficacy. Compounds A and B were control compounds. Compound A is a leukotriene $B_4$ antagonist known to be effective, but belonging to a different class of compounds than represented by formulae I or II, supra. Comparison compound B is structurally similar to the compounds of the invention, but lacks certain essential functional groups necessary for an effective $LTB_4$ antagonist.

Approximately 1–2 mg of each compound was weighed and diluted to 1 mM in neat dimethyl sulphoxide (DMSO). These stocks were then diluted (using "doubling" dilutions) in assay buffer.

The assay buffer used throughout the studies consisted of Hanks Balanced Salts Solution (HBSS) with added 0.5% bovine serum albumin, low endotoxin (ICN Biomedicals Catalog #16-980-49). After dissolving the BSA in the HBSS, the buffer was membrane-filtered (0.2 $\mu$) before use.

Human blood was drawn into 3×10 ml EDTA-$K_3$ Vacutainer tubes, which were pooled and mixed in a 50 ml, blue cap polypropylene tube. Three ml portions of Mono-Poly Resolving medium (MPRM; ICN #16-980-49) were dispensed into 4 separate 13×100 glass disposable tubes. An additional 0.3 ml of PBS (phosphate buffered saline) was added to each tube and mixed with the MPRM by vigorous vortexing. Exactly 3.5 ml of the blood was carefully layered on top of the four MPRM-water mixtures. The tubes were gradually accelerated to 400×g and spun at this speed for 30 min at room temperature. Tubes were removed from the centrifuge and both the plasma and top cell (mononuclear) layers were removed and discarded. The second layer of cells was carefully collected, pooled and washed with assay buffer. The collected neutrophil cell preparation was then spun at 400×g for 5 min and re-washed once again. The cells were resuspended in assay buffer and counted using a Cell-Dyn 1600 cell counter (Abbott Diagnostics Co.). They were then resuspended in buffer at $9 \times 10^6$ cells/ml and held briefly for addition in a later step of the assay.

LTB4, (Biomol ; ETOH stock @148.5 $\mu$M) was diluted to a 3.9 $\mu$M stock in assay buffer by dilution of 10 $\mu$l ETOH stock+371 $\mu$l assay buffer, mixed well and further diluted 1:100 (100 $\mu$l+9.9 ml buffer) to make a use stock of 39 nm in buffer for later use. The final concentration of $LTB_4$ (3 nM) was determined after several experimental runs.

Exactly 10 $\mu$l of each putative compound/dilution and 10 $\mu$l of anti-CD11b-FITC (FITC=Fluorescein Isothiocyanate; Biosource Intl., #AHS1148) was carefully added to the bottom of 12×75 mm polypropylene tubes (Falcon #2063) as determined by the experimental design. Following this, 100 $\mu$l of the human neutrophil preparation (9E6/ml) was added and mixed well by vortexing. The compound/cell mixtures were incubated together for 15 minutes at room temperature. Following this incubation, 10 $\mu$l of diluted $LTB_4$ stock was added (to make 3 nM final $LTB_4$ concentration), mixed by vortexing and incubated in a 37° C. shaking water bath for 30 min. Following this the tubes were immediately placed on ice for 10 minutes. Following this 1 ml of diluted BD FACS Lyse (Becton Dickinson Fluorescense Activated Cell Sorting Lyse) was added to the tubes and vortexed. 10 minutes later the tubes were spun at 400×g at room temperature. After centrifugation, the tubes were aspirated and re-suspended in 1.0 ml of 1% paraformaldehyde solution.

The samples were then analyzed for fluorescence intensity (linear scale) using an EPICS XL flow cytometer and the "Mo-1 Isolated Neutrophil" protocol.

The mean fluorescence intensity (MFI) for each sample was computed using WinList software and expressed as percentage of maximum MFI.Microsoft Excel and further graphed and analyzed using linear regression.

TABLE 1

Assay Results
Compounds of the Invention

| Example No. | CD11b/CD18 IC50 (nM) |
|---|---|
| 1 | 480 |
| 2 | 5880 |
| 3 | 353;339 |
| 4 | 74;117 |
| 5 | 175;223 |
| 6 | 260 |
| 7 | 2020;3790 |
| 8 | >50000 |
| 9 | 23;20 |
| 10 | 14;4.4;8.3 |
| 11 | 620;2560;1010 |
| 12 | 10000;5700 |
| 13 | 39;54 |
| 14 | 31;30 |
| 15 | 27 |
| 16 | 1080;837 |
| 17 | 11;5.6;8 |

*note
semicolons separate individual assay determinations

TABLE 2

| Assay Results for Comparison Compounds | |
|---|---|
| Compound | IC-50 (nM) ± SEM |
| A* | 1.7 ± 0.25 |
| B | not active |

*= average of 3 tests

Compound A—a known $LTB_4$ antagonist (see, Example 66 of U.S. Pat. No. 5,462,954) which is not heterocycle substituted and is not an aspect of this invention:

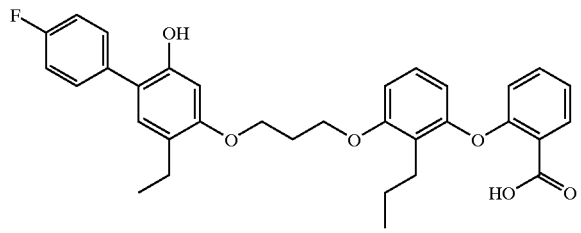

Compound B—a control compound related to Compound A and not an aspect of this invention, represented by the formula:

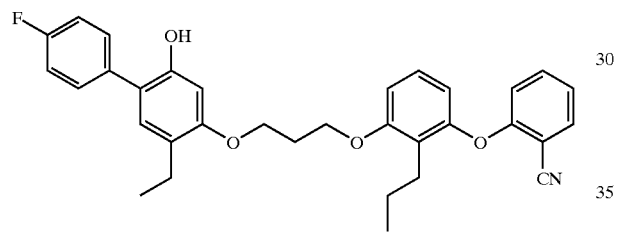

What is claimed is:
1. A compound represented by the formula (I)

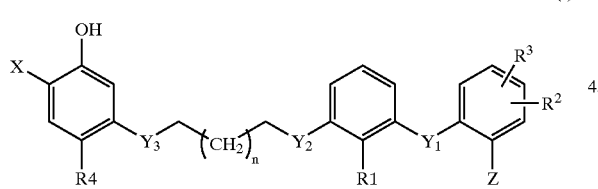

wherein:
X is selected from the group consisting of,
(i) a five membered substituted or unsubstituted heterocyclic radical containing from 1 to 4 hetero atoms independently selected from sulfur, nitrogen or oxygen; and
(ii) a fused bicyclic radical wherein a carbocyclic group is fused to two adjacent carbon atoms of the five membered heterocyclic radical, (i);
$Y_1$ is a bond or divalent linking group containing 1 to 9 atoms;
$Y_2$ and $Y_3$ are divalent linking groups independently selected from —$CH_2$—, —O—, or —S—;
Z is an Acidic Group;
R1 is $C_1$–$C_{10}$ alkyl, aryl, $C_3$–$C_8$ cycloalkyl, $C_2$–$C_{10}$ alkenyl, $C_2$–$C_{10}$ alkynyl, $C_6$–$C_{20}$ aralkyl, $C_6$–$C_{20}$ alkaryl, $C_1$–$C_{10}$ haloalkyl, $C_6$–$C_{20}$ aryloxy, or $C_1$–$C_{10}$ alkoxy;

R2 is hydrogen, halogen, $C_1$–$C_{10}$ haloalkyl, $C_1$–$C_{10}$ alkoxy, $C_1$–$C_{10}$ alkyl, $C_3$–$C_8$ cycloalkyl, Acidic Group, or
—$(CH_2)_{1-7}$—(Acidic Group);
R3 is hydrogen, halogen, $C_1$–$C_{10}$ alkyl, aryl, $C_1$–$C_{10}$ haloalkyl, $C_1$–$C_{10}$ alkoxy, $C_6$–$C_{20}$ aryloxy, or $C_3$–$C_8$ cycloalkyl;
R4 is $C_1$–$C_4$ alkyl, $C_3$–$C_4$ cycloalkyl, —$(CH_2)_{1-7}$—($C_3$–$C_4$ cycloalkyl), $C_2$–$C_4$ alkenyl, $C_2$–$C_4$ alkynyl, benzyl, or aryl; and
n is 0, 1, 2, 3, 4, 5, or 6;
or a pharmaceutically acceptable salt, solvate, or prodrug derivative thereof.

2. The compound of claim 1 wherein X is a heterocyclic radical selected from the group consisting of substituents represented by the following formulae:

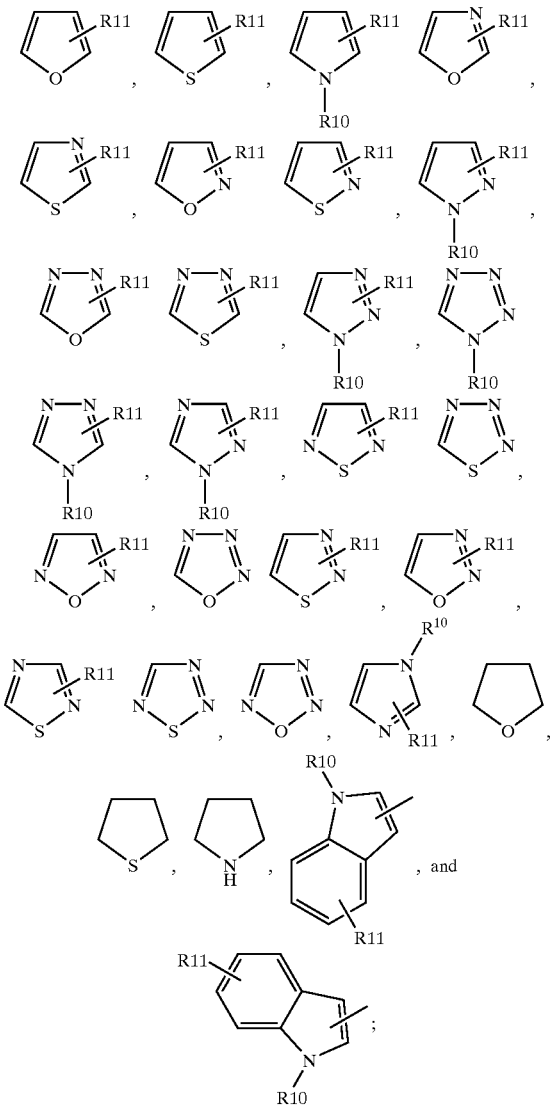

where
R10 is a radical selected from hydrogen or $C_1$–$C_4$ alkyl; and R11 is a radical selected from hydrogen, halo, $C_1$–$C_{10}$ alkyl, $C_1$–$C_{10}$ haloalkyl, $C_1$–$C_{10}$ alkoxy, aryl, or $C_6$–$C_{20}$ aryloxy.

3. The compound of claim 2 wherein the heterocyclic radical is selected from the group consisting of substituents represented by the formulae;

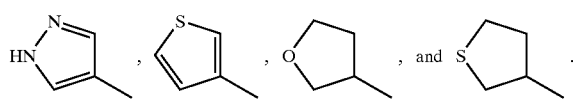

4. The compound of claim 1 wherein $Y_1$ is a divalent linking group selected from the following formulae:

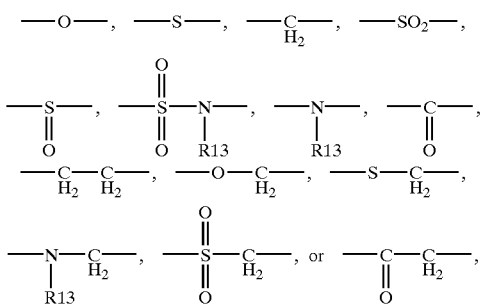

where R13 is hydrogen, methyl, or ethyl.

5. The compound of claim 4 wherein $Y_1$ is the divalent linking group;

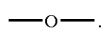

6. The compound of claim 1 wherein the acidic group Z is selected from the following:

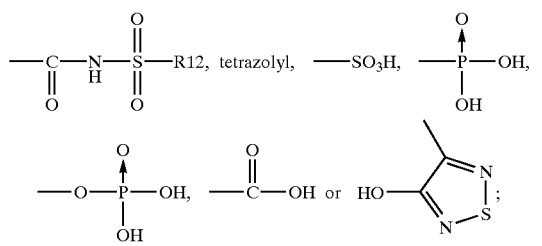

where R12 is $C_1$–$C_{10}$ alkyl, aryl, $C_6$–$C_{20}$ alkaryl, or $C_6$–$C_{20}$ aralkyl.

7. The compound of claim 6 wherein the acidic group Z is selected from -5-tetrazolyl, N-acyl sulfonamide, —SO$_3$H, or carboxyl.

8. The compound of claim 7 wherein the acidic group Z is carboxyl.

9. The compound of claim 1 wherein R1 is selected from methyl, ethyl, n-propyl, isopropyl, n-butyl, sec-butyl, or 2-propenyl.

10. The compound of claim 1 wherein R2 and R3 are independently selected from hydrogen or methyl, ethyl, methoxy, ethoxy, halo, or —CF$_3$.

11. The compound of claim 10 wherein R2 and R3 are hydrogen.

12. The compound of claim 1 wherein R4 is ethyl, propyl, or isopropyl.

13. The compound of claim 1 wherein the numerical value of subscript n is 1.

14. The compound of claim 1 wherein $Y_2$ and $Y_3$ are both —O—.

15. The compound of claim 1 in the form of a sodium salt.

16. The compound of claim 1 in the form of a prodrug which is an ester of the Acidic Group; provided that the Acidic Group is a carboxyl.

17. The compound of claim 16 wherein the Acidic Group is carboxyl and the prodrug is selected from methyl ester, ethyl ester, propyl ester, isopropyl ester, n-butyl ester, isobutyl ester, tert-butyl ester, morpholinoethyl ester, or N,N-diethylglycolamido ester.

18. A compound effective as a leukotriene B4 antagonist, described by formula (II):

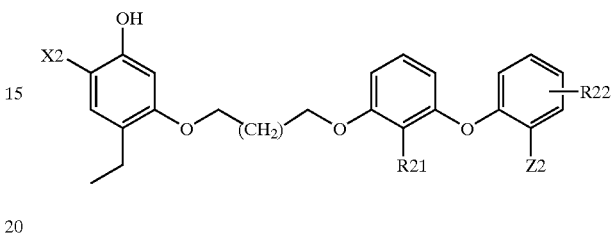

wherein;

X2 is a heterocyclic radical selected from,

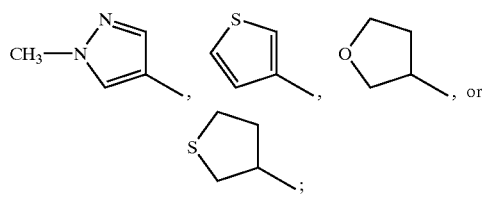

R21 is ethyl, 2-propen-1-yl, 3-propen-1-yl, n-propyl, isopropyl, n-butyl, sec-butyl, or tert-butyl; and R22 is hydrogen, n-butyl, sec-butyl, flouro, chloro, —CF$_3$, or tert-butyl, Z2 is the Acidic Group selected from carboxyl, tetrazolyl, or N-sulfonamidyl;

or a salt, solvate or prodrug thereof.

19. A compound selected from the following:

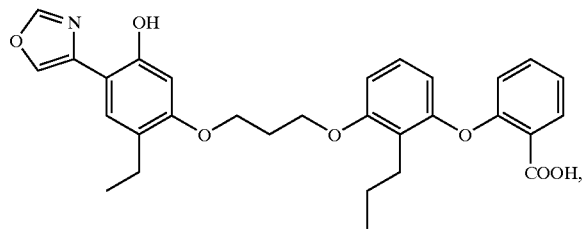

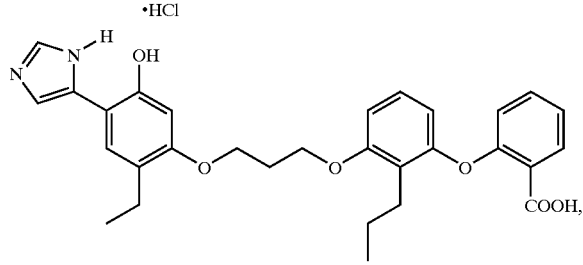

125
-continued
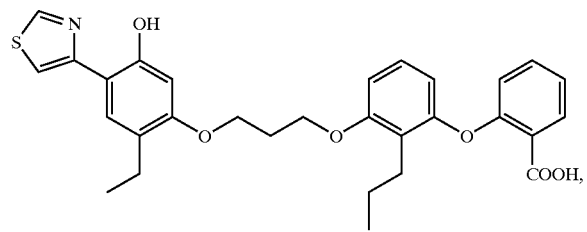
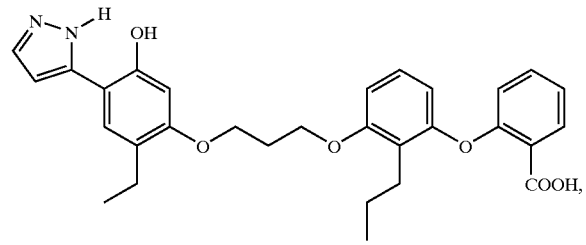
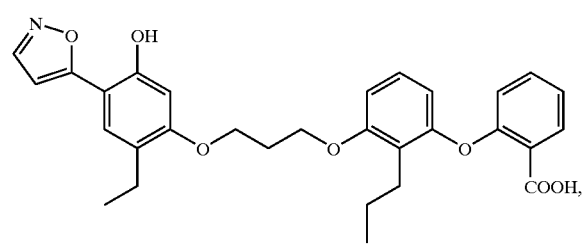
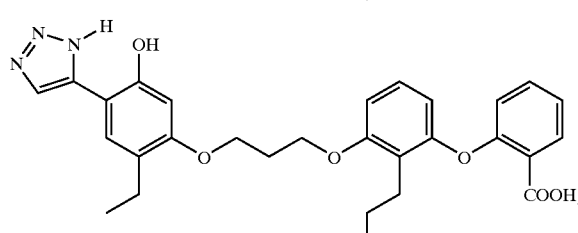
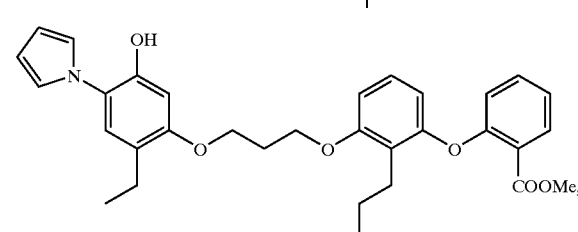
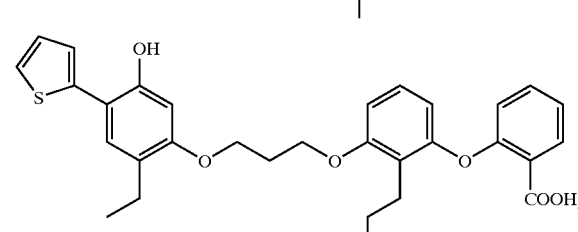
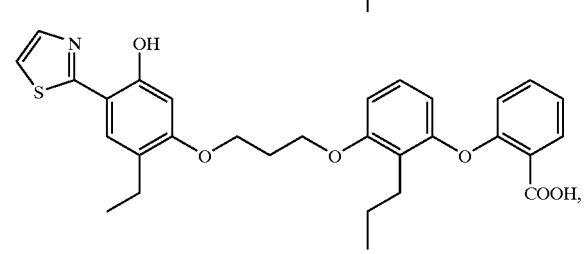
126
-continued
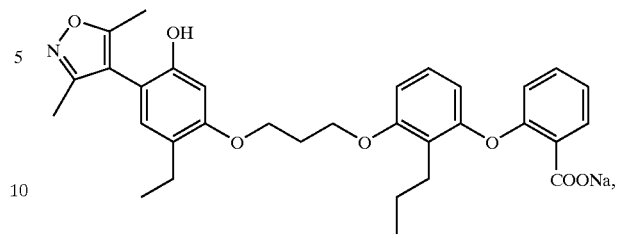
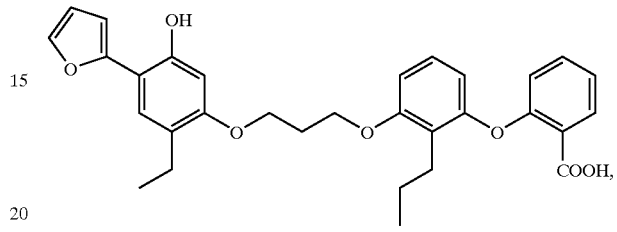
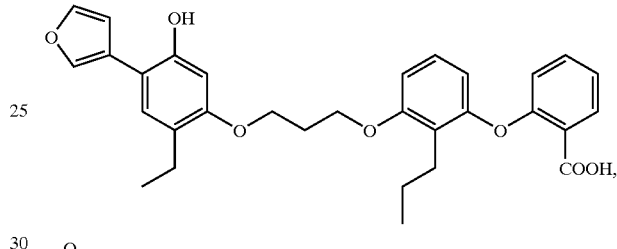
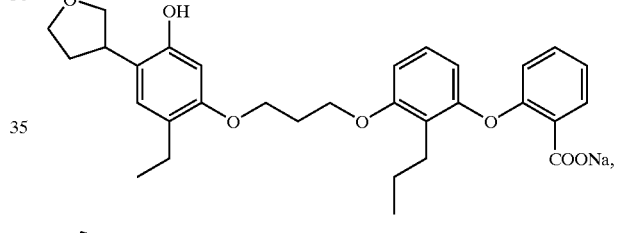
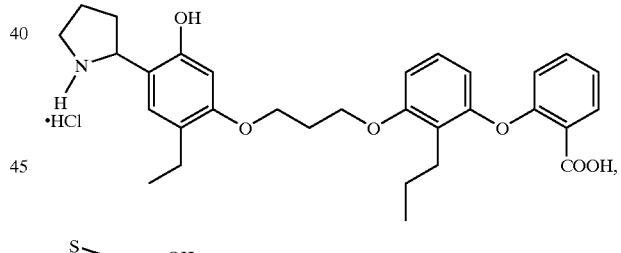
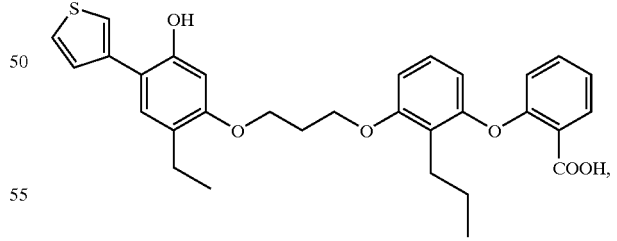
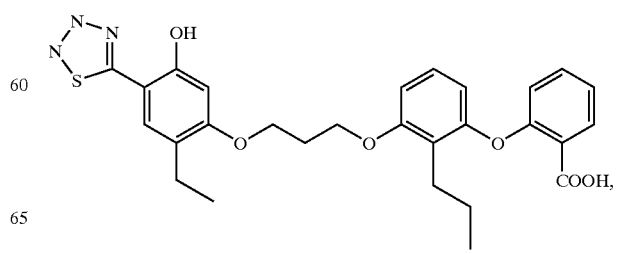

-continued

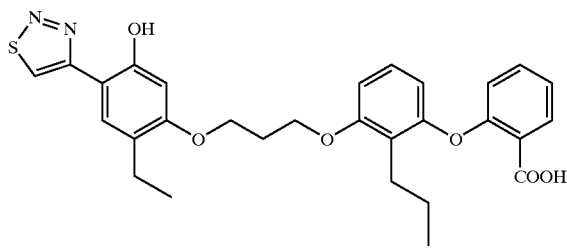

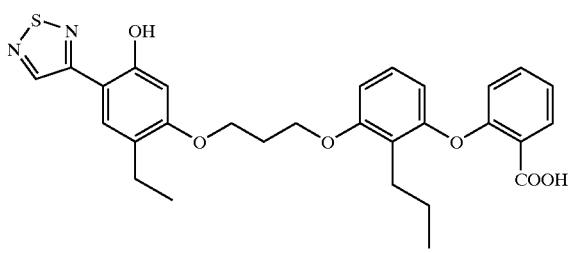

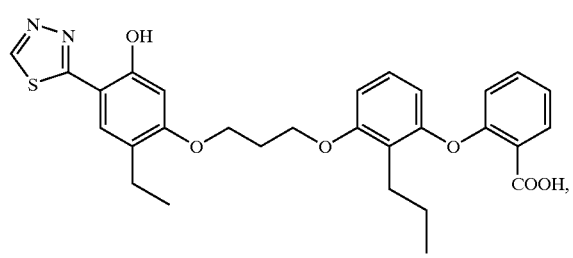

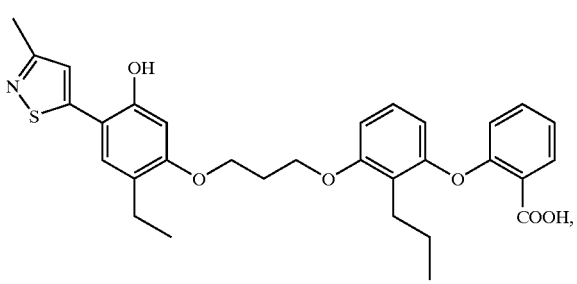

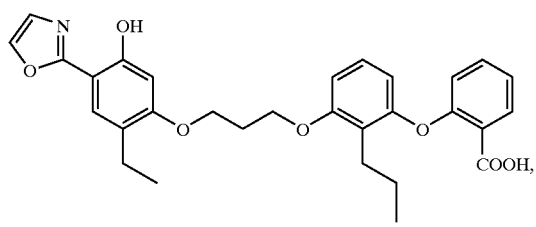

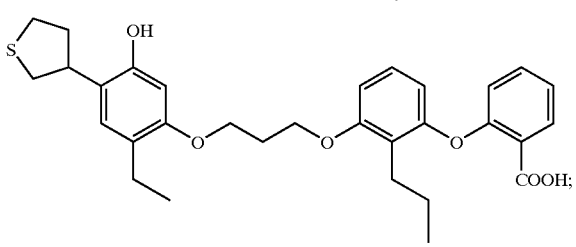

or an acid, salt, solvate or prodrug derivative thereof.

20. A compound selected from the following:

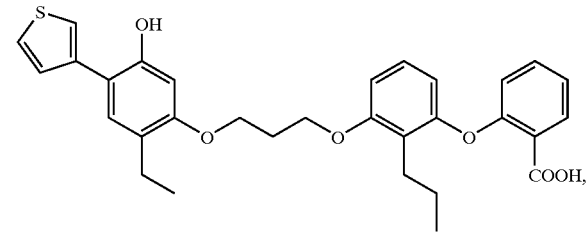

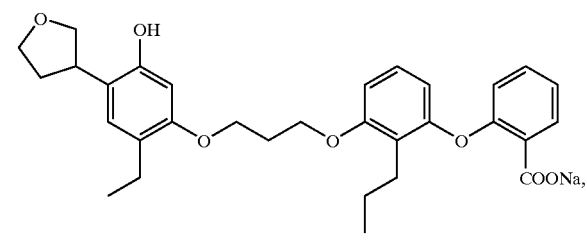

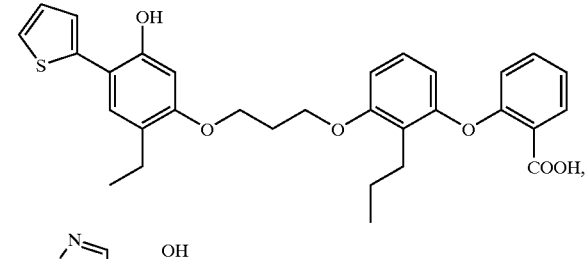

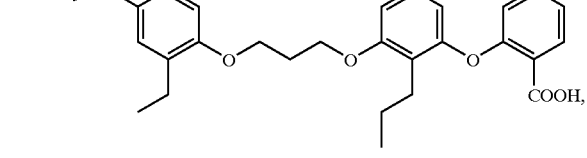

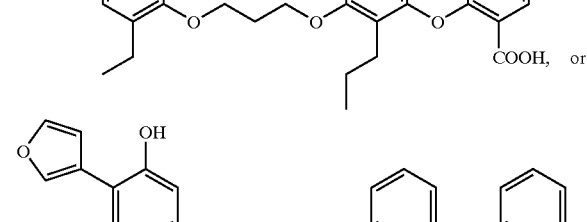

or an acid, salt, solvate or prodrug derivative thereof.

21. A compound of claim 19 wherein the acid, salt and prodrug derivatives are respectively selected from; carboxylic acid, sodium salt, and ester prodrug.

22. A pharmaceutical composition which comprises a therapeutically effective amount of a compound according to claim 1 and a pharmaceutically acceptable carrier or diluent.

23. A method for the treatment or prevention of Inflammatory Diseases, which comprises administering to a mammal in need thereof a therapeutically effective amount of a compound according to claim 1.

24. A method for in vivo inhibition of leukotriene $B_4$ in a mammal in need thereof, which comprises administering to said mammal a therapeutically effective amount of a compound according to claim 1.

25. The method of claim 24 wherein the route of administration is oral and the dose is about 1 to about 1000 milligrams per day.

26. The method of claim 24 wherein the route of administration is parenteral and the dose is about 0.1 to about 100 milligrams per day.

* * * * *

UNITED STATES PATENT AND TRADEMARK OFFICE
CERTIFICATE OF CORRECTION

PATENT NO.   : 6,797,723 B1  Page 1 of 1
DATED        : September 28, 2004
INVENTOR(S)  : Sawyer et al.

It is certified that error appears in the above-identified patent and that said Letters Patent is hereby corrected as shown below:

Column 125,
Line 57, please insert -- 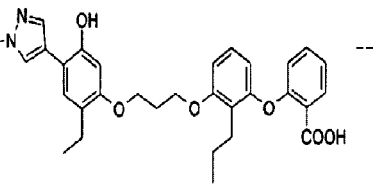 --

Signed and Sealed this

Seventh Day of December, 2004

JON W. DUDAS
*Director of the United States Patent and Trademark Office*